(12) United States Patent
Roy et al.

(10) Patent No.: US 10,434,147 B2
(45) Date of Patent: Oct. 8, 2019

(54) TREATMENT TYPE 2 DIABETES MELLITUS PATIENTS

(71) Applicant: Sanofi-Aventis Deutschland GmbH, Frankfurt (DE)

(72) Inventors: Christine Roy, Paris (FR); Elisabeth Souhami, Paris (FR); Nacima Demil, Paris (FR); Jenny Ye, Bridgewater, NJ (US)

(73) Assignee: SANOFI-AVENTIS DEUTSCHLAND GMBH, Frankfurt (DE)

( * ) Notice: Subject to any disclaimer, the term of this patent is extended or adjusted under 35 U.S.C. 154(b) by 0 days.

(21) Appl. No.: 15/646,760

(22) Filed: Jul. 11, 2017

(65) Prior Publication Data

US 2018/0092965 A1    Apr. 5, 2018

Related U.S. Application Data

(62) Division of application No. 15/068,286, filed on Mar. 11, 2016.

(30) Foreign Application Priority Data

Mar. 13, 2015 (EP) .................................. 15159064

(51) Int. Cl.
   *A61K 31/155* (2006.01)
   *A61K 38/26* (2006.01)
   *A61K 38/28* (2006.01)
   *A61K 9/00* (2006.01)

(52) U.S. Cl.
   CPC ............ *A61K 38/28* (2013.01); *A61K 9/0019* (2013.01); *A61K 31/155* (2013.01); *A61K 38/26* (2013.01)

(58) Field of Classification Search
   None
   See application file for complete search history.

(56) References Cited

U.S. PATENT DOCUMENTS

| | | |
|---|---|---|
| 3,758,683 A | 9/1973 | Jackson |
| 3,868,358 A | 2/1975 | Jackson |
| 4,153,689 A | 5/1979 | Hirai et al. |
| 4,165,370 A | 8/1979 | Coval |
| 4,258,134 A | 3/1981 | Yoshida et al. |
| 4,367,737 A | 1/1983 | Kozam et al. |
| 4,608,364 A | 8/1986 | Grau |
| 4,614,730 A | 9/1986 | Hansen et al. |
| 4,644,057 A | 2/1987 | Bicker et al. |
| 4,689,042 A | 8/1987 | Sarnoff et al. |
| 4,701,440 A | 10/1987 | Grau |
| 4,731,405 A | 3/1988 | Kirsch et al. |
| 4,783,441 A | 11/1988 | Thurow |
| 4,839,341 A | 6/1989 | Massey et al. |
| 4,863,902 A | 9/1989 | Amagase et al. |
| 4,885,164 A | 12/1989 | Thurow |
| 4,923,162 A | 5/1990 | Fleming et al. |
| 4,959,351 A | 9/1990 | Grau |
| 4,960,702 A | 10/1990 | Rice et al. |
| 4,994,439 A | 2/1991 | Longenecker et al. |
| 5,008,241 A | 4/1991 | Markussen et al. |
| 5,034,415 A | 7/1991 | Rubin |
| 5,070,186 A | 12/1991 | Joergensen |
| 5,101,013 A | 3/1992 | Doerschug et al. |
| 5,177,058 A | 1/1993 | Doerschug |
| 5,187,177 A | 2/1993 | Garzaran |
| 5,227,293 A | 7/1993 | Stengelin et al. |
| 5,253,785 A | 10/1993 | Haber et al. |
| 5,272,135 A | 12/1993 | Takruri |
| 5,358,708 A | 10/1994 | Patel |
| 5,358,857 A | 10/1994 | Stengelin et al. |
| 5,370,629 A | 12/1994 | Michel et al. |
| 5,397,771 A | 3/1995 | Bechgaard et al. |
| 5,407,609 A | 4/1995 | Tice et al. |
| 5,424,286 A | 6/1995 | Eng |
| 5,428,006 A | 6/1995 | Bechgaard et al. |
| 5,473,049 A | 12/1995 | Obermeier et al. |
| 5,474,978 A | 12/1995 | Bakaysa et al. |
| 5,478,323 A | 12/1995 | Westwood et al. |
| 5,496,924 A | 3/1996 | Habermann et al. |
| 5,506,203 A | 4/1996 | Baeckstroem et al. |
| 5,509,905 A | 4/1996 | Michel |
| 5,514,646 A | 5/1996 | Chance et al. |
| 5,524,286 A | 6/1996 | Chiesa et al. |
| 5,534,488 A | 7/1996 | Hoffmann |
| 5,545,618 A | 8/1996 | Buckley et al. |
| 5,547,929 A | 8/1996 | Anderson, Jr. et al. |

(Continued)

FOREIGN PATENT DOCUMENTS

| | | |
|---|---|---|
| AU | 593274 B2 | 2/1990 |
| AU | 612324 B2 | 7/1991 |

(Continued)

OTHER PUBLICATIONS

Aguilar, "Heart failure and diabetes: Time to pay attention" American Heart Journal, 162(5):795-97 (Nov. 2011).

(Continued)

*Primary Examiner* — Julie Ha
*Assistant Examiner* — Kristina M Hellman
(74) *Attorney, Agent, or Firm* — Lathrop Gage LLP; James V. DeGiulio

(57) ABSTRACT

A pharmaceutical combination for use in glycemic control in a type 2 diabetes mellitus patient, said combination comprising (i) lixisenatide or/and a pharmaceutically acceptable salt thereof, (ii) insulin glargine or/and a pharmaceutically acceptable salt thereof, and (iii) optionally metformin or/and a pharmaceutically acceptable salt thereof.

4 Claims, 6 Drawing Sheets

Specification includes a Sequence Listing.

(56) References Cited

U.S. PATENT DOCUMENTS

| | | |
|---|---|---|
| 5,559,094 A | 9/1996 | Brems et al. |
| 5,595,756 A | 1/1997 | Bally et al. |
| 5,597,796 A | 1/1997 | Brange |
| 5,614,219 A | 3/1997 | Wunderlich et al. |
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Doerschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,879,584 A | 3/1999 | Bianchetti et al. |
| 5,935,566 A | 8/1999 | Yuen et al. |
| 5,948,751 A | 9/1999 | Kimer et al. |
| 5,952,297 A | 9/1999 | De et al. |
| 5,985,309 A | 11/1999 | Edwards et al. |
| 5,986,048 A | 11/1999 | Rubroder et al. |
| 6,006,753 A | 12/1999 | Efendic |
| 6,034,054 A | 3/2000 | Defelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Doerschug |
| 6,110,703 A | 8/2000 | Egel-Mitani et al. |
| 6,174,856 B1 | 1/2001 | Langballe et al. |
| 6,191,102 B1 | 2/2001 | Dimarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | Desimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,410,511 B2 | 6/2002 | L'Italien et al. |
| 6,417,164 B1 | 7/2002 | Kolterman et al. |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van et al. |
| 6,737,401 B2 | 5/2004 | Kim et al. |
| 6,767,887 B1 | 7/2004 | Hoffmann et al. |
| 6,818,738 B2 | 11/2004 | Havelund |
| 6,852,694 B2 | 2/2005 | Van et al. |
| 6,875,589 B1 | 4/2005 | Doerschug et al. |
| 6,902,744 B1 | 6/2005 | Kolterman et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | Defelippis et al. |
| 7,115,563 B2 | 10/2006 | Younis et al. |
| 7,119,086 B2 | 10/2006 | Di et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | Defelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuehn et al. |
| 8,633,156 B2 | 1/2014 | Habermann et al. |
| 8,735,349 B2 | 5/2014 | Silvestre et al. |
| 8,901,484 B2 | 12/2014 | Vogel et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | Defelippis et al. |
| 2003/0170691 A1 | 9/2003 | Gimeno et al. |
| 2003/0212248 A1 | 11/2003 | Furman |
| 2004/0022792 A1 | 2/2004 | Klinke |
| 2004/0037893 A1 | 2/2004 | Hansen et al. |
| 2004/0048783 A1 | 3/2004 | Brunner-Schwarz et al. |
| 2004/0092590 A1 | 5/2004 | Arterburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | Defelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0104210 A1 | 4/2009 | Tota et al. |
| 2009/0142338 A1 | 6/2009 | Levetan |
| 2009/0148534 A1 | 6/2009 | Yasugi |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |

(56) References Cited

U.S. PATENT DOCUMENTS

| | | |
|---|---|---|
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0122776 A1 | 5/2012 | Graefe-Mody et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0116179 A1 | 5/2013 | Hess et al. |
| 2013/0189328 A1 | 7/2013 | Cleemann et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2013/0317477 A1 | 11/2013 | Edwards et al. |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |
| 2014/0371141 A1 | 12/2014 | Souhami et al. |
| 2014/0379277 A1 | 12/2014 | Vogel et al. |
| 2016/0199452 A1 | 7/2016 | Souhami et al. |
| 2016/0235818 A1 | 8/2016 | Bergmann et al. |
| 2016/0287674 A1 | 10/2016 | Roy et al. |
| 2016/0296601 A1 | 10/2016 | Belder et al. |

FOREIGN PATENT DOCUMENTS

| | | |
|---|---|---|
| AU | 2000-72263 | 2/2001 |
| CA | 1173388 A | 8/1984 |
| CA | 1258427 A | 8/1989 |
| CA | 1336329 C | 7/1995 |
| CA | 1341203 C | 3/2001 |
| CA | 2 685 638 | 5/2011 |
| CN | 1276731 A | 12/2000 |
| CN | 1413582 A | 4/2003 |
| CN | 1662252 A | 8/2005 |
| CN | 101366692 A | 2/2009 |
| CN | 101444618 A | 6/2009 |
| CN | 101454019 A | 6/2009 |
| CN | 101670096 A | 3/2010 |
| DE | 19637230 A1 | 3/1998 |
| DE | 102008003566 A1 | 7/2009 |
| DE | 102008003568 A1 | 7/2009 |
| DE | 102008053048 A1 | 4/2010 |
| EP | 0046979 B1 | 9/1983 |
| EP | 0132769 A1 | 2/1985 |
| EP | 0140084 A1 | 5/1985 |
| EP | 0166529 A1 | 1/1986 |
| EP | 0200383 A2 | 11/1986 |
| EP | 0211299 A2 | 2/1987 |
| EP | 0214826 A2 | 3/1987 |
| EP | 0224885 A1 | 6/1987 |
| EP | 0227938 A2 | 7/1987 |
| EP | 0229998 A2 | 7/1987 |
| EP | 0254516 A2 | 1/1988 |
| EP | 0368187 A2 | 5/1990 |
| EP | 0375437 A2 | 6/1990 |
| EP | 0383472 A2 | 8/1990 |
| EP | 0194864 B1 | 6/1992 |
| EP | 0419504 B1 | 1/1994 |
| EP | 0600372 A1 | 6/1994 |
| EP | 0668282 A1 | 8/1995 |
| EP | 0678522 A1 | 10/1995 |
| EP | 0837072 A2 | 4/1998 |
| EP | 0845265 A1 | 6/1998 |
| EP | 0885961 A1 | 12/1998 |
| EP | 1076066 A1 | 2/2001 |
| EP | 1172114 A2 | 1/2002 |
| EP | 1222207 A1 | 7/2002 |
| EP | 1523993 A1 | 4/2005 |
| EP | 2112161 A2 | 10/2009 |
| EP | 2324853 A1 | 5/2011 |
| EP | 2329848 A1 | 6/2011 |
| EP | 2389945 A1 | 11/2011 |
| EP | 0 921 812 B2 | 12/2011 |
| EP | 0921812 B2 | 12/2011 |
| EP | 2387989 B1 | 7/2014 |
| FR | 2456522 A1 | 12/1980 |
| GB | 835638 A | 5/1960 |
| GB | 840870 A | 7/1960 |
| GB | 1527605 A | 10/1978 |
| GB | 1554157 A | 10/1979 |
| JP | S61212598 A | 9/1986 |
| JP | S6399096 A | 4/1988 |
| JP | H02218696 A | 8/1990 |
| JP | H02264798 A | 10/1990 |
| JP | H03504240 A | 9/1991 |
| JP | H06506444 A | 7/1994 |
| JP | 2001521004 A | 11/2001 |
| JP | 2002516880 A | 6/2002 |
| JP | 2006137678 A | 6/2006 |
| JP | 2007204498 A | 8/2007 |
| JP | 2009091363 A | 4/2009 |
| RU | 2386631 C2 | 4/2010 |
| TW | 157005 B | 5/1991 |
| TW | 562806 B | 11/2003 |
| WO | WO-8300288 A1 | 2/1983 |
| WO | WO-8806599 A1 | 9/1988 |
| WO | WO-8910937 A1 | 11/1989 |
| WO | WO-9007522 A1 | 7/1990 |
| WO | WO-9011299 A1 | 10/1990 |
| WO | WO-9103550 A1 | 3/1991 |
| WO | WO-9116929 A1 | 11/1991 |
| WO | WO-9200321 A1 | 1/1992 |
| WO | WO-9212999 A1 | 8/1992 |
| WO | WO-9318786 A1 | 9/1993 |
| WO | WO-9414461 A1 | 7/1994 |
| WO | WO-9500550 A1 | 1/1995 |
| WO | WO-9524183 A1 | 9/1995 |
| WO | WO-9604307 A1 | 2/1996 |
| WO | WO-9607399 A1 | 3/1996 |
| WO | WO-9611705 A1 | 4/1996 |
| WO | WO-9632414 A1 | 10/1996 |

(56) References Cited

FOREIGN PATENT DOCUMENTS

| | | |
|---|---|---|
| WO | WO-9634882 A1 | 11/1996 |
| WO | WO-9641606 A2 | 12/1996 |
| WO | WO-9701331 A2 | 1/1997 |
| WO | WO-9748413 A1 | 12/1997 |
| WO | WO-9805351 A1 | 2/1998 |
| WO | WO-9808531 A1 | 3/1998 |
| WO | WO-9808871 A1 | 3/1998 |
| WO | WO-9808873 A1 | 3/1998 |
| WO | WO-9819698 A1 | 5/1998 |
| WO | WO-9830231 A1 | 7/1998 |
| WO | WO-9835033 A1 | 8/1998 |
| WO | WO-9839022 A1 | 9/1998 |
| WO | WO-9842749 A1 | 10/1998 |
| WO | WO-9856406 A1 | 12/1998 |
| WO | WO-9856418 A1 | 12/1998 |
| WO | WO-9907404 A1 | 2/1999 |
| WO | WO-9921573 A1 | 5/1999 |
| WO | WO-9921578 A1 | 5/1999 |
| WO | WO-9924071 A1 | 5/1999 |
| WO | WO-9925727 A2 | 5/1999 |
| WO | WO-9925728 A1 | 5/1999 |
| WO | WO-9940788 A1 | 8/1999 |
| WO | WO-9943708 A1 | 9/1999 |
| WO | WO-9946283 A1 | 9/1999 |
| WO | WO-9962558 A1 | 12/1999 |
| WO | WO-0023098 A1 | 4/2000 |
| WO | WO-0023099 A1 | 4/2000 |
| WO | WO-0029013 A1 | 5/2000 |
| WO | WO-0041546 A2 | 7/2000 |
| WO | WO-0066629 A1 | 11/2000 |
| WO | WO-0072582 A1 | 11/2000 |
| WO | WO-0074736 A1 | 12/2000 |
| WO | WO-0100223 A2 | 1/2001 |
| WO | WO-0102039 A1 | 1/2001 |
| WO | WO-0104156 A1 | 1/2001 |
| WO | WO-0112155 A1 | 2/2001 |
| WO | WO-0121154 A2 | 3/2001 |
| WO | WO 01/24814 | 4/2001 |
| WO | WO-0125278 A1 | 4/2001 |
| WO | WO-0128555 A1 | 4/2001 |
| WO | WO 01/32157 | 5/2001 |
| WO | WO-0137808 A1 | 5/2001 |
| WO | WO-0143762 A2 | 6/2001 |
| WO | WO-0151071 A2 | 7/2001 |
| WO | WO-0152937 A1 | 7/2001 |
| WO | WO-0193837 A2 | 12/2001 |
| WO | WO-0200243 A2 | 1/2002 |
| WO | WO-0224214 A2 | 3/2002 |
| WO | WO-02064115 A1 | 8/2002 |
| WO | WO-02065985 A2 | 8/2002 |
| WO | WO-02066628 A2 | 8/2002 |
| WO | WO-02068660 A1 | 9/2002 |
| WO | WO-02070722 A1 | 9/2002 |
| WO | WO-02076495 A1 | 10/2002 |
| WO | WO-02079250 A1 | 10/2002 |
| WO | WO-03002021 A2 | 1/2003 |
| WO | WO-03020201 A2 | 3/2003 |
| WO | WO-03035028 A1 | 5/2003 |
| WO | WO-03035051 A2 | 5/2003 |
| WO | WO-03044210 A2 | 5/2003 |
| WO | WO-03053339 A2 | 7/2003 |
| WO | WO-03066084 A1 | 8/2003 |
| WO | WO-03094951 A1 | 11/2003 |
| WO | WO-03094956 A1 | 11/2003 |
| WO | WO-03101395 A2 | 12/2003 |
| WO | WO-03105888 A1 | 12/2003 |
| WO | WO-2004005342 A1 | 1/2004 |
| WO | WO-2004035623 A2 | 4/2004 |
| WO | WO 2004/050115 | 6/2004 |
| WO | WO-2004045592 A2 | 6/2004 |
| WO | WO-2004064862 A1 | 8/2004 |
| WO | WO-2004078196 A1 | 9/2004 |
| WO | WO-2004078197 A1 | 9/2004 |
| WO | WO-2004078198 A1 | 9/2004 |
| WO | WO-2004080480 A1 | 9/2004 |
| WO | WO-2004096854 A2 | 11/2004 |
| WO | WO-2004105781 A2 | 12/2004 |
| WO | WO-2004107979 A1 | 12/2004 |
| WO | WO-2005021022 A2 | 3/2005 |
| WO | WO-2005023291 A2 | 3/2005 |
| WO | WO-2005028516 A2 | 3/2005 |
| WO | WO-2005046716 A1 | 5/2005 |
| WO | WO-2005048950 A2 | 6/2005 |
| WO | WO-2005112949 A1 | 12/2005 |
| WO | WO-2005117948 A1 | 12/2005 |
| WO | WO-2006000567 A2 | 1/2006 |
| WO | WO 2006/017541 | 2/2006 |
| WO | WO-2006015879 A1 | 2/2006 |
| WO | WO-2006029634 A2 | 3/2006 |
| WO | WO-2006051103 A2 | 5/2006 |
| WO | WO-2006051110 A2 | 5/2006 |
| WO | WO-2006058620 A2 | 6/2006 |
| WO | WO-2006110551 A2 | 10/2006 |
| WO | WO-2007001150 A2 | 1/2007 |
| WO | WO-2007006307 A2 | 1/2007 |
| WO | WO-2007024700 A2 | 3/2007 |
| WO | WO-2007028394 A2 | 3/2007 |
| WO | WO-2007031187 A1 | 3/2007 |
| WO | WO-2007035665 A1 | 3/2007 |
| WO | WO-2007036299 A2 | 4/2007 |
| WO | WO-2007037607 A1 | 4/2007 |
| WO | WO-2007044867 A2 | 4/2007 |
| WO | WO-2007050656 A2 | 5/2007 |
| WO | WO 2007/081792 | 7/2007 |
| WO | WO-2007075534 A2 | 7/2007 |
| WO | WO-2007081824 A2 | 7/2007 |
| WO | WO-2007082381 A1 | 7/2007 |
| WO | WO-2007095288 A2 | 8/2007 |
| WO | WO-2007104786 A1 | 9/2007 |
| WO | WO-2007109221 A2 | 9/2007 |
| WO | WO-2007113205 A1 | 10/2007 |
| WO | WO-2007120899 A2 | 10/2007 |
| WO | WO-2008006496 A1 | 1/2008 |
| WO | WO-2008013938 A2 | 1/2008 |
| WO | WO-2008021560 A2 | 2/2008 |
| WO | WO-2008023050 A1 | 2/2008 |
| WO | WO-2008028914 A1 | 3/2008 |
| WO | WO-2008034881 A1 | 3/2008 |
| WO | WO-2008124522 A2 | 10/2008 |
| WO | WO-2008133908 A2 | 11/2008 |
| WO | WO-2008145323 A1 | 12/2008 |
| WO | WO-2009004627 A2 | 1/2009 |
| WO | WO-2009030498 A2 | 3/2009 |
| WO | WO-2009030499 A1 | 3/2009 |
| WO | WO-2009039963 A1 | 4/2009 |
| WO | WO-2009048959 A1 | 4/2009 |
| WO | WO-2009056569 A1 | 5/2009 |
| WO | WO-2009063072 A2 | 5/2009 |
| WO | WO-2009087081 A2 | 7/2009 |
| WO | WO-2009087082 | 7/2009 |
| WO | WO-2009089181 A1 | 7/2009 |
| WO | WO-2009098318 A1 | 8/2009 |
| WO | WO-2009102467 A2 | 8/2009 |
| WO | WO-2009134380 A2 | 11/2009 |
| WO | WO-2009143014 A1 | 11/2009 |
| WO | WO-2010030670 A2 | 3/2010 |
| WO | WO-2010043566 A2 | 4/2010 |
| WO | WO-2010044867 A1 | 4/2010 |
| WO | WO 2010/089304 | 8/2010 |
| WO | WO-2010092163 A2 | 8/2010 |
| WO | WO 2010/138671 | 12/2010 |
| WO | WO-2011012719 A2 | 2/2011 |
| WO | WO-2011017554 A2 | 2/2011 |
| WO | WO-2011029892 A2 | 3/2011 |
| WO | WO-2011058082 A1 | 5/2011 |
| WO | WO-2011058083 A1 | 5/2011 |
| WO | WO-2011089203 A1 | 7/2011 |
| WO | WO-2011103575 A1 | 8/2011 |
| WO | WO-2011122921 A2 | 10/2011 |
| WO | WO-2011128374 A1 | 10/2011 |
| WO | WO-2011144673 A2 | 11/2011 |
| WO | WO-2011144674 A2 | 11/2011 |
| WO | WO-2011147980 A1 | 12/2011 |
| WO | WO-2011157402 A1 | 12/2011 |

(56) References Cited

FOREIGN PATENT DOCUMENTS

| WO | WO-2011160066 A1 | 12/2011 |
|---|---|---|
| WO | WO-2012012352 A2 | 1/2012 |
| WO | WO-2012028172 A1 | 3/2012 |
| WO | WO-2012055967 A2 | 5/2012 |
| WO | WO-2012065996 A1 | 5/2012 |
| WO | WO-2012066086 A1 | 5/2012 |
| WO | WO-2012080320 A1 | 6/2012 |
| WO | WO-2012104342 A1 | 8/2012 |
| WO | WO-2012125569 A2 | 9/2012 |
| WO | 2012156298 A1 | 11/2012 |
| WO | WO-2012156296 A1 | 11/2012 |
| WO | WO-2012156299 A1 | 11/2012 |
| WO | WO-2012177929 A2 | 12/2012 |
| WO | WO-2013060850 A1 | 5/2013 |
| WO | WO-2014017849 A1 | 1/2014 |
| WO | WO-2014118355 A1 | 8/2014 |
| WO | WO 2014/131815 | 9/2014 |
| WO | 2014161837 A1 | 10/2014 |
| WO | WO-2014202483 A1 | 12/2014 |
| WO | WO 2015/059302 | 4/2015 |

OTHER PUBLICATIONS

Ahmad & Swann, and Bloomgren "Exenatide and rare adverse events." N Engl J Med 358(18):1969-72 (May 2008).
Ahren, "GLP-1 for type 2 diabetes", Experimental Cell Research, 317(9):1239-45 (Jan. 2011).
Albert-Ludwigs University Freiburg, Institute fur Medizinische Biometrie und Statistik "Non-Inferiority Trials" dated Mar. 29, 2017, one page.
American Diabetes Association, "Diagnosis and Classification of Diabetes Mellitus", Diabetes Care, 37 (Supplement 1):S81-S90 (Jan. 2014).
American Diabetes Association Annual Scientific Sessions, "New Diabetes Compound AVE0010 Showed Clear Dose Response Results With Once-A-Day Injection in Phase IIb Study", published Jun. 9, 2008, two pages.
American Diabetes Association, "Standards of Medical Care in Diabetes." Diabetes Care 28(Supplement 1): S4-S36 (Jan. 2005).
American Diabetes Association, "Standards of Medical Care in Diabetes—2008" Diabetes Care 31(Supplement 1): S12-S54.
American Diabetes Association, "Standards of Medical Care in Diabetes—2017" Diabetes Care 40(Supplement 1):S1-S142 (Jan. 2017).
Bastyr et al., "Therapy focused on lowering postprandial glucose, not fasting glucose, may be superior for lowering HbA1c. IOEZ Study Group." Diabetes Care 23(9):1236-41 (Sep. 2000).
Bell et al., "Sequence of the human insulin gene." 284(5751):26-32 (Mar. 1980).
Bennett, "Impact of the new WHO classification and diagnostic criteria." Diabetes Obes Metab 1(Supplement 2):S1-S6 (1999).
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Bergenstal et al., "Type 2 Diabetes: Assessing the Relative Risks and Benefits of Glucose-lowering Medications" The American Journal of Medicine 123(4):e9-e18 (Apr. 2010).
Bucceri et al., "Gallbladder and gastric emptying: relationship to cholecystokininemia in diabetics." Eur. J. Intern. Med. 13(2):123-28 (Mar. 2002).
Buse et al., "Effects of exenatide (Exendin-4) on glycemic control over 30 weeks in sulfonylurea-treated patients with type 2 diabetes." Diabetes Care 27(11):2628-35 (Nov. 2004).
Byetta® Labeling Revision, pp. 1-24 (Jan. 11, 2008).

Byetta® European Public Assessment Report (EPAR), pp. 1-36 (Feb. 16, 2012).
Byetta® Prescribing Information, pp. 1-34 (Revised Oct. 2009).
Byetta® Summary of Product Characteristics, updated Jul. 22, 2016, last accessed Jul. 31, 2017, pp. 1-13.
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Clinical Trials Archive for Trial No. NCT00763815 updated Feb. 21, 2014. Accessed at https://clinicaltrials.gov/archive/NCT00763815/2014_02_21/changes Accessed on Nov. 13, 2017. pp. 1-13.
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
D'Alessio et al., "The role of dysregulated glucagon secretion in type 2 diabetes" Diabetes, Obesity and Metabolism, 13(Supppl. 1):126-132 (Oct. 2011).
Definition of "prevent" Dictionary.com; last accessed Sep. 29, 2016, pp. 1-6.
Definition of "induce" Dictionary.com; last accessed Sep. 29, 2016, pp. 1-6.
Definition of "reduce" Dictionary.com; last accessed Aug. 13, 2017, pp. 1-4.
Degn et al., "Effect of Intravenous Infusion of Exenatide (Synthetic Exendin-4) on Glucose-Dependent Insulin Secretion and Counterregulation During Hypoglycemia." Diabetes 53(9):2397-2403 (Sep. 2004).
De la Loge et al., "Cross-cultural development and validation of a patient self-administered questionnaire to assess quality of life in upper gastrointestinal disorders: The PAGI-QOL." Quality of Life Research 13(10):1751-62 (Dec. 2004).
Denker et al., "Exenatide (Exendin-4)-Induced Pancreatitis: A case report" Diabetes Care 29(2):471 (Feb. 2006).
De Venciana et al., "Postprandial versus preprandial blood glucose monitoring in women with gestational diabetes mellitus requiring insulin therapy" N Engl J Med 333(19):1237-41 (Nov. 1995).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
Donahue et al., "Postchallenge glucose concentration and coronary heart disease in men of Japanese ancestry. Honolulu Heart Program." Diabetes 36(6):689-92 (Jun. 1987).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
Eckert et al., "Assessing the progression of Parkinson's disease: A metabolic network approach," Lancet Neurol. 6 (10):926-32 (Oct. 2007).
European Medicines Agency, "Guideline on clinical investigation of medicinal products in the treatment of hypertension" (EMA/238/1995 Rev 3) pp. 1-18 (Nov. 18, 2010).
European Diabetes Policy Group, "A desktop guide to Type 2 diabetes mellitus." Diabetic Medicine 16(9):716-730 (1999).
Faichney, "Metformin in Type 1 diabetes: Is This a Good or Bad Idea?" Diabetes Care 26(5):1655 (May 2003).
FDA, "Guidance of Industry—Bioequivalence studies with pharmacokinetic endpoints for drugs submitted under an ANDA" Draft Guidance by the U.S. Department of Health and Human Services, Food and Drug Administration, Center for Drug Evaluation and Research (CDER), Dec. 2013, pp. 1-24.
Forlenza et al., "Diagnosis and biomarkers of predementia in Alzheimer's disease," BMC Medicine 8:89 pp. 1-14 (Dec. 2010).
Game "Novel hypoglycaemic agents: Considerations in patients with chronic kidney disease" Nephron Clin Pract. 126(1):14-18 (Jan. 11, 2014).
Ganz et al., "The association of body mass index with the risk of type 2 diabetes: a case-control study nested in an electronic health records system in the United States." Diabetology & Metabolic Syndrome, 6:50, pp. 1-8 (Apr. 2014).

(56) References Cited

OTHER PUBLICATIONS

GenBank: AAP20099.1 "Interferon Alpha 2B [*Homo sapiens*]" dated Apr. 30, 2003; accessed Jan. 18, 2017, one page.
GenBank: AAA59149.1 "Interleukin 4 [*Homo sapiens*]" dated Jan. 6, 1995; accessed Jan. 18, 2017, one page.
GenBank: AAA52578.1 "GM-CSF [*Homo sapiens*]" dated Nov. 8, 1994; accessed Jan. 18, 2017, one page.
Gerich, "Insulin glargine: long-acting basal insulin analog for improved metabolic control." Curr Med Res Opin. 20(1):31-37 (Jan. 2004).
Giacometti et al., "In vitro activity of the histatin derivative P-113 against multidrug-resistant pathogens responsible for pneumonia in immunocompromised patients." 49(3):1249-52 (Mar. 2005).
Gillies et al, "Insulin Glargine" Drugs 59(2)L253-60 (Feb. 2000).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Classification of Functional Capacity and Objective Assessment, My.AmericanHeart, 1994—last accessed Oct. 23, 2015, pp. 1-2.
Clinical Trials Archive for Trial No. NCT00688701 updated Sep. 30, 2012. Accessed at: https://clinicaltrials.gov/archive/NCT00688701/2012_09_30/changes Accessed on Jun. 2, 2016, pp. 1-5 submitted.
Meier et al., "Effect of lixisenatide vs liraglutide on glycaemic control, gastric emptying and safety parameters in optimised insulin glargine type 2 diabetes mellitus +/− metformin" Poster and Abstract 926, 50th EASD Annual Meeting, Vienna, Austria Sep. 15-19, 2014, pp. 1-3.
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Final Rejection issued in U.S. Appl. No. 13/509,507; dated May 13, 2016, pp. 1-11.
Final Rejection in U.S. Appl. No. 13/633,563; dated Apr. 8, 2016, pp. 1-12.
Final Rejection in U.S. Appl. No. 13/633,496; dated Aug. 26, 2015, pp. 1-16.
Non-Final Rejection in U.S. Appl. No. 13/633,496; dated Apr. 21, 2016, pp. 1-12.
18th World Health Congress (Helsinki). WMA Declaration of Helsinki—Ethical Principles for Medical Research Involving Human Subjects; WMA; Jun. 1964, pp. 1-8.
Abbas T., et al., "Impairment of Synaptic Plasticity and Memory formation in GLP-1 Receptor Ko Mice: Interaction Between Type 2 Diabetes and Alzheimer's Disease," Behavioural Brain Research, 2009, vol. 205 (1), pp. 265-271.
Action to Control Cardiovascular Risk in Diabetes Study Group, "Effects of Intensive Glucose Lowering in Type 2 Diabetes," The New England Journal of Medicine, 2008, vol. 358 (24), pp. 2545-2559.
Actrapid® prescribing information, Apr. 2011, pp. 1-4.
Actrapid® summary of product characteristics, Apr. 2011, pp. 1-11.
Aderinwale O.G., et al., "Current Therapies and New Strategies for the Management of Alzheimer's Disease," American Journal of Alzheimer's Disease and Other Dementias, 2010, vol. 25 (5), pp. 414-424.
Agholme L., et al., "An in Vitro Model for Neuroscience: Differentiation of SH-SY5Y Cells into Cells with Morphological and Biochemical Characteristics of Mature Neurons," Journal of Alzheimer's Disease, 2010, vol. 20, pp. 1069-1082.
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Ahualli J., "The Double Duct Sign," Radiology, 2007, vol. Jul. 244 (1), pp. 314-315.

Akbar D.H., "Sub-Optimal Postprandial Blood Glucose Level in Diabetics Attending the Outpatient Clinic of a University Hospital," Saudi Med Journal, Oct. 2003, vol. 24 (10), pp. 1109-1112.
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
American Diabetes Association, "Type 2 Diabetes in Children and Adolescents," Diabetes Care, Mar. 2000, vol. 23 (3), pp. 381-389.
American Diabetes Association, "Standards of Medical Care in Diabetes—2011," Diabetes Care, Jan. 2011, vol. 34 (Suppl 1), pp. S11-S61.
Aoki K., et al., "Hydrolysis of Nonionic Surfactants," Annual Report Takeda Research Laboratory, 1968, vol. 27, pp. 172-176.
Apidra® prescribing information, Apr. 2012, pp. 1-6.
Aquiliante C.L., "Sulfonylurea Pharmacogenomics in Type 2 Diabetes: The Influence of Drug Target and Diabetes Risk Polymorphisms," Expert Review of Cardiovascular Therapy, Mar. 2010, vol. 8 (3), pp. 359-372.
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Arnolds S., et al., "Basal Insulin Glargine Vs Prandial Insulin Lispro in Type 2 Diabetes," Lancet, 2008, vol. 378 (9636), pp. 370-371.
Arnolds S., et al., "Further Improvement in Postprandial Glucose Control with Addition of Exenatide or Sitagliptin to Combination therapy with Insulin Glargine and Metformin—A Proof-of-Concept Study," Diabetes Care, 2010, vol. 33 (7), pp. 1509-1515.
Auerbach R., et al., "Angiogenesis Assays: Problems and Pitfalls," Cancer Metastasis Reviews, 2000, vol. 19 (1-2), pp. 167-172.
Bakaysa D.L., et al., "Physicochemical Basis for the Rapid Time-Action of Lysb28 Prob29-Insulin: Dissociation of a Protein-Ligand Complex," Protein science, 1996, vol. 5 (12), pp. 2521-2531.
Banks W.A., et al., "Brain Uptake of the Glucagon-Like Peptide-1 Antagonist Exendin(9-39) After intranasal Administration," The Journal of Pharmacology and Experimental Therapeutics, 2004, vol. 309 (2), pp. 469-475.
Barnett A., "Dosing of Insulin Glargine in the Treatment of Type 2 Diabetes," Clinical Therapeutics, Jun. 2007, vol. 29 (6), pp. 987-999.
Barnett A.H., et al., "Tolerability and Efficacy of Exenatide and Titrated Insulin Glargine in Adult Patients with Type 2 Diabetes Previously Uncontrolled with Metformin or a Sulfonylurea: A Multinational, Randomized, Open-Label, Two-Period, Crossover Noninferiority Trial," Clinical Therapeutics, Nov. 2007, vol. 29 (11), pp. 2333-2348.
Barnett A.H., "Insulin Glargine in the Treatment of Type 1 and Type 2 Diabetes," Vascular Health and Risk Management, Published Jan. 25, 2006, vol. 2 (1), pp. 59-67.
Barnett A.H., "Lixisenatide: Evidence for its Potential Use in the Treatment of Type 2 Diabetes," Core Evidence, Published Online Sep. 8, 2011, vol. 6, pp. 67-79.
Barnett R.O., et al., "Insulin Analogues," Lancet, 1997, vol. 349 (9044), pp. 47-51.
Behar J., et al., "Functional Gallbladder and Sphincter of Oddi Disorders," Gastroenterology, 2006, vol. 130 (5), pp. 1498-1509.
Beintema J.J., et al., "Molecular Evolution of Rodent Insulins," Molecular Biology and Evolution, 1987, vol. 4 (1), pp. 10-18.
Berger M., "Towards More Physiological Insulin Therapy in the 1990s a Comment," Diabetes Research and Clinical Practice, May 1989, vol. 6 (4), pp. S25-S31.
Berlie H., et al., "Glucagon-Like Peptide-1 Receptor Agonists as Add-On therapy to Basal Insulin in Patients with Type 2 Diabetes: A Systematic Review," Diabetes, Metabolic Syndrome and Obesity: Targets and Therapy, 2012, vol. 5, pp. 165-174.
Berlinsulin® H prescribing information, Apr. 2012, pp. 1-4.
Berlinsulin® H summary of product characteristics, Apr. 2012, pp. 1-11.
Bertram L., et al., "The Genetics of Alzheimer Disease: Back to the Future," Neuron, 2010, vol. 68 (2), pp. 270-281.
Best, Mathmatics and Statistics pp. 1-39, 1988.

(56) References Cited

OTHER PUBLICATIONS

Bethel M.A., et al., "Basal Insulin Therapy in Type 2 Diabetes," The Journal of the American Board of the Family Practice, May-Jun. 2005, vol. 18 (3), pp. 199-204.
Bhatt N.P., et al., "Chemical Pathways of Peptide Degradation. I. Deamidation of Adrenocorticotropic Hormone," Pharmaceutical Research, 1990, vol. 7 (6), pp. 593-599.
Blanchard V., et al., "Time Sequence of Maturation of Dystrophic Neurites Associated with Abeta Deposits in APP/PS1 Transgenic Mice," Experimental Neurology, 2003, vol. 184, pp. 247-263.
Bland J.M., et al., "Measurement Error," British Medical Journal, Jun. 29, 1996, vol. 312 (7047), pp. 1654.
Bolen S., et al., "Systematic Review: Comparative Effectiveness and Safety of oral Medications for Type 2 Diabetes Mellitus," Annals of Internal Medicine, Epub Jul. 16, 2007, vol. 147 (6), pp. 386-399.
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli G.B., et al., "Efficacy and Safety of Lixisenatide once Daily Vs Placebo in People with Type 2 Diabetes Insufficiently Controlled on Metformin (Getgoal-F1)," Diabetic Medicine, Published Online Oct. 24, 2014, vol. 31 (2), pp. 176-184.
Bolli G.B., "The Pharmacokinetic Basis of Insulin Therapy in Diabetes Mellitus," Diabetes Research and Clinical Practice, May 1989, vol. 6 (4), pp. S3-15.
Boutajangout A., et al., "Characterisation of Cytoskeletal Abnormalities in Mice Transgenic for Wild-Type Human Tau and Familial Alzheimer's Disease Mutants of APP and Presenilin-1," Neurobiology of Disease, 2004, vol. 15 (1), pp. 47-60.
Boutajangout A., et al., "Increased Tau Phosphorylation but Absence of formation of Neurofibrillary Tangles in Mice Double Transgenic for Human Tau and Alzheimer Mutant (M146L) Presenilin-1," Neuroscience Letters, 2002, vol. 318 (1), pp. 29-33.
Brange "Galenics of Insulin" 1987, p. 35-36.
Brange J., et al., "Chemical Stability of Insulin 3. Influence of Excipients, formulation, and Ph," Acta Pharmaceutica Nordica, 1992, vol. 4 (3), pp. 149-158.
Brange J., et al., "Design of Insulin Analogues for Meal-Related therapy," Journal of Diabetes and Its Complications, 1993, vol. 7 (2), pp. 106-112. Abstract only submitted.
Brange J., et al., "Monomeric Insulins and their Experimental and Clinical Implications," Diabetes Care, Sep. 1990, vol. 13 (9), pp. 923-954.
Brange J., et al., "Neutral Insulin Solutions Physically Stabilized by Addition of Zn2+," Diabetic Medicine, Nov.-Dec. 1986, vol. 3, pp. 532-536.
Brange J., et al., "Toward Understanding Insulin Fibrillation," Journal of Pharmaceutical Sciences, 1997, vol. 86 (5), pp. 517-525.
Brod M., et al., "Adherence Patterns in Patients with Type 2 Diabetes on Basal Insulin Analogues: Missed, Mistimed and Reduced Doses," Current Medical Research and Opinion, 2012, vol. 28 (12), pp. 1933-1946.
Brod M., et al., "Examining Correlates of Treatment Satisfaction for injectable Insulin in Type 2 Diabetes: Lessons Learned from a Clinical Trial Comparing Biphasic and Basal Analogues," Health Quality of Life Outcomes, 2007, vol. 5, pp. 1-10.
Broderick J., et al., "Guidelines for the Management of Spontaneous intracerebral Hemorrhage in Adults," Circulation, 2007, vol. 116 (16), pp. e391-e413.
Brown J.B., et al., "Slow Response to Loss of Glycemic Control in Type 2 Diabetes Mellitus," American Journal of Managed Care, 2003, vol. 9 (3), pp. 213-217.
"Buffer" Oxford Dictionary of Biochemistry and Molecular Biology, Oxford University Press, 2001, p. 83.
Burgermeister W., et al., "The Isolation of Insuin from the Pancreas," Insulin, 1975, vol. Part 2, pp. 715-727.
Burke G.T., et al., "Nature of the B10 Amino Acid Residue Requirements for High Biological Activity of Insulin," International Journal of Peptide and Protein Research, 1984, vol. 23 (4), pp. 394-401.
Buse J.B., et al., "Use of Twice-Daily Exenatide in Basal Insulin-Treated Patients with Type 2 Diabetes: A Randomized, Controlled Trial," Annals of Internal Medicine, Jan. 2011, vol. 154 (2), pp. 103-112.
Byetta—Summary of Product Characteristics, updated Jan. 27, 2015, last accessed Apr. 18, 2015, pp. 1-12.
Byrne M.M., et al., "Inhibitory Effects of Hyperglycaemia on Fed Jejunal Motility: Potential Role of Hyperinsulinaemia," European Journal of Clinical Investigation, 1998, vol. 28 (1), pp. 72-78.
Cadario B., "Sitagliptin," Drug Information Perspectives, 2010, vol. 30 (4), pp. 1-6.
Campas C., et al., "Ave-0010 GLP-1 Receptor Agonist Treatment of Diabetes," Drugs of the Future, Oct. 2008, vol. 33 (10), pp. 838-840.
Campbell R.K., et al., "Insulin Glargine," Clinical Therapeutics, 2001, vol. 23 (12), pp. 1938-1957.
Canadian Cardiovascular Society Grading of Angina Pectoris, From http://www.sscts.org/pages/Classificationanginaccs.aspx. Accessed May 27, 2016, one page.
Canadian Diabetes Association, Clinical Practice Guidelines Expert Committee, Canadian Diabetes Association 2008, Clinical Practice Guidelines for the Prevention and Management of Diabetes in Canada, Canadian Journal of Diabetes, 2008, pp. S162-S167.
Cannon P.C., et al., "Intensive versus Moderate Lipid Lowering with Statins after Acute Coronary Syndromes." New England Journal Medicine, Apr. 2004; Epub 2004 Mar. 8, 2004, vol. 350 (15), pp. 1495-1504.
Casas C., et al., "Massive CA1/2 Neuronal Loss with Intraneuronal and N-Terminal Truncated Abeta42 Accumulation in a Novel Alzheimer Transgenic Model," American Journal of Pathology, 2004, vol. 165 (4), pp. 1289-1300.
Centers for Disease Control and Prevention, National Diabetes Fact Sheet: General Information and National Estimates on Diabetes in the United States, 2003, Revolution Education Atlanta, GA: U.S. Department of Health and Human Services, Centers for Disease Control and Prevention, 2004, pp. 1-8.
Chancel, "Natixis Conference on Diabetes." Sanofi, Paris, pp. 1-23 (Nov. 8, 2011).
Charles M.A., et al., "Prevention of Type 2 Diabetes: Role of Metformin," Drugs, Sep. 1999, vol. 58 (Suppl 1), pp. 71-73.
Chatterjee S., et al., "Insulin Glargine and its Place in the Treatment of Types 1 and 2 Diabetes Mellitus," Expert Opinion on Pharmacotherapy, 2006, vol. 7 (10), pp. 1357-1371.
Chen Y.E., et al., "Tissue-Specific Expression of Unique mRNAs That Encode Proglucagon-Derived Peptides or Exendin 4 in the Lizard," The Journal of Biological Chemistry, 1997, vol. 272 (7), pp. 4108-4115.
Cheung Y.T., et al., "Effects of All-Trans-Retinoic Acid on Human SH-SY5Y Neuroblastoma as in Vitro Model in Neurotoxicity Research," Neurotoxicology, 2009, vol. 30 (1), pp. 127-135.
Chi E.Y., Excipients and their Effects on the Quality of Biologics, Available online at https://www.aaps.org/uploadedFiles/Content!Sections_and_Groups/Sections/Formulation_Design_And_Development_Section/FDDTechCornerMay2012.pdf, 9 pages (2012.
Childs B.P., et al., "Defining and Reporting Hypoglycemia in Diabetes: A Report from the American Diabetes Association Workgroup on Hypoglycemia," Diabetes Care, May 2005, vol. 28 (5), pp. 1245-1249.
Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Christensen M., et al., "Lixisenatide, A Novel GLP-1 Receptor Agonist for the Treatment of Type 2 Diabetes Mellitus," IDrugs: The Investigational Drugs Journal, Aug. 2009, vol. 12 (8), pp. 503-513.
Christensen M., et al., "Lixisenatide for Type 2 Diabetes Mellitus," Expert Opinion on Investigational Drugs, Epub Mar. 11, 2011, vol. 20 (4), pp. 549-557.

(56) References Cited

OTHER PUBLICATIONS

Clinical Trials History for Trial No. NCT00688701 last updated Mar. 25, 2014. Accessed at https://clinicaltrials.gov/archive/NCT00688701 Accessed on Jun. 2, 2016, pp. 1-2 submitted.
Cochran E., et al., "The Use of U-500 in Patients with Extreme Insulin Resistance," Diabetes Care, 2005, vol. 28 (5), pp. 1240-1244.
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino E., et al., "Therapy with Insulin Glargine (Lantus) in toddlers, Children and Adolescents with Type 1 Diabetes," Diabetes Research and Clinical Practice, 2005, vol. 70 (1), pp. 1-7.
Brange & Langkjaer, "Insulin Structure and Stability" Chapter 11; Pharm Biotechnol 5:315-50 (1993).
Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Crapo P.A., et al., "Postprandial Plasma-Glucose and -Insulin Responses to Different Complex Carbohydrates," Diabetes, Dec. 1977, vol. 26 (12), pp. 1178-1183.
Croom K.F., et al., "Liraglutide a Review of its Use in Type 2 Diabetes Mellitus," Drugs, 2009, vol. 69 (14), pp. 1985-2004.
Cryer P.E., "Hypoglycemia is the Limiting Factor in the Management of Diabetes," Diabetes/Metabolism Research and Reviews, Jan.-Feb. 1999, vol. 15 (1), pp. 42-46.
Cvetkovic R.S., et al., "Exenatide A Review of its Use in Patients with Type 2 Diabetes Mellitus (As an Adjunct to Metformin and/or A Sulfonylurea)," Drugs, 2007, vol. 67 (6), pp. 935-954.
Czech C., et al., "Proteolytical Processing of Mutated Human Amyloid Precursor Protein in Transgenic Mice," Brain Research Molecular Brain Research, 1997, vol. 47 (1-2), pp. 108-116.
D'Alessio D., "GLP-1 Receptor Agonists: Strategies for PPG Control," Medical Nursing Education, Jan. 2011, vol. 3, pp. 1-26.
D'Alessio D.A., et al., "Glucagon-Like Peptide 1 Enhances Glucose tolerance both by Stimulation of Insulin Release and by increasing Insulin-Independent Glucose Disposal," Journal of Clinical Investigation, 1994, vol. 93 (5), pp. 2263-2266.
Das., et al., "The British Cardiac Society Working Group Definition of Myocardial Infarction: Implications for Practice," Heart, 2005, vol. 92 (1), pp. 21-26, Jan. 2006; Epub Apr. 14, 2005.
Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
De Arriba S.G., et al., "Carbonyl Stress and Nmda Receptor Activation Contribute to Methylglyoxal Neurotoxicity," Free Radical Biology and Medicine, 2006, vol. 40 (5), pp. 779-790.
De La Pena A., et al., "Pharmacokinetics and Pharmacodynamics of High-Dose Human Regular U-500 Insulin Versus Human Regular U-100 Insulin in Healthy Obese Subjects," Diabetes Care, 2011, vol. 34 (12), pp. 2496-2501.
De Rosa R., et al., "Intranasal Administration of Nerve Growth Factor (Ngf) Rescues Recognition Memory Deficits in Ad11 Anti-Ngf Transgenic Mice," Proceedings of the National Academy of Sciences of the United States of America, 2005, vol. 102 (10), pp. 3811-3816.
Deacon C.F., et al., "Dipeptidyl Peptidase IV inhibition Potentiates the Insulinotropic Effect of Glucagon-Like Peptide 1 in the Anesthetized Pig," Diabetes, 1998, vol. 47 (5), pp. 764-769.

Deacon C.F., et al., "Dipeptidyl Peptidase IV Resistant Analogues of Glucagon-Like Peptide-1 Which have Extended Metabolic Stability and Improved Biological Activity," Diabetologia, 1998, vol. 41 (3), pp. 271-278.
Definition of indication, Merriam-Webster online, accessed Oct. 22, 2015, 2 pages.
Definition of palliative, http://medicaldictionary.thefreedictionary.com/, accessed on Nov. 6, 2014, pp. 1-2.
Definition of Phase, Clinical Trials.gov NIH, accessed, Mar. 2016, one page.
Definition of sphincter of pancreatic duct in the Medical Dictionary, http://medicaldictionary.thefreedictionary.com/, accessed on May 22, 2014, pp. 1-2.
Defronzo R.A., et al., "Effects of Exenatide (Exendin-4) on Glycemic Control and Weight Over 30 Weeks in Metformin-Treated Patients with Type 2 Diabetes," Diabetes care, May 2005, vol. 28 (5), pp. 1092-1100.
Defronzo R.A., "Pathogenesis of Type 2 Diabetes: Implications for Metformin," Drugs, Sep. 1999, vol. 58 (Suppl 1), pp. 29-30.
Defronzo R.A., "Pharmacologic therapy for Type 2 Diabetes Mellitus," Annals of Internal Medicine, 1999, vol. 131 (4), pp. 281-303.
Delatour B., et al., "Alzheimer Pathology Disorganizes Cortico-Cortical Circuitry: Direct Evidence from a Transgenic Animal Model," Neurobiology of Disease, 2004, vol. 16 (1), pp. 41-47.
Devries J.H., et al., "Sequential intensification of Metformin Treatment in Type 2 Diabetes with Liraglutide Followed by Randomized Addition of Basal Insulin Prompted by A1C Targets," Diabetes Care, 2012, vol. 35 (7), pp. 1446-1454.
Dewitt D.E., "Case Study: Treating New on-Set Catabolic Type 2 Diabetes with Glargine and Lispro," Clinical Diabetes, Oct. 2006, vol. 24 (4), pp. 180-181.
Diabetes Control and Complications Trial/ Epidemiology of Diabetes Interventions and Complications Research Group, "Intensive Diabetes Treatment and Cardiovascular Disease in Patients with Type 1 Diabetes," New England Journal Medicine, Dec. 2005, vol. 353 (25), pp. 2643-2259.
Diabetes Control and Complications Trial, "Intensive diabetes therapy and carotid intima-media thickness in type 1 diabetes," New England Journal Medicine Jun. 2003, vol. 348 (23), pp. 2294-2303.
Diabetes Prevention Program Research Group, "Reduction in the incidence of Type 2 Diabetes with Lifestyle intervention or Metformin," The New England Journal of Medicine, 2002, vol. 346 (6), pp. 393-403.
Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dixon G.H., et al., "Regeneration of Insulin Activity from the Separated and inactive A and B Chains," Nature, 1960, vol. 188 (4752), pp. 721-724.
Donelli G., et al., "Plastic Biliary Stent Occlusion: Factors Involved and Possible Preventive Approaches," Clinical Medicine & Research, 2007, vol. 5 (1), pp. 53-60.
Dormandy J.A., et al., "Secondary Prevention of Macrovascular Events in Patients with Type 2 Diabetes in the Proactive Study (Prospective Pioglitazone Clinical Trial in Macrovascular Events): A Randomised Controlled Trial," Lancet, Oct. 8, 2005, vol. 366 (9493), pp. 1279-1289.
Doyle M.E. et al., "Mechanisms of Action of Glucagon-Like Peptide 1 in the Pancreas," Pharmacology & Therapeutics, Mar. 2007, vol. 113 (3), pp. 546-593.
Drucker D.J. et al., "the incretin System: Glucagon-Like Peptide-1 Receptor Agonists and Dipeptidyl Peptidase-4 inhibitors in Type 2 Diabetes," Lancet, Nov. 11, 2006, vol. 368 (9548), pp. 1696-1705.
Drucker D.J., "Glucagon-Like Peptides," Diabetes, 1998, vol. 47 (2), pp. 159-169.
Drucker D.J., "Mini Review: The Glucagon-Like Peptides," Endocrinology, 2001, vol. 142 (2), pp. 521-527.
Drucker D.J., "The Biology of Incretin Hormones," Cell Metabolism, 2006, vol. 3 (3), pp. 153-165.
Druet C., et al., "Characterization of Insulin Secretion and Resistance in Type 2 Diabetes of Adolescents," The Journal of Clinical Endocrinology & Metabolism, Feb. 2006, vol. 91 (2), pp. 401-404 (Epub Nov. 15, 2005).

(56) References Cited

OTHER PUBLICATIONS

DrugBank, "Insulin glargine," available online at http://www.drugbank.ca/drugs/DB00047, 16 pages (accessed online Sep. 25, 2014).
Drury P.L., et al., "Diabetic Nephropathy," British Medical Bulletin, 1989, vol. 45 (1), pp. 127-147.
Dubois B., et al., "Revising the Definition of Alzheimer's Disease: A New Lexicon," Lancet Neurology, 2010, vol. 9 (11), pp. 1118-1127.
Dunn C.J., et al., "Insulin Glargine: An Updated Review of its Use in the Management of Diabetes Mellitus," Drugs, 2003, vol. 63 (16), pp. 1743-1778.
During M.J., et al., "Glucagon-Like Peptide-1 Receptor is involved in Learning and Neuroprotection," Nature Medicine, 2003, vol. 9 (9), pp. 1173-1179.
Eckert A., et al., "Alzheimer's Disease-Like Alterations in Peripheral Cells from Presenilin-1 Transgenic Mice," Neurobiology of Disease, 2001, vol. 8 (2), pp. 331-342.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6017; Clinical Trial Eudra CT No. 2007-005884-92, accessed Apr. 24, 2015, one page.
EFC6018; Clinical trial EudraCT 2007-005887-29, "GETGOAL-MONO" accessed Jul. 27, 2014; pp. 1-16.
EMA—Science Medicines Health "TOUJEO" EPAR Summary for the Public, first published Nov. 5, 2009, pp. 1-3.
EMA—European Medicines Agency, "Note for guidance on non-clinical safety studies for the conduct of human clinical Trials and marketing authorization for pharmaceuticals," Jul. 2008, pp. 1-22.
EMA Press Release, "European Medicines Agency recommends suspension of Avandia, Avandamet and Avaglim" pp. 1-2 (Sep. 23, 2010).
Eng J., et al., "Isolation and Characterization of Exendin-4, an Exendin-3 Analogue, from Heloderma Suspectum Venom Further Evidence for an Exendin Receptor on Dispersed Acini from Guinea Pig Pancreas," The Journal of Biological Chemistry, 1992, vol. 267 (11), pp. 7402-7405.
English translation of Search Report for Chinese Patent Application No. 201280053404.6; dated Feb. 10, 2015, pp. 1-3.
English translation of Search Report for Chinese Patent Application No. 20140220537.9; dated Feb. 13, 2015, pp. 1-2.
English translation of the TIPO Search Report for ROC Patent Application No. 104116749, dated Feb. 22, 2016, One page.
English translation of the TIPO Search Report for ROC Patent Application No. 101131466; dated Mar. 2, 2016, one pag.
English Translation of TIPO Search Report for ROC Patent Application No. 101130936, dated Dec. 1, 2015, one page.
European Medicines Agency—Science Medicines Health, "Guideline on clinical investigation of medicinal products in the treatment of diabetes mellitus" Committee for Medicinal Products for Human Use, Jan. 20, 2010, pp. 1-19.
European Medicines Agency, Committee for Medicinal Products for Human Use (CHMP), "Assessment Report—Lyxumia", Nov. 28, 2012, pp. 1-81.
European Medicines Agency, "Toujeo (previously Optisulin) insulin glargine," <http:index.jsp?curl="pages/medicines/human/medicines/000309/human_med_000955.jsp&mid=WCOb01ac058001d124" >, last updated Jan. 25, 2016, visited Feb. 3, 2016, pp. 1-6—screenshot of "About" tab of webpage and printouts f "About" tab of webpage with listed items collapsed and expanded.</http:>.
European Public Assessment Report (EPAR) Optisulin EPAR Summary for the Public. Feb. 2009, pp. 1-3.

Ex Parte Herrmann, Appeal No. 2009-001777 U.S. Appl. No. 10/616,457 (B. Pai. Nov. 13, 2009).
Executive Summary, "Standards of Medical Care in Diabetes—2009" Diabetes Care,32(Suppl. 1):S6-S12 (Jan. 2009).
Extended European Search Report for Euorpean Application No. 98 11 0889.7; dated Oct. 14, 1998, pp. 1-4.
Extended European Search Report for European Application No. 09 17 5876.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 6, 2011, pp. 1-12.
Extended European Search Report for European Application No. 11 16 0270.2; dated Sep. 19, 2011, pp. 1-8.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 305 126; dated Apr. 11, 2013, pp. 1-7.
Extended European Search Report for European Application No. 13 305 432.0; dated Sep. 13, 2013, pp. 1-5.
Extended European Search Report for European Application No. 14 16 6877.2; dated Aug. 18, 2014, pp. 1-6.
Extended European Search Report for European Application No. 14 19 7154.9: dated Apr. 8, 2015, pp. 1-7.
Extended European Search Report for European Application No. 15159064.3, dated Oct. 19, 2015, pp. 1-4.
Fabunmi R., et al., "Patient Characteristics, Drug Adherence Patterns, and Hypoglycemia Costs for Patients with Type 2 Diabetes Mellitus Newly initiated on Exenatide or Insulin Glargine," Current Medical Research and Opinion, 2009, vol. 25 (3), pp. 777-786.
Faivre E., et al., "Effects of Gip Analogues in Neuronal Signalling, Cell Proliferation and Learning and Memory," Regulatory Peptides, Aug. 2010, vol. 164 (1), pp. 40-41.
FDA—Food and Drug Administration, CFR—Code of Federal Regulations Title 21, Chapter 1, Subchapter D, Part 312.21, "Phases of an investigation," Apr. 1, 2015, pp. 1-2.
FDA Frequently Asked Questions about Combination Products;accessed from www.fda.gov/CombinationProducts/AboutCombinationProducts/usm101496.1/htm, 2009 downloaded Jul. 13, 2012, pp. 1-18.
FDA Guidance for Industry, US Department of Health and Human Services, Food and Drug Administration, Center for Drug Evaluation and Research (CDER), pp. 1-11, Feb. 2014.
FDA label of Apidra®, May 2014, pp. 1-35.
FDA label of Humalog®, Mar. 2013, pp. 1-27.
FDA label of Lantus®, Oct. 2013, pp. 1-44.
Feinglos M.N., et al., "Effects of Liraglutide (Nn2211), a Long-Acting GLP-1 Analogue, on Glycaemic Control and Bodyweight in Subjects with Type 2 Diabetes," Diabetic Medicine, Jul. 2005, vol. 22 (8), pp. 1016-1023.
Fieller E.C., "Symposium on Interval Estimation; Some Problems with Interval Estimation," Journal of the Royal Statistical Society, 1954, vol. 16 (2), pp. 175-185.
Final Office Action from U.S. Appl. No. 12/617,805; dated Feb. 11, 2013, pp. 1-13.
Final Office Action from U.S. Appl. No. 12/617,805; dated Jan. 12, 2012, pp. 1-14.
Final Office Action from U.S. Appl. No. 12/617,805; dated Jan. 13, 2015, pp. 1-11.
Final Office Action issued in U.S. Appl. No. 13/123,835; dated Feb. 12, 2013, pp. 1-13.
Final Office Action issued in U.S. Appl. No. 13/602,913; dated Apr. 2, 2015, pp. 1-7.
Final Office Action issued in U.S. Appl. No. 13/602,913; dated Jun. 20, 2014, pp. 1-27.
Final Office Action issued in U.S. Appl. No. 13/602,913; dated Sep. 13, 2013, pp. 1-11.

(56) References Cited

OTHER PUBLICATIONS

Final Office Action issued in U.S. Appl. No. 12/617,805; dated May 25, 2016, pp. 1-9.
Final Office Actionissued in U.S. Appl. No. 13/382,442; dated Aug. 11, 2015, pp. 1-35.
Final Rejection in U.S. Appl. No. 13/633,496; dated Nov. 18, 2014, pp. 1-11.
Final Rejection in U.S. Appl. No. 13/633,496; dated Nov. 4, 2013, pp. 1-7.
Final Rejection in U.S. Appl. No. 13/633,563; dated Apr. 22, 2015, pp. 1-12.
Final Rejection in U.S. Appl. No. 13/633,563; dated Dec. 16, 2013, pp. 1-58.
Final Rejection issued in U.S. Appl. 14/172,151; dated Jul. 20, 2015, pp. 1-18.
Final Rejection issued in U.S. Appl. No. 12/617,811; dated Jan. 4, 2013, pp. 1-6.
Final Rejection issued in U.S. Appl. No. 12/617,811; dated Jul. 31, 2015, pp. 1-15.
Final Rejection issued in U.S. Appl. No. 13/110,568; dated Feb. 21, 2013, pp. 1-20.
Final Rejection issued in U.S. Appl. No. 13/310,118; dated Aug. 2, 2012, pp. 1-20.
Final Rejection issued in U.S. Appl. No. 13/363,956; dated May 20, 2014, pp. 1-16.
Final Rejection issued in U.S. Appl. No. 13/382,442; dated Jul. 17, 2013, pp. 1-30.
Final Rejection issued in U.S. Appl. No. 13/382,442; dated Jun. 13, 2014, pp. 1-29.
Final Rejection issued in U.S. Appl. No. 13/382,772; dated Jun. 3, 2014, pp. 1-34.
Final Rejection issued in U.S. Appl. No. 13/382,772; dated Feb. 10, 2015, pp. 1-36.
Final Rejection issued in U.S. Appl. No. 13/467,707; dated Feb. 12, 2016, pp. 1-12.
Final Rejection issued in U.S. Appl. No. 13/467,707; dated Feb. 25, 2014, pp. 1-18.
Final Rejection issued in U.S. Appl. No. 13/467,707; dated Jan. 7, 2015, pp. 1-8.
Final Rejection issued in U.S. Appl. No. 13/468,422; dated Jan. 6, 2014, pp. 1-21.
Final Rejection issued in U.S. Appl. No. 13/468,422; dated Jan. 23, 2015, pp. 1-27.
Final Rejection issued in U.S. Appl. No. 13/469,633; dated Dec. 4, 2013, pp. 1-17.
Final Rejection issued in U.S. Appl. No. 13/469,633; dated Jan. 23, 2015, pp. 1-12.
Final Rejection issued in U.S. Appl. No. 13/509,507; dated Jul. 23, 2015, pp. 1-11.
Final Rejection issued in U.S. Appl. No. 13/509,542; dated Nov. 21, 2013, pp. 1-34.
Final Rejection issued in U.S. Appl. No. 13/509,542; dated Jan. 28, 2015, pp. 1-26.
Final Rejection issued in U.S. Appl. No. 13/595,590; dated Apr. 2, 2014, pp. 1-7.
Final Rejection issued in U.S. Appl. No. 13/595,590; dated Dec. 19, 2014, pp. 1-14.
Final Rejection issued in U.S. Appl. No. 13/661,476, dated Oct. 2, 2014, pp. 1-33.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Final Rejection issued in U.S. Appl. No. 13/700,631; dated Apr. 13, 2015, pp. 1-19.
Final Rejection issued in U.S. Appl. No. 13/700,631; dated Jun. 18, 2014, pp. 1-25.
Final Rejection issued in U.S. Appl. No. 13/819,114; dated Mar. 2, 2015, pp. 1-10.
Final Rejection issued in U.S. Appl. No. 13/382,772; dated Feb. 24, 2016, pp. 1-36.
Final Rejection issued in U.S. Appl. No. 14/303,895; dated Apr. 27, 2015, pp. 1-10.
Final-Rejection issued in U.S. Appl. No. 13/432,811; dated Dec. 12, 2014, pp. 1-8.
Final-Rejection issued in U.S. Appl. No. 13/432,811; dated Mar. 31, 2015, pp. 1-9.
Final-Rejection issued in U.S. Appl. No. 13/432,811; dated Sep. 6, 2014, pp. 1-8.
Final Rejection issued in U.S. Appl. No. 13/509,542, dated Feb. 10, 2016, pp. 1-40.
Final-Rejection issued in U.S. Appl. No. 13/432,811; dated Feb. 10, 2016, pp. 1-9.
Fonseca V.A., et al., "Efficacy and Safety of the once-Daily GLP-1 Receptor Agonist Lixisenatide in Monotherapy: A Randomized, Double-Blind, Placebo-Controlled Trial in Patients with Type 2 Diabetes (Getgoal-Mono)," Diabetes Care, 2012, vol. 35 (6), pp. 1225-1231.
Forman J.P., et al., "Higher Levels of Albuminuria within the Normal Range Predict Incident Hypertension." Journal of American Social Nephrology, Oct. 2008, vol. 19 (10), pp. 1983-1988.
Fox J.D., et al., "Single Amino Acid Substitutions on the Surface of *Escherichia coli* Maltose-Binding Protein can have a Profound Impact on the Solubility of Fusion Proteins," Protein Science, 2001, vol. 10 (3), pp. 622-630.
Fransson J., et al., "Oxidation of Human Insulin-Like Growth Factor I in formulation Studies: Kinetics of Methionine Oxidation in Aqueous Solution and in Solid State," Pharmaceutical Research, Aug. 1996, vol. 13 (8), pp. 1252-1257.
Galloway J.A., et al., "New forms of Insulin," Diabetes, 1972, vol. 21 (2 Suppl), pp. 637-648.
Gallwitz B., "Liraglutide. GLP-1 Receptor Agonist Treatment of Type 2 Diabetes Treatment of Obesity," Drugs of the Future, Jan. 2008, vol. 33 (1), pp. 13-20.
Gandhi S., et al., "Molecular Pathogenesis of Parkinson's Disease," Human Molecular Genetics, 2005, vol. 14 (18), pp. 2749-2755.
Garber A., et al., "Liraglutide Versus Glimepiride Monotherapy for Type 2 Diabetes (Lead-3 Mono): A Randomised, 52-Week, Phase III, Double-Blind, Parallel-Treatment Trial," The Lancet, Feb. 7, 2009, vol. 373 (9662), pp. 473-481.
Garg R., et al., "U-500 Insulin: Why, When and How to Use in Clinical Practice," Diabetes/Metabolism Research and Reviews, 2007, vol. 23 (4), pp. 265-268.
Garriques L.N., et al., "The Effect of Mutations on the Structure of Insulin Fibrils Studied by Fourier Transform infrared (FTIR) Spectroscopy and Electron Microscopy," Journal of Pharmaceutical Sciences, 2002, vol. 91 (12), pp. 2473-2480.
Gault V.A., et al., "GLP-1 Agonists Facilitate Hippocampal Ltp and Reverse the Impairment of LTP induced by Beta-Amyloid," European Journal of Pharmacology, Jun. 10, 2008; published online Mar. 29, 2008, vol. 587 (1-3), pp. 112-117.
Gavin J.R., "Report of the Expert Committee on the Diagnosis and Classification of Diabetes Mellitus," Diabetes Care, Jul. 1997, vol. 20 (7), pp. 1183-1197.
Geiger R., "The Chemistry of Insulin," Chemiker Zeitung, Jan. 1976, vol. 100 (3), pp. 54-56.
Gengler S., et al., "Val(8)GLP-1 Rescues Synaptic Plasticity and Reduces Dense Core Plaques in APP/PS1 Mice," Neurobiology of Aging, 2012, vol. 33 (2), pp. 265-276.
Gerich et al., "Monotherapy with GLP-1 receptor agonist, Lixisenatide, significantly improves glycaemic control in type 2 diabetic patients," Diabetologia 53(Supplement 1)p. S330, Abstract 830, Presented at 46th Annual Meeting of EASD, Stockholm, Sweden, p. 1 (Sep. 2010).
Giugliano D., et al., "Treatment Regimens with Insulin Analogues and Haemoglobin A1C Target of <7% in Type 2 Diabetes: A Systematic Review," Diabetes Research and Clinical Practice, 2010, vol. 92 (1), pp. 1-10.
Goke R., et al., "Distribution of GLP-1 Binding Sites in the Rat Brain: Evidence That Exendin-4 is a Ligand of Brain GLP-1 Binding Sites," European Journal of Neuroscience, 1995, vol. 7 (11), pp. 2294-2300.

(56) References Cited

OTHER PUBLICATIONS

Goke R., et al., "Exendin-4 is a High Potency Agonist and Truncated Exendin-(9-39)-Amide an Antagonist at the Glucagon-Like Peptide 1-(7-36)-Amide Receptor of Insulin-Secreting Beta-Cells," The Journal of Biological Chemistry, 1993, vol. 268 (26), pp. 19650-19655.

Goldstein D.E., et al., "Tests of Glycemia in Diabetes," Diabetes Care, Jun. 1995, vol. 18 (6), pp. 896-909.

Gough K., et al., "Assessment of Dose Proportionality: Report from the Statisticians in the Pharmaceutical Industry/ Pharmacokinetics UK Joint Working Party," Drug Information Journal, 1995, vol. 29, pp. 1039-1048.

Goykhman S., et al., "Insulin Glargine: A Review 8 Years After its introduction," Expert Opinion on Pharmacotherapy, 2009, vol. 10 (4), pp. 705-718.

Greig N.H., et al., "Once Daily Injection of Exendin-4 to Diabetic Mice Achieves Long-Term Beneficial Effects on Blood Glucose Concentrations," Diabetologia, 1999, vol. 42 (1), pp. 45-50.

Gura T., "Systems for Identifying New Drugs Are often Faulty," Science, 1997, vol. 278 (5340), pp. 1041-1042.

Gutniak M., et al., "Antidiabetogenic Effect of Glucagon-Like Peptide-1 (7-36) Amide in Normal Subjects and Patients with Diabetes Mellitus," The New England Journal of Medicine, 1992, vol. 326 (20), pp. 1316-1322.

Gygi S.P., et al, "Quantitative Analysis of Complex Protein Mixtures Using Isotope-Coded Affinity Tags," Nature Biotechnology, Oct. 1999, vol. 17 (10), pp. 994-999.

Hamilton A., et al., "Novel GLP-1 Mimetics Developed to Treat Type 2 Diabetes Promote Progenitor Cell Proliferation in the Brain," Journal of Neuroscience Research, 2011, vol. 89 (4), pp. 481-489.

Hamilton A., et al., "Receptors for the incretin Glucagon-Like Peptide-1 are Expressed on Neurons in the Central Nervous System," NeuroReport, 2009, vol. 20 (13), pp. 1161-1166.

Hanas R., et al., "2010 Consensus Statement on the Worldwide Standardization of the Hemoglobin A1C Measurement," Diabetes Care, Aug. 2010, vol. 33 (8), pp. 1903-1904.

Hanefeld M., et al., "The Postprandial State and the Risk of Atherosclerosis," Diabetic Medicine, 1997, vol. 14 (Suppl 3), pp. S6-S11.

Hanefeld M., "Normnahe Postprandiale Hyperglykamie-Eine Essenzielle Komponente Guter Diabeteskontrolle Und Pravention Kardiovaskularer Erkrankungen (Near-Normal Postprandial Hyperglycemia—An Essential Component of Good Diabetes Control and Prevention of Cardiovascular Diseases)," Paul Langerhans Lecture Diabetologie und Stoffwechsel, 2007, vol. 2, pp. 362-369, in German with English abstract.

Hanna et al., "Canadian Diabetes Association Clinical Practice Guidelines Expert Committee Pharmacologic Management of Type 2 Diabetes," Canadian Journal of Diabetes, Dec. 2003, vol. 27 (Supp 2), pp. S37-S42.

Harkavyi A., et al., "Glucagon-Like Peptide I Receptor Stimulation Reverses Key Deficits in Distinct Rodent Models of Parkinson's Disease," Journal of Neuroinflammation, 2008, vol. 5 (19), pp. 1-9.

Harris S.B., et al., "Clinical inertia in Patients with T2Dm Requiring Insulin in Family Practice," Canadian Family Physician, 2010, vol. 56 (12), pp. e418-e424.

Hartmann H., et al., "Biological Activity of Des-(B26-B30)-Insulinamide and Related Analogues in Rat Hepatocyte Cultures," Diabetologia, 1989, vol. 32 (7), pp. 416-420.

Heinrich G., et al., "Pre-Proglucagon Messenger Ribonucleic Acid: Nucleotide and Encoded Amino Acid Sequences of the Rat Pancreatic Complementary Deoxyribonucleic Acid," Endocrinology, 1984, vol. 115 (6), pp. 2176-2181.

Hellstrom M., et al., "T1388 GTP-010 as a Therapetuic tool in IBS Pain Relief: Prospective, Randomized, Palebo-Controlled Study of a GLP-1 Analog," Gastroenterology, Apr. 2008, vol. 134 (4), pp. A-544.

Higgins G.C., et al., "Oxidative Stress: Emerging Mitochondrial and Cellular themes and Variations in Neuronal Injury," Journal of Alzheimer's Disease, 2010, vol. 20, pp. S453-S473.

Himeno T., et al., "Beneficial Effects of Exendin-4 on Experimental Polyneuropathy in Diabetic Mice," Diabetes, 2011, vol. 60 (9), pp. 2397-2406.

Hinds K., et al., "Synthesis and Characterization of Poly(Ethylene Glycol)-Insulin Conjugates," Bioconjugate Chemistry, Mar.-Apr. 2000, vol. 11 (2), pp. 195-201.

Hinnen D.A., "Therapeutic Options for the Management of Postprandial Glucose in Patients With Type 2 Diabetes on Basal Insulin," Clinical Diabetes, 2015, vol. 33 (4), pp. 175-180.

Hoe 901/2004 Study Investigators Group, "Safety and Efficacy of Insulin Glargine (Hoe 901) Versus NPH Insulin in Combination with oral Treatment in Type 2 Diabetic Patients," Diabetic Medicine, 2003, vol. 20, pp. 545-551.

Holman R.R., et al., "10-Year Follow-Up of intensive Glucose Control in Type 2 Diabetes," The New England Journal of Medicine, 2008, vol. 359 (15), pp. 1577-1589.

Holscher C., "Development of Beta-Amyloid-induced Neurodegeneration in Alzheimer's Disease and Novel Neuroprotective Strategies," Reviews in the Neurosciences, 2005, vol. 16 (3), pp. 181-212.

Holscher C., et al., "New Roles for Insulin-Like Hormones in Neuronal Signalling and Protection: New Hopes for Novel Treatments of Alzheimer's Disease?," Neurobiology of Aging, 2008, vol. 31 (9), pp. 1495-1502.

Holscher C., "Incretin Analogues that have been Developed to Treat Type 2 Diabetes Hold Promise as a Novel Treatment Strategy for Alzheimer's Disease," Recent Patents on Cns Drug Discovery, 2010, vol. 5 (2), pp. 109-117.

Holscher C., "Possible Causes of Alzheimer's Disease: Amyloid Fragments, Free Radical, and Calcium Homeostasis," Neurobiology of Disease, 1998, vol. 5 (3), pp. 129-141.

Holscher C., "The Role of GLP-1 in Neuronal Activity and Neurodegeneration," Vitamins and Hormones, 2010, vol. 84, pp. 331-354.

Holst J.J., et al., "Combining GLP-1 Receptor Agonists with Insulin: therapeutic Rationales and Clinical Findings," Diabetes, Obesity and Metabolism, 2013, vol. 15 (1), pp. 3-14.

Holst J.J., "Glucagon-Like Peptide-1, a Gastrointestinal Hormone with a Pharmaceutical Potential," Current Medicinal Chemistry, 1999, vol. 6 (11), pp. 1005-1017.

Home P.D., et al., "Insulin Treatment: A Decade of Change," British Medical Bulletin, 1989, vol. 45 (1), pp. 92-110.

http://diabetes.emedtv.com/lantus/generic-lantus.html; one page, last accessed Dec. 23, 2015.

Humalog® prescribing information, Apr. 2012, pp. 1-6.

Hunter K., et al., "Drugs Developed to Treat Diabetes, Liraglutide and Lixisenatide, Cross the Blood Brain Barrier and Enhance Neurogenesis," BMC Neuroscience, 2012, vol. 13, pp. 1-6.

IDF Clinical Guidelines Task Force, Global Guideline for Type 2 Diabetes, Brussels: International Diabetes Federation, Aug. 2005, pp. 1-82.

IDF, International Diabetes Federation Guideline Development Group, "Guideline for management of postmeal glucose in diabetes," Diabetes Research Clinical Practice, 2012, pp. 1-13.

INPHARMA, Product News. "AVE0010 set to deliver in type 2 diabetes mellitus," Database Adisnews, retrieved from STN, Jun. 2008, pp. 1-3.

"Insulin Aspart Injection." Formulated Preparations: Specific Monographs. British Pharmacopoeia 3. pp. 1-3 (2012).

International Search Report by the ISA for International Application No. PCT/EP2007/005932; dated Oct. 9, 2007, pp. 1-6.

International Search Report by the ISA for International Application No. PCT/EP2009/000017; dated Jun. 22, 2009, pp. 1-7.

International Search Report by the ISA for International Application No. PCT/EP2009/063195; dated May 6, 2010.

International Search Report by the ISA for International Application No. PCT/EP2010/059436; dated Jun. 17, 2011, pp. 1-5.

International Search Report by the ISA for International Application No. PCT/EP2010/059438; dated Oct. 4, 2010, pp. 1-3.

International Search Report by the ISA for International Application No. PCT/EP2010/062638; dated Mar. 18, 2011, pp. 1-5.

(56) References Cited

OTHER PUBLICATIONS

International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-16.
International Search Report by the ISA for International Application No. PCT/EP2012/055660; dated May 10, 2012, pp. 1-6.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/069485; dated Dec. 11, 2012, pp. 1-5.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4.
International Search Report by the ISA for International Application No. PCT/EP2015/079285; dated Mar. 9, 2016, pp. 1-7.
Inzucchi S.E., et al., "Management of Hyperglycemia in Type 2 Diabetes: A Patient-Centered Approach," Diabetes Care, Jun. 2012, vol. 35, pp. 1364-1379.
Isacson R., et al., "The Glucagon-Like Peptide 1 Receptor Agonist Exendin-4 improves Reference Memory Performance and Decreases Immobility in the forced Swim Test," European Journal of Pharmacology, 2009, vol. 650 (1), pp. 249-255.
ISPAD, International Diabetes Federation; "Global/IDF/ISPAD Guideline for Diabetes in Childhood and Adolescence," pp. 1-132 (2011).
Jackson R.L., et al., "Neutral Regular Insulin," Diabetes, 1972, vol. 21 (4), pp. 235-245.
Jain R.K., "Barriers to Drug Delivery in Solid Tumors," Scientific American, Jul. 1994, vol. 271 (1), pp. 58-65.
Jang J.H., et al., "Neuroprotective Effects of Triticum Aestivum L. Against B-Amyloid-induced Cell Death and Memory Impairments," Phytotherapy Research, 2010, vol. 24 (1), pp. 76-84.
Jekel P.A., et al., "Use of Endoproteinase Lys-C from Lysobacter Enzymogenes in Protein Sequence Analysis," Analytical Biochemistry, 1983, vol. 134 (2), pp. 347-354.
Jendle J., et al., "Insulin and GLP-1 Analog Combinations in Type 2 Diabetes Mellitus: A Critical Review," Expert Opinion on Investigational Drugs, 2012, vol. 21 (10), pp. 1463-1474.
Jimenez S., et al., "Inflammatory Response in the Hippocampus of PS1M146L/App751SL Mouse Model of Alzheimer'S Disease: Age-Dependent Switch in the Microglial Phenotype from Alternative to Classic," The Journal of Neuroscience, 2008, vol. 28 (45), pp. 11650-11661.
Johnson et al., "When is a unit of insulin not a unit of insulin? Detemir dosing in type 2 diabetes" Poster, one page, 2008. http://professional.diabetes.org/ContenUPosters/2008/p8-LB.pdf.

Johnson P.J., et al., "Diabetes, Insulin Resistance, and Metabolic Syndrome in Horses," Journal of Diabetes Science and Technology, May 2012, vol. 6 (3), pp. 534-540.
Jones K.L., et al., "Effect of Metformin in Pediatric Patients with Type 2 Diabetes: A Randomized Controlled Trial," Diabetes Care, Jan. 2002, vol. 25 (1), pp. 89-94.
Jorgensen K.H., et al., "Five Fold Increase of Insulin Concentration Delays the Absorption of Subcutaneously Injected Human Insulin Suspensions in Pigs," Diabetes Research and Clinical Practice, 2000, vol. 50, pp. 161-167.
Kaarsholm N.C., et al., "Engineering Stability of the Insulin Monomer Fold with Application to Structure-Activity Relationships," Biochemistry, 1993, vol. 32 (40), pp. 10773-10778.
Kadima W., "Role of Metal Ions in the T- to R-Allosteric Transition in the Insulin Hexamer," Biochemistry, Oct. 1999, vol. 38 (41), pp. 13443-13452.
Kaduszkiewicz H., et al., "Cholinesterase inhibitors for Patients with Alzheimer's Disease: Systematic Review of Randomised Clinical Trials," British Medical Journal (Clinical Research ed.), 2005, vol. 331 (7512), pp. 321-327.
Kaech S., et al., "Culturing Hippocampal Neurons," Nature Protocols, 2006, vol. 1 (5), pp. 2406-2415.
Kahn S.E., et al., "Glycemic Durability of Rosiglitazone, Metformin, or Glyburide Monotherapy," The New England Journal of Medicine, 2006, vol. 355 (23), pp. 2427-2443.
Kakhki V.R.D., et al., "Normal Values of Gallbladder Ejection Fraction Using 99m Tc-Sestamibi Scintigraphy after a Fatty Meal formula," Journal of Gastrointestinal and Liver Diseases, Jun. 2007, vol. 16 (2), pp. 157-161.
Kamisawa T., et al., "Pancreatographic investigation of Pancreatic Duct System and Pancreaticobiliary Malformation," Journal of Anatomy, 2008, vol. 212 (2), pp. 125-134.
Kanazawa M., et al., "Criteria and Classification of Obesity in Japan and Asia-Oceania," Asia Pacific Journal of Clinical Nutrition, Dec. 2002, vol. 11 (Suppl 7), pp. S732-S737.
Kang S., et al., "Subcutaneous Insulin Absorption Explained by Insulin'S Physicochemical Properties Evidence from Absorption Studies of Soluble Human Insulin and Insulin Analogues in Humans," Diabetes Care, Nov. 1991, vol. 14 (11), pp. 942-948.
Kao C.H., et al., "the Evaluation of Gallbladder Function by Quantitative Radionuclide Cholescintigraphy in Patients with Noninsulin-Dependent Diabetes Mellitus," Nuclear Medicine Communications, 1993, vol. 14 (10), pp. 868-872.
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kastin A.J., et al., "Entry of Exedin-4 into Brain Is Rapid but may be Limited at High Doses International Journal of Obesity and Related Metabolic Disorders," Journal of the International Association for the Study of Obesity, 2003, vol. 27 (3), pp. 313-318.
Kastin A.J., et al., "Interactions of Glucagon-Like Peptide-1 (GLP-1) with the Blood-Brain Barrier," Journal of Molecular Neuroscience, 2001, vol. 18 (1-2), pp. 7-14.
Kelly et al., "Systematic Review: Glucose Control and Cardiovascular Disease in Type 2 Diabetes." Annals Internal Medicine, 2009, vol. 151 (6), pp. 394-403, Sep. 2009; Epub Jul. 20, 2009.
Kemmler W., et al., "Studies on the Conversion of Prolnsulin to Insulin," The Journal of Biological Chemistry, 1971, vol. 246 (22), pp. 6786-6791.
Kendall D.M., et al., "Clinical Application of Incretin-Based Therapy: Therapeutic Potential, Patient Selection and Clinical Use." European Journal of Internal Medicine, Jul. 2009, vol. 20 (Suppl 2), pp. S329-S339.
Kendall D.M., et al., "Effects of Exenatide (Exendin-4) on Glycemic Control Over 30 Weeks in Patients with Type 2 Diabetes Treated with Metformin and a Sulfonylurea," Diabetes care, May 2005, vol. 28 (5), pp. 1083-1091.
Khaw K., et al., "Glycated Haemoglobin, Diabetes, and Mortality in Men in Norfolk Cohort of European Prospective Investigation of Cancer and Nutrition (EPIC Norfolk)." BMJ, Jan. 2001, vol. 322 (7277), pp. 15-18.

(56) References Cited

OTHER PUBLICATIONS

Kielgast U., et al., "Treatment of Type 1 Diabetic Patients with Glucagon-Like Peptide-1 (GLP-1) and GLP-1R Agonists," Current Diabetes Reviews, Nov. 2009, vol. 5 (4), pp. 266-275.

Kim S., et al., "Exendin-4 Protects Dopaminergic Neurons by Inhibition of Microglial Activation and Matrix Metalloproteinase-3 Expression in an Animal Model of Parkinson's Disease," Journal of Endocrinology, 2009, vol. 202 (3), pp. 431-439.

Kim S.Y., et al., "Retinopathy in Monkeys with Spontaneous Type 2 Diabetes" Investigative Opth & Visual Science, Dec. 2004, vol. 45 (12), pp. 4543-4553.

Knee T.S., et al., "A Novel Use of U-500 Insulin for Continuous Subcutaneous Insulin infusion in Patients with Insulin Resistance: A Case Series," Endocrine Practice, May/Jun. 2003, vol. 9 (3), pp. 181-186.

Knudsen L.B., et al., "Potent Derivatives of Glucagon-Like Peptide-1 with Pharmacokinetic Properties Suitable for once Daily Administration," Journal of Medicinal Chemistry, 2000, vol. 43 (9), pp. 1664-1669.

Kohn W.D., et al., "Pi-Shifted Insulin Analogs with Extended in Vivo Time Action and Favorable Receptor Selectivity," Peptides, 2007, vol. 28 (4), pp. 935-948.

Kohner E.M., "Diabetic Retinopathy," British Medical Bulletin, 1989, vol. 45 (1), pp. 148-173.

Kolterman O.G., et al., "Synthetic Exendin-4 (Exenatide) Significantly Reduces Postprandial and Fasting Plasma Glucose in Subjects with Type 2 Diabetes," The Journal of Clinical Endocrinology & Metabolism, 2003, vol. 88 (7), pp. 3082-3089.

Korczyn A.D., et al, "Emerging therapies in the Pharmacological Treatment of Parkinson's Disease," Drugs, 2002, vol. 62 (5), pp. 775-786.

Krishnamurthy G.T., et al., "Constancy and Variability of Gallbladder Ejection Fraction: Impact on Diagnosis and therapy," Journal of Nuclear Medicine, Nov. 2004, vol. 45 (11), pp. 1872-1877.

Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).

Langston J.W., et al., "Chronic Parkinsonism in Humans due to a Product of Meperedine-Analog Synthesis," Science, 1983, vol. 219 (4587), pp. 979-980.

Langui D., et al., "Subcellular Topography of Neuronal Aβ Peptide in APPxPS1 Transgenic Mice," The American Journal of Pathology, 2004, vol. 165 (5), pp. 1465-1477.

Lantus® ANNEX I—Summary of product characteristics. Date of first authorisation: Jun. 9, 2000, pp. 1-164.

Lantus® prescribing information, May 2012, pp. 1-6.

Lantus® Product Information—European Medicines Agency, first published Aug. 5, 2009, pp. 1-2.

Larsen B.D., et al., "Sequence-Assisted Peptide Synthesis (SAPS)," Journal of Peptide Research, 1998, vol. 52 (6), pp. 470-476.

Larsen P.J., et al., "Combination of the Insulin Sensitizer, Pioglitazone, and the Long-Acting Glp-1 Human Analog, Liraglutide, Exerts Potent Synergistic Glucose-Lowering Efficacy in Severely Diabetic ZDF Rats," Diabetes, Obesity and Metabolism, 2008, vol. 10, pp. 301-311.

Laursen K., et al., "Enhanced Monitoring of Biopharmaceutical Product Purity Using Liquid Chromatography-Mass Spectrometry," Journal of Chromatography A, Jul. 2011; Epub May 2011, vol. 1218 (28), pp. 4340-4348.

Lee C.H., et al., "Ischemia-Induced Changes in Glucagon-Like Peptide-1 Receptor and Neuroprotective Effect of its Agonist, Exendin-4, in Experimental Transient Cerebral Ischemia," Journal of Neuroscience Research, 2011, vol. 89 (7), pp. 1103-1113.

Leib R.D., et al., "Direct Quantitation of Peptide Mixtures without Standards Using Clusters formed by Electrospray Ionization Mass Spectrometry," Analytical Chemistry, May 2009, vol. 81 (10), pp. 3965-3972.

Lens J., "The Terminal Carboxyl Groups of Insulin," Biochimica et Biophysica Acta, 1949, vol. 3, pp. 367-370.

Levemir® prescribing information, Dec. 2011, pp. 1-6.

Levene P.A., et al., "Calculation of Isoelectric Point," The Journal of Biological Chemistry, 1923, vol. 55, pp. 801-813.

Levin P., et al., "Combination therapy with Insulin Glargine and Exenatide: Real-World Outcomes in Patients with Type 2 Diabetes," Current Medical Research and Opinion, 2012, vol. 28 (3), pp. 439-446.

Levine R.L., et al., "Oxidation of Methionine in Proteins: Roles in Antioxidant Defense and Cellular Regulation," IUBMB life, Oct. 2000, vol. 50 (4-5), pp. 301-307.

Leyer S., et al., "The Role of the C-Terminus of the Insulin B-Chain in Modulating Structural and Functional Properties of the Hormone," International Journal of Peptide and Protein Research, 1995, vol. 46 (5), pp. 397-407.

Li H., et al., "Chronic Treatment of Exendin-4 Affects Cell Proliferation and Neuroblast Differentiation in the Adult Mouse Hippocampal Dentate Gyrus," Neuroscience letters, 2010, vol. 19, pp. 1205-1219.

Li L., et al., "Common Pathological Processes in Alzheimer Disease and Type 2 Diabetes: A Review," Brain Research Reviews, 2007, vol. 56, pp. 384-402.

Li Y., et al., "Enhancing the GLP-1 Receptor Signaling Pathway Leads to Proliferation and Neuroprotection in Human Neuroblastoma Cells," Journal of Neurochemistry, 2010, vol. 113 (6), pp. 1621-1631.

Li Y., et al., "GLP-1 Receptor Stimulation Preserves Primary Cortical and Dopaminergic Neurons in Cellular and Rodent Models of Stroke and Parkinsonism," Proceedings of the National Academy of Sciences of the United States of America, 2009, vol. 106 (4), pp. 1285-1290.

Li Y., et al., "GLP-1 Receptor Stimulation Reduces Amyloid-Beta Peptide Accumulation and Cytotoxicity in Cellular and Animal Models of Alzheimer's Disease," Journal of Alzheimer's Disease, 2010, vol. 19 (4), pp. 1205-1219.

Lill N., "Production of Fast-Acting Insulins and Delayed-Release Insulins—How can this Problem be Solved by Technology? Insulin formulations," Pharmazie in Unserer Zeit, 2001, vol. 30 (1), pp. 56-61, (English Translation Included).

Liu & Ruus, Abstract "Pharmacokinetics and Safety of the GLP-1 Agonist AVE0010 in Patients with Renal Impairment," Diabetes 58 (Suppl. 1): Abstract 557-P For the 69th Scientific Session of the American Diabetes Association Jun. 5-9, 2009, New Orleans, Louisiana, pp. 1-2.

Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposited, pp. 1-3.

Insulinpraparat Wikipedia, http://de.wikipedia.org/wiki/Insulinpr%C3A4parat, pp. 1-15 (Feb. 5, 2013).

Insuman® Comb25 prescribing information, Feb. 2011, pp. 1-4.

Insuman® Infusat prescribing information, Feb. 2011, pp. 1-4.

Lopez-Delgado M.I., et al., "Effects of Glucagon-Like Peptide 1 on the Kinetics of Glycogen Synthase a in Hepatocytes from Normal and Diabetic Rats," Endocrinology, 1998, vol. 139 (6), pp. 2811-2817.

Lotharius J., et al., "Effect of Mutant Alpha-Synuclein on Dopamine Homeostasis in a New Human Mesencephalic Cell Line," The Journal of Biological Chemistry, 2002, vol. 277 (41), pp. 38884-38894.

Lotharius J., et al., "Progressive Degeneration of Human Mesencephalic Neuron-Derived Cells Triggered by Dopamine-Dependent Oxidative Stress is Dependent on the Mixed-Lineage Kinase Pathway," Journal of Neuroscience, 2005, vol. 25 (27), pp. 6329-6342.

Lougheed W.D., et al., "Physical Stability of Insulin Formulations," Diabetes, 1983, vol. 32 (5), pp. 424-432.

Lyxumia 10 micrograms solution for injection, Summary of Product Characteristics, updated Oct. 31, 2014, pp. 1-12.

Lyxumia® ANNEX I—Summary of product characteristics. Date of first authorisation: Feb. 1, 2013, pp. 1-92.

Lyxumia, Chemical Subgroup A10BX, Community Register of Medicinal Products for Human Use, Eurpean Commission Public Health, p. 1-2 (May 2, 2013).

Lyxumia® Product Information—European Medicines Agency, first published Mar. 14, 2013, pp. 1-2.

(56) References Cited

OTHER PUBLICATIONS

Madsbad S., "Impact of Postprandial Glucose Control on Diabetes-Related Complications: How is the Evidence Evolving?" Journal of Diabetes and Its Complications, 2016, vol. 30, pp. 374-385, Available online Oct. 9, 2015.

Mancuso M., et al., "Clinical Features and Pathogenesis of Alzheimer's Disease: involvement of Mitochondria and Mitochondrial DNA," Advances in Experimental Medicine and Biology, 2010, vol. 685, pp. 34-44.

Marbury T.C., et al., "A Pilot Study to Examine the Feasibility of Insulin Glargine in Subjects with Impaired Fasting Glucose, Impaired Glucose tolerance or New-onset Type 2 Diabetes," Experimental and Clinical Endocrinology & Diabetes, May 2008, vol. 116 (5), pp. 282-288.

Margolis R.L., et al., "Diagnosis of Huntington Disease," Clinical Chemistry, 2003, vol. 49 (10), pp. 1726-1732.

Markussen J., et al., "Soluble, Prolonged-Acting Insulin Derivatives. I. Degree of Protraction and Crystallizability of Insulins Substituted in the Termini of the B-Chain," Protein Engineering, 1987, vol. 1 (3), pp. 205-213.

Markussen J., et al., "Soluble, Prolonged-Acting Insulin Derivatives II Degree of Protraction and Crystallizability of Insulins Substituted in Positions A17, B8, B13, B27 and B30," Protein Engineering, 1987, vol. 1 (3), pp. 215-223.

Markussen J., et al., "Soluble, Prolonged-Acting Insulin Derivatives. III. Degree of Protraction, Crystallizability and Chemical Stability of Insulins Substituted in Positions A21, B13, B23, B27 and B30," Protein Engineering, 1988, vol. 2 (2), pp. 157-166.

Martin B., et al., "Exendin-4 Improves Glycemic Control, Ameliorates Brain and Pancreatic Pathologies, and Extends Survival in a Mouse Model of Huntington's Disease," Diabetes, 2009, vol. 58 (2), pp. 318-328.

Martin L.J., et al., "Neurodegeneration in Excitotoxicity, Global Cerebral Ischemia, and Target Deprivation: A Perspective on the Contributions of Apoptosis and Necrosis," Brain Research Bulletin, 1998, vol. 46 (4), pp. 281-309.

Mattson M.P., "Calcium and Neurodegeneration," Aging Cell, 2007, vol. 6 (3), pp. 337-350.

McClean P.L., et al., "Glucagon-Like Peptide-1 Analogues Enhance Synaptic Plasticity in the Brain: A Link between Diabetes and Alzheimer's Disease," European Journal of Pharmacology, 2010, vol. 630 (1-3), pp. 158-162.

McClean P.L., et al., "The Diabetes Drug Liraglutide Prevents Degenerative Processes in a Mouse Model of Alzheimer's Disease," The Journal of Neuroscience, 2011, vol. 31 (17), pp. 6587-6594.

Mecklenburg R.S., et al., "Complications of Insulin Pump therapy: The Effect of Insulin Preparation," Diabetes Care, 1985, vol. 8 (4), pp. 367-370.

Medline Plus, "Obesity" available at http://www.nlm.nih.gov/medlineplus/obesity.html, Retrieved Aug. 22, 2013, one page.

Meier J.J., "GLP-1 Receptor Agonists for individualized Treatment of Type 2 Diabetes Mellitus," Nature Reviews. Endocrinology, 2012, vol. 8 (12), pp. 728-742.

Merrifield B., "Solid Phase Synthesis," Science, 1986, vol. 232 (4748), pp. 341-347.

Mikhail N.E., "Is Liraglutide a Useful Addition to Diabetes therapy?," Endocrine Practice, Nov.-Dec. 2010, vol. 16 (6), pp. 1028-1037.

Miyazaki Y., et al., "Improved Glycemic Control and Enhanced Insulin Sensitivity in Type 2 Diabetic Subjects Treated with Pioglitazone", Diabetes Care, Apr. 2001, vol. 24(4), pp. 710-719.

Monnier L., et al., "Postprandial and Basal Glucose in Type 2 Diabetes: Assessment and Respective Impacts" Diabetes Technology & Therapeutics, 2011, vol. 13 (Suppl 1 ), pp. S25-S32.

Monnier L., et al., "The Loss of Postprandial Glycemic Control Precedes Stepwise Deterioration of Fasting with Worsening Diabetes," Diabetes Care, 2007, vol. 30 (2), pp. 263-269.

Moreno-Gonzalez I., et al., "Extracellular Amyloid-B and Cytotoxic Glial Activation Induce Significant Entorhinal Neuron Loss in Young PS1M146L/APP751SL Mice," Journal of Alzheimer's Disease, 2009, vol. 18, pp. 755-776.

Moretto T.J., et al., "Efficacy and tolerability of Exenatide Monotherapy Over 24 Weeks in Antidiabetic Drug-Naive Patients with Type 2 Diabetes: A Randomized, Double-Blind, Placebo-Controlled, Parallel-Group Study," Clinical Therapeutics, Aug. 2008, vol. 30 (8), pp. 1448-1460.

Muller G., et al., "Insulin Signaling in the Yeast *Saccharomyces cerevisiae*. 1. Stimulation of Glucose Metabolism and Snf 1 Kinase by Human Insulin," Biochemistry, Jun. 1998, vol. 37 (24), pp. 8683-8695.

Muzaffar M., et al., "The Mechanism of Enhanced Insulin Amyloid Fibril formation by Naciis Better Explained by a Conformational Change Model," PLoS One, 2011, vol. 6 (11), pp. 1-11, e27906.

Nakagawa A., et al., "Receptor Gene Expression of Glucagon-Like Peptide-1, but not Glucose-Dependent Insulinotropic Polypeptide, in Rat Nodose Ganglion Cells," Autonomic Neuroscience, 2004, vol. 110, pp. 36-43.

Nathan D.M., et al., "Management of Hyperglycaemia in Type 2 Diabetes Mellitus: A Consensus Algorithm for the initiation and Adjustment of therapy. Update Regarding the Thiazolidinediones," Diabetologia, 2008, vol. 51 (1), pp. 8-11.

Nathan D.M., et al., "Medical Management of Hyperglycemia in Type 2 Diabetes: A Consensus Algorithm for the Initiation and Adjustment of Therapy" Diabetes Care, Jan. 2009, vol. 32 (1), pp. 193-203.

Nathan M.D., et al., "Insulinotropic Action of Glucagon Like Peptide-1-(7-37) in Diabetic and Nondiabetic Subjects," Diabetes Care, 1992, vol. 15 (2), pp. 270-276.

Nauck M.A., et al., "Comparative Evaluation of Incretin-Based Antidiabetic Medications and Alternative therapies to be Added to Melformin in the Case of Monotherapy Failure," Journal of Diabetes Investigation, Feb.-Apr. 2010, vol. 1 (1-2), pp. 24-36.

Nauck M.A., et al., "Effects of Subcutaneous Glucagon-Like Peptide 1 (GLP-1 [7-36 Amide]) in Patients with NIDDM," Diabetologia, 1996, vol. 39 (12), pp. 1546-1553.

Nauck M.A., et al., "Glucagon-Like Peptide 1 and its Potential in the Treatment of Non-Insulin-Dependent Diabetes Mellitus," Hormone and Metabolic Research, 1997, vol. 29 (9), pp. 411-416.

Nauck M.A., et al., "Glucagon-Like Peptide 1 (GLP-1) as a New therapeutic Approach for Type 2-Diabetes," Experimental and Clinical Endocrinology, 1997, vol. 105 (4), pp. 187-195.

NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.

NCT00688701 Clinical Trials.gov "GLP-1 Receptor Agonist Lixisenatide in Patients with Type 2 Diabetes for Glycemic Control and Safety Evaluation in Monotherapy (GETGOAL-MONO)" accessed Jul. 27, 2014; pp. 1-5.

NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.

NCT00713830, Clinical Trials.gov "GLP-1 Agonist in Patients with Type 2 Diabetes for Glycemic Control and Safety Evaluation, on Top of Sulfonylurea", 2016, pp. 1-3, accessed Mar. 16, 2016, (Updated Jul. 13, 2008).

NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011).

NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GETGOAL-P)" pp. 1-8 (Jun. 27, 2011).

NCT00866658 ClinicaiTrials.gov, "GLP-1 Agonist AVE0010 in Patients with Type 2 Diabetes for Glycemic Control Safety Evaluation, on Top of Basil Insulin+/− Sulfonylurea," 2016, pp. 1-3, accessed Mar. 16, (Updated Jan. 010).

NCT00975286, Clinical Trials.gov, "24-week Treatment with Lixisenalide in Type 2 Diabetes Insufficiently Controlled With Melformin and Insulin Glargine", Aug. 8, 2011, pp. 1-4.

(56) References Cited

OTHER PUBLICATIONS

NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
NCT01169779, Clinical Trials.gov, "Efficacy and Safety of Lixisenatide in Patients with Type 2 Diabetes Mellitus Insufficiently Controlled by Metformin," 2016, pp. 1-3, accessed Mar. 16, 2016, (updated Mar. 28, 2011).
NCT01174810, ClinicalTrials.gov "Exendin-4 as a Treatment for Parkinson's Disease—Pilot Study" accessed Aug. 8, 2011, pp. 1-5.
NCT01195454, NIH Clinical Trials, "Euglycemic clamp dose-response study comparing insulin glargine U300 with Lantus U100" last updated Dec. 13, 2010, pp. 1-4.
NCT01255163, ClinicalTrials.gov "A Clinical Trial of Exendin-4 for the Treatment of Alzheimer's Disease" accessed Aug. 8, 2011, pp. 1-7.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
Needleman S.B., et al., "A General Method Applicable to the Search for Similarities in the Amino Acid Sequence of Two Proteins," Journal of Molecular Biology, 1970, vol. 48 (3), pp. 443-453.
Neidle, "18.2 Failure Modes in the Discovery Process" Cancer Drug Design and Discovery, Elsevier/Academic Press, pp. 427-431 (2008).
Nettleton E.J., et al., "Characterization of the Oligomeric States of Insulin in Self-Assembly and Amyloid Fibril formation by Mass Spectrometry," Biophysical Journal, 2000, vol. 79 (2), pp. 1053-1065.
NHSC—National Horizon Scanning Center, "AVE0010 (ZP10) for type 2 diabetes mellitus" University of Birmingham, England; pp. 1-6 (Dec. 2008).
NICE, National Institute for Health and Care Excellence, "Evidence Summary: New Medicine, ESNM26: Type 2 Diabetes: lixisenatide; Key Points from the Evidence," Sep. 24, 2013, pp. 1-26.
Nicklas et al., "Inhibition of Nadh-Linked Oxidation in Brain Mitochondria by 1-Methyl-4-Phenyl-Pyridine, A Metabolite of the Neurotoxin, 1-Methyl-4-Phenyl-1,2,5,6-Tetrahydropyridine," Life Sciences, 1985, vol. 36, pp. 2503-2508.
Nielsen L.L., et al., "Pharmacology of Exenatide (Synthetic Exendin-4): A Potential therapeutic for Improved Glycemic Control of Type 2 Diabetes," Regulatory Peptides, 2004, vol. 117 (2), pp. 77-88.
NIH, National Institute of Diabetes and Digestive and Kidney Disease, "Hypoglycimia," Mar. 16, 2016, pp. 1-8.
Nilsson A., et al., "Effects of GI vs Content of Cereal Fibre of the Evening Meal on Glucose Tolerance at a Subsequent Standardized Breakfast," European Journal of Clinical Nutrition, Jun. 2008, vol. 62 (6), pp. 712-720 (Epub May 23, 2007).
Noble S.L., et al., "Insulin Lispro: A Fast-Acting Insulin Analog," American Family Physician, 1998, vol. 57 (2), pp. 279-286.
Non-Final Office Action from U.S. Appl. No. 12/617,805; dated Jul. 24, 2014, pp. 1-12.
Non-Final Office Action from U.S. Appl. No. 12/617,805; dated May 2, 2012, pp. 1-11.
Non-Final Office Action from U.S. Appl. No. 12/617,805; dated May 10, 2011, pp. 1-12.
Non-Final Office Action from U.S. Appl. No. 12/617,805; dated Sep. 15, 2015, pp. 1-12.
Non-Final Office Action issued in U.S. Appl. No. 13/123,835; dated Dec. 22, 2014, pp. 1-13.
Non-Final Office Action issued in U.S. Appl. No. 13/123,835; dated Jul. 19, 2012, pp. 1-14.
Non-Final Office Action issued in U.S. Appl. No. 13/123,835; dated May 28, 2015, pp. 1-11.
Non-Final Office Action issued in U.S. Appl. No. 13/602,913; dated Dec. 2, 2014, pp. 1-12.
Non-Final Office Action issued in U.S. Appl. No. 13/602,913; dated Jan. 13, 2014, pp. 1-53.
Non-Final Office Action issued in U.S. Appl. No. 13/602,913; dated May 17, 2013, pp. 1-7.
Non-Final Rejection in U.S. Appl. No. 13/633,496; dated Apr. 29, 2013, pp. 1-53.
Non-Final Rejection in U.S. Appl. No. 13/633,496; dated Apr. 6, 2015, pp. 1-14.
Non-Final Rejection in U.S. Appl. No. 13/633,496; dated May 22, 2014, pp. 1-11.
Non-Final Rejection in U.S. Appl. No. 13/633,563; dated Dec. 1, 2014, pp. 1-9.
Non-Final Rejection in U.S. Appl. No. 13/633,563; dated Jul. 1, 2013, pp. 1-56.
Non-Final Rejection in U.S. Appl. No. 13/633,563; dated Jun. 4, 2014, pp. 1-11.
Non-Final Rejection in U.S. Appl. No. 13/633,563; dated Oct. 6, 2015, pp. 1-12.
Non-Final Rejection issued in U.S. Appl. No. 14/172,151; dated Mar. 24, 2015, pp. 1-16.
Non-Final Rejection issued in U.S. Appl. No. 12/617,811; dated Apr. 27, 2011, pp. 1-10.
Non-Final Rejection issued in U.S. Appl. No. 12/617,811; dated Jan. 14, 2015, pp. 1-15.
Non-Final Rejection issued in U.S. Appl. No. 12/617,811; dated Jun. 21, 2012, pp. 1-7.
Non-Final Rejection issued in U.S. Appl. No. 12/617,811; dated Oct. 27, 2011, pp. 1-13.
Non-Final Rejection issued in U.S. Appl. No. 13/110,568; dated Mar. 19, 2012, pp. 1-18.
Non-Final Rejection issued in U.S. Appl. No. 13/310,118; dated Mar. 19, 2012, pp. 1-19.
Non-Final Rejection issued in U.S. Appl. No. 13/310,118, dated Mar. 29, 2013, pp. 1-21.
Non-Final Rejection issued in U.S. Appl. No. 13/310,118, dated Mar. 25, 2015, pp. 1-15.
Non-Final Rejection issued in U.S. Appl. No. 13/363,956; dated Apr. 10, 2013, pp. 1-15.
Non-Final Rejection issued in U.S. Appl. No. 13/363,956; dated Feb. 11, 2015, pp. 1-18.
Non-Final Rejection issued in U.S. Appl. No. 13/363,956; dated May 29, 2015, pp. 1-17.
Non-Final Rejection issued in U.S. Appl. No. 13/363,956; dated Nov. 20, 2013, pp. 1-10.
Non-Final Rejection issued in U.S. Appl. No. 13/382,442; dated Nov. 7, 2012, pp. 1-26.
Non-Final Rejection issued in U.S. Appl. No. 13/382,442; dated Dec. 19, 2013, pp. 1-29.
Non-Final Rejection issued in U.S. Appl. No. 13/382,442; dated Feb. 5, 2015, pp. 1-31.
Non-Final Rejection issued in U.S. Appl. No. 13/382,442; dated Mar. 31, 2016, pp. 1-29.
Non-Final Rejection issued in U.S. Appl. No. 13/382,772; dated Nov. 21, 2013, pp. 1-42.
Non-Final Rejection issued in U.S. Appl. No. 13/382,772; dated Sep. 29, 2014, pp. 1-33.
Non-Final Rejection issued in U.S. Appl. No. 13/382,772; dated Sep. 14, 2015, pp. 1-42.
Non-Final Rejection issued in U.S. Appl. No. 13/467,707; dated Jul. 15, 2013, pp. 1-20.
Non-Final Rejection issued in U.S. Appl. No. 13/467,707; dated Jul. 25, 2014, pp. 1-22.
Non-Final Rejection issued in U.S. Appl. No. 13/467,707; dated Sep. 16, 2015, pp. 1-13.
Non-Final Rejection issued in U.S. Appl. No. 13/468,422; dated Nov. 4, 2015; pp. 1-27.

(56) References Cited

OTHER PUBLICATIONS

Non-Final Rejection issued in U.S. Appl. No. 13/469,633; dated Aug. 19, 2013, pp. 1-25.
Non-Final Rejection issued in U.S. Appl. No. 13/469,633; dated Aug. 22, 2014, pp. 1-23.
Non-Final Rejection issued in U.S. Appl. No. 13/469,633; dated Mar. 27, 2013, pp. 1-39.
Non-Final Rejection issued in U.S. Appl. No. 13/509,507; dated Aug. 6, 2013, pp. 1-11.
Non-Final Rejection issued in U.S. Appl. No. 13/509,507; dated Sep. 19, 2014, pp. 1-9.
Non-Final Rejection issued in U.S. Appl. No. 13/509,507; dated Feb. 19, 2015, pp. 1-10.
Non-Final Rejection issued in U.S. Appl. No. 13/509,507; dated Dec. 8, 2015, pp. 1-14.
Non-Final Rejection issued in U.S. Appl. No. 13/509,542; dated May 23, 2013, pp. 1-21.
Non-Final Rejection issued in U.S. Appl. No. 13/509,542; dated Apr. 2, 2014, pp. 1-20.
Non-Final Rejection issued in U.S. Appl. No. 13/509,542; dated Aug. 11, 2015, pp. 1-30.
Non-Final Rejection issued in U.S. Appl. No. 13/595,590; dated Jun. 5, 2015, pp. 1-9.
Non-Final Rejection issued in U.S. Appl. No. 13/595,590; dated Oct. 16, 2013, pp. 1-7.
Non-Final Rejection issued in U.S. Appl. No. 13/595,590; dated Sep. 5, 2014, pp. 1-10.
Non-Final Rejection issued in U.S. Appl. No. 13/661,476; dated Jun. 4, 2015, pp. 1-31.
Non-Final Rejection issued in U.S. Appl. No. 13/661,476; dated Dec. 4, 2013, pp. 1-11.
Non-Final Rejection issued in U.S. Appl. No. 13/661,476; dated Mar. 6, 2014, pp. 1-28.
Non-Final Rejection issued in U.S. Appl. No. 13/661,476; dated Sep. 16, 2013, pp. 1-19.
Non-Final Rejection issued in U.S. Appl. No. 13/692,640; dated May 6, 2014, pp. 1-10.
Non-Final Rejection issued in U.S. Appl. No. 13/692,640; dated Oct. 31, 2013, pp. 1-10.
Non-Final Rejection issued in U.S. Appl. No. 13/700,631; dated Apr. 22, 2013, pp. 1-27.
Non-Final Rejection issued in U.S. Appl. No. 13/700,631; dated Dec. 17, 2015, pp. 1-18.
Non-Final Rejection issued in U.S. Appl. No. 13/700,631; dated Nov. 18, 2014, pp. 1-22.
Non-Final Rejection issued in U.S. Appl. No. 13/700,631; dated Nov. 29, 2013, pp. 1-23.
Non-Final Rejection issued in U.S. Appl. No. 13/819,114; dated Dec. 2, 2015, pp. 1-14.
Non-Final Rejection issued in U.S. Appl. No. 13/819,114; dated Jul. 31, 2014, pp. 1-9.
Non-Final Rejection issued in U.S. Appl. No. 14/220,562; dated Apr. 8, 2015, pp. 1-18.
Non-Final Rejection issued in U.S. Appl. No. 14/303,895; dated May 21, 2015, pp. 1-11.
Non-Final Rejection issued in U.S. Appl. No. 14/303,895; dated Sep. 9, 2015, pp. 1-12.
Non-Final Rejection issued in U.S. Appl. No. 13/467,757; dated Apr. 17, 2013, pp. 1-9.
Non-Final Rejection issued in U.S. Appl. No. 13/468,422; dated Jun. 4, 2014, pp. 1-24.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Non-Final Rejection issued in U.S. Appl. No. 13/382,772; dated Apr. 10, 2013, pp. 1-48.
Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.
Non-Final-Rejection issued in U.S. Appl. No. 13/432,811; dated Sep. 9, 2015, pp. 1-11.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Olansky L., "Do Incretin-Based Therapies Cause Acute Pancreatitis?," Journal of Diabetes Science and Technology, Jan. 2010, vol. 4 (1), pp. 228-229.
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov C., "Glucagon-Like Peptide-1, A New Hormone of the Entero-insular Axis," Diabetologia, 1992, vol. 35 (8), pp. 701-711.
Ott P., et al., "Diabetes in Germany(Dig) Study a Prospective 4-Year-Follow-Up Study on the Quality of Treatment for Type 2 Diabetes in Daily Practice," Deutsche Medizinische Wochenschrift, 2009, vol. 134 (7), pp. 291-297, English Absract submitted.
Park C.W., et al., "Long-Term Treatment of Glucagon-Like Peptide-1 Analog Exendin-4 Ameliorates Diabetic Nephropathy through Improving Metabolic Anomalies in db/db Mice." Journal American Society Nephrology, 2007, vol. 18 (4), pp. 1227-1238, Apr. 2007; Epub Mar. 14, 2007.
Park C.W., et al., "PPARalpha Agonist Fenofibrate Improves Diabetic Nephropathy in Db/Db Mice," Kidney International, Published Online Mar. 1, 2006, vol. 69 (9), pp. 1511-1517.
Parkin "Guideline for Management of Postmeal Glucose" International Diabetes Federation, pp. 1-32 (Oct. 2007).
Patel & Advance Collaborative Group, "Effects of a Fixed Combination of Perindopril and indapamide on Macrovascular and Microvascular Outcomes in Patients with Type 2 Diabetes Mellitus (the Advance Trial): A Randomised Controlled Trial," Lancet, 2007, vol. 370 (9590), pp. 829-840.
Patel K., et al., "Chemical Pathways of Peptide Degradation. II. Kinetics of Deamidation of an Asparaginyl Residue in a Model Hexapeptide," Pharmaceutical Research, 1990, vol. 7 (8), pp. 703-711.
Pederson R.A., et al., "Improved Glucose tolerance in Zucker Fatty Rats by oral Administration of the Dipeptidyl Peptidase IV inhibitor Isoleucine Thiazolidide," Diabetes, 1998, vol. 47 (8), pp. 1253-1258.
Perfetti R., "Combining Basal Insulin Analogs with Glucagon-Like Peptide-1 Mimetics," Diabetes Technology & Therapeutics, 2011, vol. 13 (9), pp. 873-881.
Perry T., et al., "A Novel Neurotrophic Property of Glucagon-Like Peptide 1: A Promoter of Nerve Growth Factor-Mediated Differentiation in PC12 Cells," The Journal of Pharmacology and Experimental Therapeutics, 2002, vol. 300 (3), pp. 958-966.
Perry T., et al., "Evidence of GLP-1-Mediated Neuroprotection in an Animal Model of Pyridoxine-induced Peripheral Sensory Neuropathy," Experimental Neurology, 2007, vol. 203 (2), pp. 293-301.
Perry T., et al., "Protection and Reversal of Excitotoxic Neuronal Damage by Glucagon-Like Peptide-1 and Exendin-4," The Journal of Pharmacology and Experimental Therapeutics, 2002, vol. 302 (3), pp. 881-888.
Perry T., et al., "The Glucagon-Like Peptides: A Double-Edged therapeutic Sword?," Trends in Pharmacological Sciences, 2003, vol. 24 (7), pp. 377-383.
Perry T.A., et al., "A New Alzheimer's Disease interventive Strategy: GLP-1," Current Drug Targets, Aug. 2004, vol. 5 (6), pp. 565-571.
Pillion D.J., et al., "Dodecylmaltoside-Mediated Nasal and Ocular Absorption of Lyspro-Insulin: Independence of Surfactant from Multimer Dissociation," Pharmaceutical Research, Oct. 1998, vol. 15(10), pp. 1637-1639.
Pinget M., et al., "Efficacy and safety of lixisenatide once daily versus placebo in type 2 diabetes insufficiently controlled on pioglitazone (GetGoal-P)," Diabetes,61(Supp 1):A258, Poster 1010-P(Jun. 2012).
Pinhas-Hamiel O., et al., "Clinical Presentation and Treatment of Type 2 Diabetes in Children," Pediatric Diabetes, Dec. 2007, vol. 8 (Suppl. 9), pp. 16-27.

(56) References Cited

OTHER PUBLICATIONS

Pi-Sunyer F.X., "The Effects of Pharmacologic Agents for Type 2 Diabetes Mellitus on Body Weight," Postgraduate Medicine, Jul. 2008, vol. 120 (2), pp. 5-17.
Pohl M., et al., "Molecular Cloning of the Heloderman and Exendin-4 cDNAs in the Lizard," The Journal of Biological Chemistry, 1998, vol. 273 (16), pp. 9778-9784.
Porter D.W., et al., "Four Weeks Administration of Liraglutide Improves Memory and Learning As Well As Glycaemic Control in Mice with High Fat Dietary-induced Obesity and Insulin Resistance," Diabetes, Obesity and Metabolism, 2010, vol. 12 (10), pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini N., "Methods of Measuring Gallbladder Motor Functions—the Need for Standardization: Scintigraphy," Digestive and Liver Disease, 2003, vol. 35 (Suppl 3), pp. S62-66.
"Preferable." Merriam-Webster.com. Merriam-Webster, n.d. Web. Sep. 7, 2015. http://www.merriamwebster.com/dictionary/preferable).
Pugeat M., et al., "Insulin Resistance, Polycystic Ovary Syndrome and Metformin," Drugs, Sep. 1999, vol. 58 (Suppl 1), pp. 41-46.
Quianzon C.L., et al., "Lixisentide-Once Daily Glucagon-Like Peptide-1 Receptor Agonist in the Management of Type 2 Diabetes," US Endocrinology, 2011, vol. 7 (2), pp. 104-109, (Winter 2011).
Raccah D., et al., "When Basal Insulin therapy in Type 2 Diabetes Mellitus is not Enough—What Next?," Diabetes/Metabolism Research and Reviews, Published Online Feb. 21, 2007, vol. 23 (4), pp. 257-264.
Raju R.P., et al., "Optimum Palliation of inoperable Hilar Cholangiocarcinoma: Comparative Assessment of the Efficacy of Plastic and Self-Expanding Metal Stents," Digestive Diseases and Sciences, published online, Jan. 11, 2011, vol. 56, pp. 1557-1564.
Ramos B., et al., "Early Neuropathology of Somatostatin/NPY Gabaergic Cells in the Hippocampus of a Ps1xAPP Transgenic Model of Alzheimer's Disease," Neurobiology of Aging, 2006, vol. 27 (11), pp. 1658-1672.
Rao A.D., et al., "Is the Combination of Sulfonylureas and Metformin Associated with an increased Risk of Cardiovascular Disease or all-Cause Mortality? A Meta-Analysis of Observational Studies," Diabetes Care, 2008, vol. 31 (8), pp. 1672-1678.
Ratner R.E., et al., "Dose-Dependent Effects of the Once-Daily GLP-1 Receptor Agonist Lixisenatide in Patients with Type 2 Diabetes Inadequately Controlled with Metformin: A Randomized Double-Blind, Placebo-Controlled Trial," Diabetic Medicine, Sep. 2010, vol. 27 (9), pp. 1024-1032.
Ratner R.E., et al., "Post-Meal Pharmacodynamics Profile of Ave0010, A Once-Daily GLP-1 Receptor Agonist, in Patiens with Type 2 Diabetes Inadequately Controlled on Metformin," Diabetologia, Sep. 2009, vol. 52 (Suppl 1), pp. S60. Abstract 131.
Ratner R.E., et al., "Abstract # 433-P, A Dose-Finding Study of the New GLP-1 Agonist AVE0010 in Type 2 Diabetes Insufficiently Controlled with Metformin," Diabetes, Poster, 68th Annual Meeting of the American Diabetes Association, San Francisco, Jun. 6-10, 2008, vol. 57 (Suppl 1), p. A129.
Raufman J.P., "Bioactive Peptides from Lizard Venoms," Regulatory peptides, 1996, vol. 61 (1), pp. 1-18.
"Remington: The Science and Practice of Pharmacy", Twentieth Edition, Lippincott Williams & Wilkins, USA, 2000, pp. 1-5.
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle M., et al., "Contributions of Basal and Postprandial Hyperglycemia over a Wide Range of A 1 C Levels before and after Treatment Intensification in Type 2 Diabetes," Diabetes Care, Published Online Oct. 25, 2011, vol. 34, pp. 2508-2514.
Riddle M.C., et al., "Adding Once-Daily Lixisenatide for Type 2 Diabetes Inadequately Controlled by Established Basal Insulin: A 24-Week, Randomized, Placebo-Controlled Comparison (Getgoal-L)," Diabetes Care, Sep. 2013, vol. 36 (9), pp. 2489-2496.
Riddle M.C., et al., "Adding once-Daily Lixisenatide for Type 2 Diabetes inadequately Controlled with Newly initiated and Continuously Titrated Basal Insulin Glargine," Diabetes Care, Sep. 2013, pp. 2497-2503.
Ritzel U., et al., "A Synthetic Glucagon-Like Peptide-1 Analog with Improved Plasma Stability," The Journal of Endocrinology, 1998, vol. 159 (1), pp. 93-102.
Rohrmann C.A., "Differential Diagnosis of Pancreatic and Biliary Duct Diseases," Diseases of the Abdomen and Pelvis Syllabus, 1999, pp. 170-174.
Rosenstock J., et al., "Dose Range Effects of the New Once Daily GLP-1 Receptor Agonist AVE0010 Added to Metformin in Type 2 Diabetes," Diabetologia, Sep. 2008, vol. 51 (Suppl 1), pp. S66. Abstract 145.
Rosenstock J., et al., "Efficacy and Safety of Lixisenatide Once Daily vs Exenatiide Twice Daily in Type 2 DM Inadequately Controlled on Metformin (GetGoal-X)," 71st Scientific Sessions, Nov. 2011. Poster.
Rosenstock J., et al., "Post-Meal Effects of Ave0010, A Once-Daily GLP-1 Receptor Agonist, in Type 2 Diabetes Inadequately Controlled on Metformin," Diabetes, Jun. 1, 2009, vol. 58 (Suppl 1), pp. A151-A152. Abstract 564P.
Rubino A., et al., "Delayed initiation of Subcutaneous Insulin therapy after Failure of oral Glucose-Lowering Agents in Patients with Type 2 Diabetes: A Population-Based Analysis in the UK," Diabetic Medicine, 2007, vol. 24 (12), pp. 1412-1418.
Sampson H.A., et al., "Second Symposium on the Definition and Management of Anaphylaxis: Summary Report—Second National institute of Allergy and infectious Disease/Food Allergy and Anaphylaxis Network Symposium," The Journal of Allergy and Clinical Immunology, 2006, vol. 117 (2), pp. 391-397.
Sanger F., et al., "The Amide Groups of Insulin," The Biochemical Journal, 1955, vol. 59 (3), pp. 509-518.
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.
Sanofi Press Release entitled "FDA Accepts Sanofi's New Drug Application for Basal Insulin Toujeo®," dated Jul. 8, 2014, pp. 1-2.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi-Aventis Press Release, "A Promising R&D Portfolio, Well Positioned to Deliver Future Growth," Sep. 17, 2007, pp. 1-11.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.

(56) References Cited

OTHER PUBLICATIONS

Sanofi-aventis Press Release, "Once Daily Lixisenatide (Ave 0010) Given as Monotherapy Successfully Meets Phase III Study Endpoints in Diabetes" Paris, France (Apr. 15, 2010) pp. 1-2.
Sanofi-aventis Press Release (Peron and Schaeffer), "Sanofi-aventis Announces Positive Top-line Lixisentatide Phase III Results" Paris, France (Feb. 2, 2011) pp. 1-2.
Sanofi Press Release entitled "Sanofi Receives FDA Approval of Once-Daily Basal Insulin Toujeo®," dated Feb. 26, 2015, pp. 1-4.
Schapira A.H., "Causes of Neuronal Death in Parkinson's Disease," Advances in Neurology, 2001, vol. 86, pp. 155-162.
Schellenberger V., et al., "Attempts for Quantifying the S' Subsite Specificity of Serine Proteases, Selected Papers Presented at the 2nd International Meeting on the Molecular and Cellular Regulation of Enzyme Activity, Advances in the Biosciences, Peptides and Proteases," Recent Advances, 1987, vol. 65, pp. 159-166.
Schellenberger V., et al., "Protease-Catalyzed Kinetically Controlled Peptide Synthesis," Angewante Chemie, 1991, vol. 30 (11), pp. 1437-1449.
Schindowski K., et al., "Impact of Aging: Sporadic, and Genetic Risk Factors on Vulnerability to Apoptosis in Alzheimer's Disease," Neuromolecular Medicine, 2003, vol. 4 (3), pp. 161-178.
Schmitz C., et al., "Hippocampal Neuron Loss Exceeds Amyloid Plaque Load in a Transgenic Mouse Model of Alzheimer's Disease," The American Journal of Pathology, 2004, vol. 164 (4), pp. 1495-1502.
Schubert-Zsilavecz M., et al., "Better Blood Sugar Control in Diabetics. Insulin Glargin—A Long Acting Insulin Analogue," Pharmazie in Unserer Zeit, 2001, vol. 30 (2), pp. 125-130, With English translation.
Schwartz G.J., et al., "New Equations to Estimate GFR in Children with CKD," Journal of the American Society of Nephrology, Mar. 2009, vol. 20 (3), pp. 629-637 (Epub Jan. 21, 2009).
Schwartz G.P., et al., "A Superactive Insulin: [B10-Aspartic Acid]Insulin(Human)," Proceedings of the National Academy of Sciences of the United States of America, Sep. 1987, vol. 84 (18), pp. 6408-6411.
Search Report of the Indecopi for Patent Application in Peru No. 000643-2012/DIN, dated Jul. 23, 2015, pp. 1-2.
Search Report of the Intellectual Property Corporation of Malaysia for Malaysian Patent Application No. PI 2011006204; dated Sep. 15, 2015, pp. 1-3.
Search Report of the Intellectual Property Office of Singapore for Patent Application No. 10201500871T, dated Nov. 2, 2015, pp. 1-3.
Secnik Boye K., et al., "Patient-Reported Outcomes in a Trial of Exenatide and Insulin Glargine for the Treatment of Type 2 Diabetes," Health and Quality of Life Outcomes, Oct. 2006, vol. 4 (80), pp. 1-8.
Seino Y., et al., "Report of the Committee on the Classification and Diagnostic Criteria of Diabetes Mellitus," Journal of the Japan Diabetes Society, 2010, vol. 53, pp. 450-467 (in Japanese) English summary also provided.
Seino Y., et al., "Randomized, Double-Blind, Placebo-Controlled Trial of the Once-Daily GLP-1 Receptor Agonist Lixisenatide in Asian Patients with Type 2 Diabetes Insufficiently Controlled on Basal Insulin with or without a Sulfonylurea (Getgoal-L-Asia)," Diabetes, Obesity and Metabolism, 2012, vol. 14 (10), pp. 910-917.
Sharplin P., et al., "Improved Glycaemic Control by Switching from Insulin NPH to Insulin Glargine: A Retrospective Observational Study," Cardiovascular Diabetology, Published Jan. 19, 2009, vol. 8 (3), pp. 1-8.
Sherer T.B., et al., "Subcutaneous Rotenone Exposure Causes Highly Selective Dopaminergic Degeneration and A-Synuclein Aggregation," Experimental Neurology, 2003, vol. 179, pp. 9-16.
Sluzky V., et al., "Kinetics of Insulin Aggregation in Aqueous Solutions Upon Agitation in the Presence of Hydrophobic Surfaces," Proceedings of the National Academy of Sciences of the United States of America, Nov. 1991, vol. 88 (21), pp. 9377-9381.

Smolka M.B., et al., "Optimization of the Isotope-Coded Affinity Tag-Labeling Procedure for Quantitative Proteome Analysis," Analytical Biochemistry, Oct. 2001, vol. 297 (1), pp. 25-31, Abstract only submitted.
Spertus J.A., et al., "Development and Evaluation of the Seattle Anginal Questionnaire: a New Functional Status Measure for Coronary Artery Disease." Journal American College of Cardiology, Feb. 1995, vol. 25 (2), pp. 333-341.
Spertus J.A., et al., "Health Status Predicts Long-Term Outcome in Outpatients with Coronary Disease." Circulation, Jul. 2002, vol. 106 (1 ), pp. 43-49.
Sporn M.B., et al., "Chemoprevention of Cancer," Carcinogenesis, 2000, vol. 21 (3), pp. 535-530.
Srinivasan K., et al., "Animal Models in Type 2 Diabetes Research: An Overview." Indian Journal Medical Research, Mar. 2007, vol. 125, pp. 451-472.
St. John Providence Health Center, "Preventing Obesity" http://www.stjohnprovidence.org/HealthInfolib/swarticle.aspx?type=85 &id= P07863, Retrieved Aug. 22, 2013, pp. 1-2.
Starkova N.T., "Clinical Endocrinology," Guide for physicians, Medicine, 1991, pp. 192-262.
Stolk R.P., et al., "Insulin and Cognitive Function in an Elderly Population the Rotterdam Study," Diabetes Care, 1997, vol. 20 (5), pp. 792-795.
Summary of Product Characteristics Lyxumia 10 micrograms solution for injection, pp. 1-93, published Mar. 14, 2013.
Sundby F., "Separation and Characterization of Acid-induced Insulin Transformation Products by Paper Electrophoresis in 7 M Urea," The Journal of Biological Chemistry, Nov. 1962, vol. 237 (11), pp. 3406-3411.
Tanner C.M., et al., "Rotenone, Paraquat, and Parkinson's Disease," Environmental Health Perspectives, 2011, vol. 119 (6), pp. 866-872.
Tanner J.M., et al., "Standards from Birth to Maturity for Height, Weight, Height Velocity, and Weight Velocity: British Children, Part II," Archives of Disease in Childhood, 1966, vol. 41 (220), pp. 613-635.
Tempero M.A., "How I Treat Pancreatic Ductal Adenocarcinoma," Current Clinical Issues, Journal of Oncology Practice, 2008, vol. 4 (1), pp. 46-47.
Teramoto S., et al., "Exendin-4, a Glucagon-Like Peptide-1 Receptor Agonist, provides Neuroprotection in Mice Transient Focal Cerebral Ischemia," Journal of Cerebral Blood Flow and Metabolism, 2011, vol. 31 ( 8), pp. 1696-1705.
Tessari P., et al., "Insulin in Methionine and Homocysteine Kinetics in Healthy Humans: Plasma Vs intracellular Models," American Journal of Physiology. Endocrinology and Metabolism, 2005, vol. 288 (6), pp. E1270-E1276.
Tetich M., et al., "Neuroprotective Effects of (24R)-1,24-Dihydroxycholecalciferol in Human Neuroblastoma SH-SY5Y Cell Line," The Journal of Steroid Biochemistry and Molecular Biology, 2004, vol. 89-90 (1-5), pp. 365-370.
Tews D., et al., "Enhanced Protection against Cytokine- and Fatty Acid-Induced Apoptosis in Lns-1 Beta-Cells by Combined Treatment with Insulin Glargine and the Novel GLP-1 Receptor Agonist Ave0010," Diabetes, 2007, vol. 56 (Suppl 1), pp. A72-A73.
Tews D., et al., "Enhanced Protection Against Cytokine- and Fatty Acid-induced Apoptosis in Pancreatic Beta Cells by Combined Treatment with Glucagon-Like Peptide-1 Receptor Agonists and Insulin Analogues," Hormone and Metabolic Research, Mar. 2008, vol. 40 (3), pp. 172-180.
The Advance Collaborative Group, "Intensive Blood Glucose Control and Vascular Outcomes in Patients with Type 2 Diabetes." New England Journal of Medicine, Jun. 2008, vol. 358 (24), pp. 2560-2572.
The Diabetes Control and Complications Trial Research Group, "The Effect of intensive Treatment of Diabetes on the Development and Progression of Long-Term Complications in Insulin-Dependent Diabetes Mellitus," The New England Journal of Medicine, Sep. 1993, vol. 329, pp. 977-986.
Thong K.Y., et al., "Safety, Efficacy and tolerability of Exenatide in Combination with Insulin in the Association of British Clinical Diabetologists Nationwide Exenatide Audit," Diabetes, Obesity and Metabolism, 2011, vol. 13 (8), pp. 703-710.

(56) References Cited

OTHER PUBLICATIONS

Thurow H., et al., "Stabilisation of Dissolved Proteins against Denaturation at Hydrophobic Interfaces," Diabetologia, Aug. 1984, vol. 27 (2), pp. 212-218.
Toth M.L., et al., "Neurite Sprouting and Synapse Deterioration in the Aging Caenorhabditis Elegans Nervous System," The Journal of Neuroscience, 2012, vol. 32 (26), pp. 8778-8790.
Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 750, 753 and 754 of Igaku No Ayumi, "Incretin Receptors," May 2010, vol. 233; No. 9: 750-754, pp. 1-4.
Turner R.C., et al., "Glycemic Control with Diet, Sulfonylurea, Metformin, or Insulin in Patients with Type 2 Diabetes Mellitus: Progressive Requirement for Multiple therapies (UKPDS 49)," JAMA, 1999, vol. 281 (21), pp. 2005-2012.
Tyler-Cross R., et al., "Effects of Amino Acid Sequence, Buffers, and Ionic Strength on the Rate and Mechanism of Deamidation of Asparagine Residues in Small Peptides," The Journal of Biological Chemistry, 1991, vol. 266 (33), pp. 22549-22556.
UK Prospective Diabetes Study (UKPDS) Group, "Effect of intensive Blood-Glucose Control with Metformin on Complications in Overweight Patients with Type 2 Diabetes (UKPDS 34)," Lancet, Sep. 1998, vol. 352 (9131), pp. 854-865.
UK Prospective Diabetes Study (UKPDS) Group, "Intensive Blood-Glucose Control with Sulphonylureas or Insulin Compared with Conventional Treatment and Risk of Complications in Patients with Type 2 Diabetes (UKPDS 33)," The Lancet, Sep. 12, 1998, vol. 352, pp. 837-853.
UK Prospective Diabetes Study (UKPDS) Group, "Tight Blood Pressure Control and Risk of Macrovascular and Microvascular Complications in Type 2 Diabetes (UKPDS 38)," BMJ, Sep. 1998, vol. 317, pp. 703-713.
"Suspension" Stedman's Medical Dictionary, 20th Edition, p. 1450 (Williams & Wilkins Co., Baltimore 1961).
"Suspension" Taber's Cyclopedic Medical Dictionary, 19th Edition, p. 2097 (F.A. Davis Co., Philadelphia 2001).
Uttenthal L.O., et al., "Molecular forms of Glucagon-Like Peptide-1 in Human Pancreas and Glucagonomas," The Journal of Clinical Endocrinology & Metabolism, 1985, vol. 61 (3), pp. 472-479.
Valle J., et al., "Cisplatin Plus Gemcitabine Versus Gemcitabine for Biliary Tract Cancer," The New England Journal of Medicine, Apr. 2010, vol. 362 (14), pp. 1273-1281.
Van Delden, "Pancreas-Carcinoma, CT Assessment of Resectability," Radiology Department of the Academical Medical Centre, Apr. 2006, pp. 1-12.
Varadarajan S., et al., "Review: Alzheimer's Amyloid Beta-Peptide-Associated Free Radical Oxidative Stress and Neurotoxicity," Journal of Structural Biology, 2000, vol. 130 (2-3), pp. 184-208.
Venezia V., et al., "Apoptotic Cell Death and Amyloid Precursor Protein Signaling in Neuroblastoma SH-SY5Y Cells," Annals of the New York Academy of Sciences, 2004, vol. 1030, pp. 339-347.
Victoza® Annex I—Summary of product characteristics. First published 2009, pp. 1-32.
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Volund A., et al., "In Vitro and in Vivo Potency of Insulin Analogues Designed for Clinical Use," Diabetic Medicine, Nov. 1991, vol. 8 (9), pp. 839-847.
Vora J., et al., "Incretin-Based therapy in Combination with Basal Insulin: A Promising Tactic for the Treatment of Type 2 Diabetes," Diabetes & Metabolism, 2013, vol. 39 (1), pp. 6-15.
Wafa W.S., et al., "Use of U-500 Regular Insulin in Type 2 Diabetes," Diabetes Care, 2006, vol. 29 (9), pp. 2175-2176.
Wajchenberg B.L., "Clinical Approaches to Preserve Beta-Cell Function in Diabetes," Advances in Experimental Medicine and Biology, 2010, vol. 654, pp. 515-535.
Wan Z., et al., "Enhancing the Activity of Insulin at the Receptor Interface: Crystal Structure and Photo-Cross- Linking of A8 Analogues," Biochemistry, 2004, vol. 43 (51), pp. 16119-16133.
Wang L., et al., "Real-World Outcomes of US Employees with Type 2 Diabetes Mellitus Treated with Insulin Glargine or Neutral Protamine Hagedorn Insulin: A Comparative Retrospective Database Study," BMJ Open, 2013, vol. 3 (4), pp. e002348 1-9.
Ward J.D., "Diabetic Neuropathy," British Medical Bulletin, Jan. 1989, vol. 45 (1), pp. 111-126.
Watson G.S., et al., "Insulin increases CSF Abeta42 Levels in Normal Older Adults," Neurology, 2003, vol. 60 (12), pp. 1899-1903.
Weiss M.A., et al., "Activities of Monomeric Insulin Analogs at Position A8 are Uncorrelated with their thermodynamic Stabilities," The Journal of Biological Chemistry, 2001, vol. 276 (43), pp. 40018-40024.
Werner et al., "Abstract, Insulin Glargine U-100 Has a Favourable Time-Action Profile Compared to U-40 or NPH Insulin in Healthy, Normoglycaemic Dogs", Poster 37th Annual Meeting of Endocrine Society of India, Tirupati, A.P., India, ESICON, 2007, p. 2, (2 Pages Including Abstract and Poster).
Werner U., et al., "Pharmacological Profile of Lixisenatide: A New GLP-1 Receptor Agonist for the Treatment of Type 2 Diabetes," Regulatory Peptides, Epub Jun. 2, 2010, vol. 164 (2-3), pp. 58-64.
Weyer C., et al., "Long-Term Changes in Insulin Action and Insulin Secretion Associated with Gain, Loss, Regain and Maintenance of Body Weight," Diabetologia, Jan. 2000, vol. 43 (1), pp. 36-46.
White I.R., et al., "Randomized Clinical Trials with Added Rescue Medication: Some Approaches to their Analysis and interpretation," Statistics in medicine, 2001, vol. 20 (20), pp. 2995-3008.
Whittingham J.L., et al., "Insulin at pH 2: Structural Analysis of the Conditions Promoting Insulin Fibre formation," Journal of Molecular Biology, 2002, vol. 318 (2), pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
WHO Rational Use of Medicines,http://www.who.int/medicines/areas/rational_use/en/downloaded Dec. 18, 2014 10:02:48 AM (2012).
Widjaja A., et al., "UKPDS 20: Plasma Leptin, Obesity, and Plasma Insulin in Type 2 Diabetic Subjects," The Journal of Clinical Endocrinology and Metabolism, 1997, vol. 82 (2), pp. 654-657.
Wiernsperger N.F., et al., "The Antihyperglycaemic Effect of Metformin: Therapeutic and Cellular Mechanisms," Drugs, Sep. 1999, vol. 58 (Suppl 1), pp. 31-39.
Wikipedia® Entry for "Body Mass Index" Retrieved from the Internet: https://en.wikipedia.org/wiki/Body mass_index, 2016, pp. 1-14, retrieved Feb. 26, 2016.
Wikipedia® Entry for "Lixisenatide" Retrieved from the Internet: https://en.wikipedia.org/wiki/Lixisenatide one page, retrieved Apr. 11, 2016.
Wikipedia® Entry for "Metformin" Retrieved from the Internet: https://en.wikipedia.org/wiki/Metformin 2016, pp. 1-21, retrieved Apr. 11, 2016.
Wikipedia® Entry for "Pioglitazone" Retrieved from the Internet: https://en.wikipedia.org/wiki/Pioglitazone 2016, pp. 1-3, retrieved Apr. 11, 2016.
Wirths O., et al., "Intraneuronal Abeta Accumulation Precedes Plaque formation in beta-Amyloid Precursor Protein and Presenilin-1 Double-Transgenic Mice," Neuroscience Letters, 2001, vol. 306 (1-2), pp. 116-120.
Wirths O., et al., "Intraneuronal APP/A Beta Trafficking and Plaque formation in Beta-Amyloid Precursor Protein and Presenilin-1 Transgenic Mice," Brain Pathology, 2002, vol. 12 (3), pp. 275-286.

(56) References Cited

OTHER PUBLICATIONS

Wirths O., et al., "Reelin in Plaques of Beta-Amyloid Precursor Protein and Presenilin-1 Double-Transgenic Mice," Neuroscience Letters, 2001, vol. 316 (3), pp. 145-148.
Wivioti S.D., et al., "Greater Clinical Benefit of More Intensive Oral Anti platelet Therapy With Prasugrel in Patients With Diabetes Mellitus in the Trial to Assess Improvement in Therapeutic Outcomes by Optimizing Platelet Inhibition With Prasugrei-Thrombolysis in Myocardial Infarction 38," Circulation, 2008, vol. 118 (16), pp. 1626-1636, Oct. 2008; Epub Aug. 31, 2008.
Wollen K.A., "Alzheimer's Disease: the Pros and Cons of Pharmaceutical, Nutritional, Botanical, and Stimulatory therapies, with a Discussion of Treatment Strategies from the Perspective of Patients and Practitioners," Alternative Medicine Review, 2010, vol. 15 (3), pp. 223-244.
World Health Organisation Report on "Definition and Diagnosis of Diabetes Mellitus and Intermediate Hyperglycemia: Report of a WHO/IDF Consultation," 2006, pp. 1-50.
World Health Organization, "Definition, Diagnosis and Classification of Diabetes Mellitus and its Complications, Part 1: Diagnosis and Classification of Diabetes Mellitus," WHO/NCD/NCS/99.2, Geneva, 1999, pp. 1-66.
Written Opinion of the ISA for International Application No. PCT/EP2011/058079, dated Mar. 22, 2012, pp. 1-8.
Xie H., et al., "Characterization of Protein Impurities and Site-Specific Modifications Using Peptide Mapping with Liquid Chromatography and Data Independent Acquisition Mass Spectrometry," Analytical Chemistry, Jul. 2009, vol. 81 (14), pp. 5699-5708.
Yki-Jarvinen H., et al., "Insulin Glargine or Nph Combined with Metformin in Type 2 Diabetes: The Lanmet Study," Diabetologia, Mar. 2006, vol. 49 (3), pp. 442-451.
Yki-Jarvinen H., "Thiazolidinediones," The New England Journal of Medicine, Sep. 2004, vol. 351 (11), pp. 1106-1118.
Yoon N.M., et al., "Exenatide Added to Insulin therapy: A Retrospective Review of Clinical Practice Over Two Years in an Academic Endocrinology Outpatient Setting," Clinical Therapeutics, 2009, vol. 31 (7), pp. 1511-1523.
Yu Z.P., et al., "Effect of Zinc Sulphate and Zinc Methionine on Growth, Plasma Growth Hormone Concentration, Growth Hormone Receptor and Insulin-Like Growth Factor-I Gene Expression in Mice," Clinical and Experimental Pharmacology & Physiology, 2005, vol. 32 (4), pp. 273-278, Abstract only.
Yusuf S., et al., "Effects of Clopidogrel in Addition to Aspirin in Patients with Acute Coronary Syndromes without ST-Segment Elevation." New England Journal Medical, Aug. 2001, vol. 345 (7), pp. 494-502.
Zealand Pharma Company Announcement "Zealand Pharma, Additional positive results from Global Phase III program with -3-lixisenatide for type 2 diabetes", Apr. 12, 2011, pp. 1- 3, URL, http://files.shareholder.com/downloads/ABEA-58QR0J/0x0x458202/3ccd84a6-5f99-451a-ada0-0a8282da3dad/ZEAL_News_2011_4_12Company_Releases.pdf.
Zealand Pharma Press Release entitled "Sanofi-Aventis finalize phase lia clinical study with GLP-1 agonist for type 2 diabetes licensed from Zealand Pharma" dated Mar. 3, 2005, one page.
Ziemer D.C., et al., "Clinical Inertia Contributes to Poor Diabetes Control in a Primary Care Setting," The Diabetes Educator, 2005, vol. 31 (4), pp. 564-571.
Ziessman H.A., et al., "Sincalide-Stimulated Cholescintigraphy: A Multicenter Investigation to Determine Optimal Infusion Methodology and Gallbladder Ejection Fraction Normal Values," Journal of Nuclear Medicine, Feb. 2010, vol. 51 (2), pp. 277-281.
Zimmet P., et al., "Clinical Efficacy of Metformin Against Insulin Resistance Parameters: Sinking the Iceberg," Review Article, Drugs, Sep. 1999, vol. 58 (Suppl 1), pp. 21-28.
Zinman B., et al., "Efficacy and Safety of the Human Glucagon-Like Peptide-1 Analog Liraglutide in Combination with Metformin and Thiazolidinedione in Patients with Type 2 Diabetes (LEAD-4 Met+ TZD)," Diabetes Care, Jul. 2009, vol. 32 (7), pp. 1224-1230.

Zinman B., "The Physiologic Replacement of Insulin an Elusive Goal," The New England Journal of Medicine, Aug. 1989, vol. 321 (6), pp. 363-370.
Zoungas et al., "Combined Effects of Routine Blood Pressure Lowering and Intensive Glucose Control on Macrovascular and Microvascular Outcomes in Patients With Type 2 Diabetes. New results from the Advance trial." Diabetes Care, 2009, vol. 32(11 ), pp. 2068-2074, Nov. 2009; Epub Aug. 3, 2009.
Petrie, "The cardiovascular safety of incretin-based therapies: a review of the evidence" Cardiovascular Diabetology, 12(1):130, 12 pages (Sep. 2013).
Pinget et al., "Efficacy and safety of lixisenatide once daily versus placebo in type 2 diabetes insufficiently controlled on pioglitazone (GetGoal-P)," Diabetes, Obesity and Metabolism, 15(11):1000-1007 (Nov. 2013; Epub May 26, 2013).
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Raman & Heptulla, "New potential adjuncts to treatment of children with type 1 diabetes mellitus" Pediatric Research, 65(4):370-74 (Apr. 2009).
Ratner et al., "Efficacy and safety of lixisenatide once-daily versus placebo in patients with type 2 diabetes mellitus insufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.
Register of medicaments (RM), 2003, issue 10, p. 517.
Remington: The Science and Practice of Pharmacy, Twentieth Edition, Lippincott Williams & Wilkins, USA, "Oral Hypoglycemic and Hyperglycemic Drugs" pp. 1373 and 1375; 2000.
Riddle et al., "The treat-to-target trial: randomized addition of glargine or human NPH insulin to oral therapy of type 2 diabetes patients." Diabetes Care 26(11):3080-86 (Nov. 2003).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Rodbard et al., "Statement by an American Association of Clinical Endocrinologists/American College of Endocrinology Consensus Panel on Type 2 Diabetes Mellitus: An Algorithm for Glycemic Control" Endocrine Practice 15(6):540-59 (Sep./Oct. 2009).
Rothstein et al., "Anticandida activity is retained in P-113, a 12-amino-acid fragment of histatin 5." Antimicrob Agents Chemother. 45(5):1367-73 (May 2001).
Rosenstock et al., "Reduced Hypoglycemia Risk with Insulin Glargine: A meta-analysis comparing insulin glargine with human NPH insulin in type 2 diabetes" Diabetes Care 28(4):950-55 (Apr. 2005).
RPMI-1640 Media Formulation, Sigma Aldrich, accessed on Jul. 10, 2016, pp. 1-5.
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones, "Current developments in the treatment of diabetes: the incretin therapies" Br J Diabetes Vasc Dis. 10:21-30 (Feb. 2010).
Sacks et al., "Guidelines and Recommendations for Laboratory Analysis in the Diagnosis and Management of Diabetes Mellitus." Clinical Chemistry 48(3):436-72 (Mar. 2002).
Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, pp. 1-12 (2015). retrieved from the internet: http://en.sanofi.com/img/content/study/PKD11475_summary.pdf (retrieved on Jun. 16, 2015).
Sanofi-aventis Press Release, "Once Daily Lixisenatide in Combination with Basal Insulin Demonstrates Significant Improvement in Glucose Control" Paris, France (Sep. 30, 2010) pp. 1-3.
Sanofi Press Release entitled "Sanofi Announces Top-Line Results for Cardiovascular Outcomes Study of Lyxumia® (lixisenatide).", dated Mar. 19, 2015, Paris, France, pp. 1-2.

(56) References Cited

OTHER PUBLICATIONS

Shehadeh et al., "Can GLP-1 preparations be used in children and adolescents with diabetes mellitus?" Pediatric Endocrinology Reviews, 11(3):324-27 (Mar. 2014).
Shi, "The Newest Handbook of Clinical Drugs" Military Medical Science Press, p. 809, (Jan. 2008). English translation submitted.
Sillars et al., "Sulphonylurea-metformin combination therapy, cardiovascular disease and all-cause mortality: the Fremantle Diabetes Study." Diabetes Obes Metab. 12(9):757-65 (Sep. 2010).
Sloop et al., "Glucagon as a target for the treatment of Type 2 diabetes." Expert Opin Ther Targets. 9(3):593-600 (Jun. 2005).
Spasov & Chepurnova, "Scientific Approaches to Combination Therapy for Type 2 Diabetes Mellitus," Bulletin of Volgograd State Medical University,1(37):8-10 (2011). See English Abstract.
Stumvoll et al., "Type 2 diabetes: Principles of pathogenesis and therapy" Lancet 365(9467):1333-46 (Apr. 2005).
Sutter Medical Foundation, "Type 2 Diabetes Adult Outpatient Insulin Guidelines" Feb. 2011, pp. 1-6.
Tang, "Biotech Drugs—Introduction and Practice Handbook" Chemical Industry Press, pp. 635-636, (Jan. 2008). English translation submitted.
Tanner & Davies, "Clinical longitudinal standards for height and height velocity for North American children." J Pediatr. 107(3):317-29 (Sep. 1985).
Tirosh et al., "Normal Fasting Plasma Glucose Levels and Type 2 Diabetes in Young Men" New England Journal of Medicine, 353(14):1454-62 (Oct. 2005).
UK Prospective Diabetes Study (UKPDS) Group 28: A randomized trial of efficacy of early addition of metformin in sulfonylurea-treated type 2 diabetes. Diabetes Care, 21(1):87-92 (Jan. 1998).
Van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).
Van Gaal & De Leeuw, "Rationale and options for combination treatment of type 2 diabetes." Diabletologia 46 (Supplement 1):M44-M50 (Mar. 2003).
Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).
Wahlin-Boll et al., "Impaired effect of sulfonylurea following increased dosage." Eur J Clin Pharmacol 22(1):21-25 (1982).
Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.
Werner, "Preclinical pharmacology of the new GLP-1 receptor agonist AVE0010", Ann. Endocrinol. (Paris), 69 (2)164-65 (Apr. 2008).
WHO, World Health Organization Media Center. Obesity and overweight, Fact Sheet No. 311. Updated Jan. 2015, pp. 1-5.
Wikipedia® entry for "Stratified sampling" Retrieved on Mar. 28, 2017, pp. 1-4.
Williams & Pickup, "Macrovascular disease in Diabetes." In handbook of Diabetes. 2nd ed. Williams G, Pickup JC, Eds. Oxford, UK, Blackwell Science Chapter 21; pp. 151-158 (1999).
Wohlfart et al., "Cardioprotective effects of lixisenatide in rat myocardial ischemia-reperfusion injury studies" Journal of Translational Medicine, 11(1):84, 12 pages (Mar. 2013).
Wolever et al., "Second-meal effect: low-glycemic-index foods eaten at dinner improve subsequent breakfast glycemic response" Am J Clin Nutr 48(4):1041-47 (Oct. 1988).
Yki-Järvinen, "Combination Therapies with insulin in type 2 diabetes." Diabetes Care 24(4):758-67 (Apr. 2001).
Yki-Järvinen et al., "Comparison of Bedtime insulin regimes in patients with type 2 diabetes mellitus." Annals of Internal Medicine 130(5):389-96 (Mar. 1999).
Zeitler et al , "ISPAD Clinical Practice Consensus Guidelines 2014. Type 2 diabetes in the child and adolescent." Pediatr Diabetes 15(Suppl 20)26-46 (Sep. 2014).
Zimmet et al., "The metabolic syndrome in children and adolescents." Lancet 369(9579):2059-61 (Jun. 2007).
Zinman et al., "The Effect of Adding Exenatide to a Thiazolidinedione in Suboptimally Controlled Type 2 Diabetes" Annals of Internal Medicine, 146(7):477-85 (Apr. 2007).
Final Office Action issued in U.S. Appl. No. 13/123,835; dated Nov. 18, 2015, pp. 1-16.
Non-Final Office Action issued in U.S. Appl. No. 15/340,969; dated Jul. 24, 2017, pp. 1-6.
Non-Final Rejection issued in U.S. Appl. No. 13/382,442; dated Sep. 20, 2017, pp. 1-28.
Final Rejection issued in U.S. Appl. No. 13/382,442; dated Sep. 21, 2016, pp. 1-32.
Non-Final Office Action issued in U.S. Appl. No. 15/275,867; dated Jun. 1, 2017; pp. 1-11.
Non-Final Rejection issued in U.S. Appl. No. 13/509,507; dated Sep. 21, 2016, pp. 1-7.
Non-Final Rejection issued in U.S. Appl. No. 13/509,542; dated Nov. 23, 2016, pp. 1-34.
Non-Final Rejection issued in U.S. Appl. No. 14/172,151; dated Jan. 19, 2017, pp. 1-20.
Final Rejection issued in U.S. Appl. No. 14/172,151; dated Jan. 4, 2016, pp. 1-20.
Non-Final Rejection issued in U.S. Appl. No. 13/467,707; dated Jun. 30, 2016, pp. 1-9.
Non-Final Rejection issued in U.S. Appl. No. 13/467,707; dated Nov. 7, 2016, pp. 1-17.
Non-Final Rejection issued in U.S. Appl. No. 15/197,378; dated Jun. 15, 2017, pp. 1-13.
Non-Final Office Action issued in U.S. Appl. No. 15/145,255; dated Sep. 18, 2017, pp. 1-10.
Non-Final Rejection in U.S. Appl. No. 13/633,563; dated Oct. 5, 2016, pp. 1-12.
Final Rejection in U.S. Appl. No. 13/633,496; dated Oct. 13, 2016, pp. 1-10.
Non-Final Rejection in U.S. Appl. No. 13/633,496; dated May 25, 2017, pp. 1-10.
Non-Final Rejection issued in U.S. Appl. No. 14/303,895; dated Mar. 24, 2017, pp. 1-17.
Non-Final Rejection issued in U.S. Appl. No. 15/073,364; dated Nov. 9, 2017, pp. 1-8.
Non-Final Rejection issued in U.S. Appl. No. 14/965,586; dated Mar. 22, 2017, pp. 1-17.
Non-Final Rejection issued in U.S. Appl. No. 15/068,286; dated Apr. 11, 2017, pp. 1-12.
International Search Report by the ISA for International Application No. PCT/EP2009/000018; dated Jun. 30, 2009, pp. 1-8.
International Search Report by the ISA for International Application No. PCT/EP2016/050804; dated Mar. 4, 2016, pp. 1-4.
International Search Report by the ISA for International Application No. PCT/EP2016/055267; dated May 20, 2016, pp. 1-7.
International Search Report by the ISA for International Application No. PCT/EP2016/055267; dated Jun. 7, 2016, pp. 1-8.
Partial International Search Report by the ISA for International Application No. PCT/EP2016/055954; dated Jun. 21, 2016, pp. 1-6.
International Search Report by the ISA for International Application No. PCT/EP2016/055954; dated Sep. 9, 2016, pp. 1-12.
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
Extended European Search Report for European Application No. 16 19 0103.8; dated Jun. 23, 2017, pp. 1-5.
Search Report in Chinese Patent Application No. 201410818149.0; dated Jan. 10, 2017, pp. 1-3. English translation submitted.
U.S. Appl. No. 13/819,114, filed Apr. 29, 2013, Boka et al.
U.S. Appl. No. 13/363,956, filed Feb. 1, 2012, Silvestre et al.
U.S. Appl. No. 13/432,811, filed Mar. 28, 2012, Boka et al.

(56) References Cited

OTHER PUBLICATIONS

U.S. Appl. No. 13/469,633, filed May 11, 2012, Ruus et al.
U.S. Appl. No. 13/467,707, filed May 9, 2012, Niemoller et al.
U.S. Appl. No. 13/468,422, filed May 10, 2012, Silvestre et al.
U.S. Appl. No. 13/467,757, filed May 9, 2012, Silvestre et al.
U.S. Appl. No. 13/661,476, filed Oct. 26, 2012, Silvestre et al.
U.S. Appl. No. 15/340,969, filed Nov. 1, 2016, Werner et al.
U.S. Appl. No. 15/595,929, May 17, 2017, Brunner-Schwarz et al.
U.S. Appl. No. 15/275,867, filed Sep. 26, 2016, Silvestre et al.
U.S. Appl. No. 15/237,285, filed Aug. 15, 2016, Boka et al.
U.S. Appl. No. 15/144,270, filed May 2, 2016, Silvestre et al.
U.S. Appl. No. 15/411,557, filed Jan. 20, 2017, Boka et al.
U.S. Appl. No. 15/197,378, filed Jun. 29, 2016, Niemöller.
U.S. Appl. No. 15/146,255, filed May 4, 2016, Hess et al.
U.S. Appl. No. 15/657,683, filed Jul. 24, 2017, Souhami et al.
Abraira et al., "Glycaemic separation and risk factor control in the Veterans Affairs Diabetes Trial: an interim report." Diabetes Obes Metab 11(2):150-56. (2009; Epub Jul. 29, 2008).
Ampudia-Blasco et al., "Basal Plus Basal-Bolus approach in type 2 diabetes." Diabetes Technol Ther. 13 Suppl 1: S75-83 (Jun. 2011).
Atkinson et al., "validation of a general measure of treatment satisfaction, the Treatment Satisfaction Questionnaire for Medication (TSQM), using a national panel study of chronic disease." Health Qual Life Outcomes. 2:12, pp. 1-13 (Feb. 2004).
Beckman et al., "Diabetes and atherosclerosis: epidemiology, pathophysiology, and management." JAMA 287 (19):2570-81 (May 2002).
Brazier et al., "Testing the validity of the Euroqol and comparing it with the SF-36 health survey questionnaire." Qual Life Res 2(3):169-80 (Jun. 1993).
Byetta® Summary of product characteristics. ANNEX I, pp. 1-71, (2011).
Byetta® Product information. EMA pp. 1-2, accessed Jun. 10, 2016.
De Lemos et al., "Early intensive vs. a delayed conservative simvastatin strategy in patients with acute coronary syndromes: phase Z of the A to Z trial." JAMA 292(11):1307-16 (Sep. 2004; Epub Aug. 30, 2004).
Del Prato & Tiengo, "The importance of first-phase insulin secretion: implications for the therapy of type 2 diabetes mellitus." Diabetes Metab Res Rev. 17(3):164-74 (May-Jun. 2001).
Del Prato et al., "Global Partnership for Effective Diabetes Management. Tailoring treatment to the individual in type 2 diabetes practical guidance from the Global partnership for effective diabetes managment." Int J Clin Pract. 64 (3)295-304 (Feb. 2010).
DeWitt & Hirsch, "Outpatient insulin therapy in type 1 and type 2 diabetes mellitus: scientific review." JAMA 289 (17):2254-64 (May 2003).
Dinneen & Gerstein, "The association of microalbuminuria and mortality in non-insulin dependent diabetes mellitus. A systematic overview of the literature." Arch Intern Med 157(13):1413-8 (Jul. 1997).
Dolan, "Modeling valuations for EuroQol health states." Med Care 35(11):1095-1108 (Nov. 1997).
Encyclopedia of Drugs, "Metformin" Moscow, Drug Register of 2001, p. 549, English translation provided pp. 1-2.
EuroQol Group, "EuroQol—a new facility for the measurement of health-related quality of life." Health policy (Amsterdam, Netherlands) 16(3):199-208 (Dec. 1990).
FDA, Food and Drug Administration. Guidance for Industry—Diabetes Mellitus: Developing Drugs and Therapeutic Biologics for Treatment and Prevention. pp. 1-34 (Feb. 2008).
Gerstein et al., "Albuminuria and risk of cardiovascular events, death, and heart failure in diabetic and nondiabetic individuals." JAMA 286(4):421-6 (Jul. 2001).
Holman et al., "Three-year efficacy of complex insulin regimens in type 2 diabetes." N Engl J Med. 361(18):1736-47 (Oct. 2009; Epub Oct. 22, 2009).
Inzucchi et al., "Management of hyperglycaemia in type 2 diabetes: a patient-centered approach. Position statement of the American Diabetes Association (ADA) and the European Association for the Study of Diabeters (EASD)." Diabetologia. 55(6):1577-96 (Jun. 2012; Epub Apr. 20, 2012).
Juniper et al., "Determining a minimal important change in a disease-specific quality of life questionnaire." J Clin Epidemiol 47(1):81-87 (Jan. 1994).
King et al., Global burden of diabetes, 1995-2025. Prevalence, numerical estimates and projections. Diabetes Care 21(9)1414-31 (Sep. 1998).
Kolotkin et al., "Assessing impact of weight on quality of life." Obes Res. 3(1):49-56 (Jan. 1995).
Kolotkin et al., "Development of a brief measure to assess quality of life in obesity." Obes Res. 9(2):102-11 (Feb. 2001).
Korytkowski, "When oral agents fail: practical barriers to starting insulin." Int J Obes Relat Metab Disord. 26 Suppl 3:S18-24 (Sep. 2002).
Lovshin & Drucker, "Incretin-based therapy for type 2 diabetes mellitus." Nat. Rev. Endocrinol. 5(5):262-69 (May 2009).
McFarlane, "Insulin therapy and type 2 diabetes: management of weight gain," J Clin Hypertens (Greenwich). 11(10):601-7 (Oct. 2009).
Meadows et al, "The diabetes health profile (DHP): a new instrument for assessing the psychosocial profile of insulin requiring patients: development and psychometric evaluation," Qual. Life Res. 5(2):242-54 (Apr. 1996).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Monnier & Colette, "Addition of rapid-acting insulin to basal insulin therapy in type 2 diabetes: indications and modalities." Diabetes Metab 32(1):7-13 (Feb. 2006).
Nathan et al., "Modern-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).
Nowels et al., "Validation of the EQ-50 quality of life instrument in patients after myocardial infarction." Qual Life Res 14(1):95-105 (Feb. 2005).
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Ray et al., "Effect of intensive control of glucose on cardiovascular outcomes and death in patients with diabetes mellitus: a meta-analysis of randomized controlled trials." Lancet 373(9677):1765-72 (May 2009).
Rosenstock J et al., Advancing Basal Insulin Glargine with Prandial Lixisenatide QD vs. Insulin Glulisine QD or TID in T2DM: The GetGoalDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.
Russell-Jones & Khan, insulin-associated weight gain in diabetes: causes, effects and coping strategies. Diabetes Obes Metab.9(6):799-812 (Nov. 2007).
Merck Index, "Metformin", The Merck Index, 15th Edition (2013), RSC Publishing, 4 pages submitted, see p. 6009.
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).
Seino et al., "Lixisenatide significantly improves glycemic control in Asian patients with T2DM insufficiently controlled on basal insulin ± SU." Diabetes, Abstract book for 71st Scientific Session. p. A76; Abstract 278-OR (2011).
Shaw et al., "US valuation of the EQ-5D health states: development and testing of the D1 valuation model." Med Care 43(3):203-20 (Mar. 2005).
Spertus et al., "Monitoring the quality of life in patients with coronary heart disease." Am J Cardiol. 74(12):1240-44 (Dec. 1994).

(56) References Cited

OTHER PUBLICATIONS

Standardized Definitions for Cardiovascular Outcomes Trials: Draft Recommendations. Division of Metabolism and Endocrinology Products. Center for Drug Evaluation and Research (CDER). Jul. 22, 2009.
Definition of "Combination", Concise Oxford English Dictionary, edited by A. Stevenson and M. Waite, Oxford University press, 12th Edition, Aug. 2011, 4 pages submitted, see p. 285.
Weir "Glucagon-like peptide-1 (7-37) actions on endocrine pancreas." Diabetes 38(3):338-42 (Mar. 1989).
WHO, World Health Organization Media Center. Diabetes Fact Sheet. Available from: http://www.who.int/mediacentre/factsheets/fs312/en/index.html. Accessed Jun. 13, 2016, pp. 1-6.
Wild et al., "Global prevalence of diabetes: estimates for the year 2000 and projections for 2030." Diabetes Care 27 (5)1047-53 (May 2004).
Williams et al., "Macrovascular disease in Diabetes" In handbook of Diabetes. 4nd ed. Williams G, Pickup JC, Eds. Oxford, UK, Blackwell Science pp. 151-58 (2010).
Wright et al., U.K. Prospective Diabetes Study Group. "Sulfonylurea inadequacy: efficacy of addition of insulin over 6 years in patients with type 2 diabetes in the UK. Prospective Diabetes Study (UKPDS 57)." Diabetes Care 25 (2):330-36 (Feb. 2002).
Zimmet et al., "Global and societal implications of the diabetes epidemic" Nature 414(6865):782-87 (Dec. 2001).
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
Soeborg et al., "Absorption kinetics of insulin after subcutaneous administration" European Journal of Pharmaceutical Sciences 36(1):78-90 (Jan. 2009; Epub Nov. 5, 2008).
Soliqua® Product Information; pp. 1-33 (Oct. 2017).
Soliqua® Consumer Medicine Information (CMI); pp. 1-7 (Oct. 2017).
Soliqua® Summary of Product Characteristics; pp. 1-74 (Jan. 2017).
Stitt et al., "The progress in understanding and treatment of diabetic retinopathy" Progress in Retinal and Eye Research 51:156-186 (2016; Epub Aug. 18, 2015).
Urakami et al., "Pharmacologic treatment strategies in children with type 2 diabetes mellitus", Clin Pediatr Endocrinol., 22(1):1-8 (Jan. 2013).
Wang, "Instability, Stabilization and Formulation of Liquid Protein Pharmaceuticals," Int'l J Pharm, 185(2):129-88 (Aug. 1999).
Wikipedia® entry for "Standard deviation" Retrieved on Oct. 10, 2017, pp. 1-3.
Yu et al., "Glucagon-like peptide-1 prevented abdominal aortic aneurysm development in rats" Sugr. Today 446:1099-1107 (2016).
Final Rejection issued in U.S. Appl. No. 13/382,442; dated Apr. 16, 2018, pp. 1-28.
Non-Final Rejection issued is U.S. Appl. No. 15/595,929; dated Sep. 20, 2017, pp. 1-9.
Non-Final Rejection issued in U.S. Appl. No. 15/237,285; dated Sep. 29, 2017, pp. 1-10.
Non-Final Rejection issued in U.S. Appl. No. 15/144,270; dated Dec. 13, 2017, pp. 1-25.
Non-Final Rejection issued in U.S. Appl. No. 15/411,557; dated Mar. 19, 2018, pp. 1-11.
Non-Final Rejection issued in U.S. Appl. No. 14/624,575; dated Mar. 26, 2015, pp. 1-14.
Non-Final Rejection issued in U.S. Appl. No. 15/162,563; dated Feb. 8, 2017, pp. 1-13.
Final Rejection issued in U.S. Appl. No. 15/162,563; dated Aug. 9, 2017, pp. 1-11.
Final Rejection issued in U.S. Appl. No. 15/162,563; dated Dec. 18, 2017, pp. 1-16.
Final Rejection issued in U.S. Appl. No. 15/162,563; dated Apr. 17, 2018, pp. 1-16.
Final Rejection in U.S. Appl. No. 13/633,563; dated Apr. 28, 2017, pp. 1-12.
Non-Final Rejection issued in U.S. Appl. No. 14/995,910; dated Dec. 11, 2017, pp. 1-7.
Extended European Search Report for European Application No. 17 17 4341; dated Nov. 7, 2017, pp. 1-3.
Extended European Search Report for European Application No. 17 20 2727.8; dated Dec. 20, 2017, pp. 1-9.
English translation of Search Report for Chinese Patent Application No. 201480045284.4; dated May 16, 2018, pages 1-3.
Search Report of the Intellectual Property Office of Singapore for Patent Application No. 10201403840V; search completed Nov. 21, 2017 and dated Jan. 4, 2017, pp. 1-3.
Search Report of the Intellectual Property Office of Singapore for Patent Application No. 11201704678S; search completed May 25, 2018 and dated Jun. 14, 2018, pp. 1-2.
Search Report of the Intellectual Property Office of Singapore for Patent Application No. 11201705755U search completed Jun. 5, 2018 and dated Jun. 20, 2018, pp. 1-2.
Glucophage XR, Product Information, Bristol-Meyers Squibb Company (Jan. 2009).
Godoy-Matos, "The role of glucagon on type 2 diabetes at a glance," Diabetology & Metabolic Syndrome 6:91, pp. 1-5 (Aug. 2014).
Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Gromada et al., "Alpha-Cells of the Endocrine Pancreas: 35 Years of Research but the Enigma Remains" Endocrine Reviews 28(1):84-116 (Jan. 2007).
Gualandi-Signorini & Giorgi, "Insulin formulations—a review" European Review for Medical and Pharmacological Sciences 5:73-83 (2001).
Halimi, "DPP-4 inhibitors and GlLP-1 analogues: for whom? Which place for incretins in the management of type 2 diabetic patients?", Diabetes & Metabolism 34(Supplement 2):S91-S95 (Feb. 2008).
Harkavyi & Whitton, "Glucagon-like peptide 1 receptor stimulation as a means of neuroprotection" British Journal of Pharmacology 159(3):495-501 (2010; Epub Jan. 29, 2010).
Hasslacher et al., "Diabetic kidney disease" Exp and Clin Endocrinol Diabetes 122(7):391-94 (Jul. 2014).
Heine & Dekker, "Beyond postprandial hyperglycemia: metabolic factors associated with cardiovascular disease." Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).
Hollander & Kushner, "Type 2 Diabetes Comorbidities and Treatment Challenges: Rationale for DPP4-Inhibitors" Postgraduate Medicine, 122(3):71-80 (May 2010).
Home et al., "Management of type 2 diabetes: updated NICE guidance" BMJ 336: 1306-1308 (Jun. 2008).
Hubschle et al., "Anti-atherosclerotic activity of lixisenatide in ApoE knockout mice" Abstract 809, Diabetologia, 55 (Supplement 1):S334 (Oct. 2012).
Ismail-Beigi et al., "Individualizing Glycemic Targets in Type 2 Diabetes Mellitus: Implications of Recent Clinical Trials" Annals of Internal Medicine 154(8):554-559 (Apr. 2011).
Janka et al., "Comparison of basal insulin added to oral agents versus twice-daily premixed insulin as initial insulin therapy for type 2 diabetes." Diabetes Care 28(2):254-59 (Feb. 2005).
JANUVIA—EPAR Summary for the Public, pp. 1-3 (Aug. 2012).
Karasik et al., "Sitagliptin, a DPP-4 inhibitor for the treatment of patients with type 2 diabetes: a review of recent clinical trials," Current Medical Research and Opinion 24(2):489-96 (Jan. 2008).

(56) References Cited

OTHER PUBLICATIONS

Katz et al., "The clinical burden of type 2 diabetes in patients with acute coronary syndromes: Prognosis and implications for short- and long-term management" Diabetes and Vascular Disease Research, 11(6):395-409 (Nov. 2014).
Кондратьев В.А. Методические указания, , May 5, 2010,с. 5 (Kondrat'ev V.A. Methodical Guidelines, May 7, 2010, p. 5)] (in Russian only), found on Mar. 24, 2016, found from Internet: StudFields.ru>preview/4510743).
Lantus® 100U/ml solution for injection (insuline glargine); published in vol. 24 No. 9 of Pract. Diab. Int. Nov./Dec. 2007, p. 472.
Lantus® Drug Description, downloaded Nov. 12, 2015, one page.
Lawson et al., "Coordination of gastric and gallbladder emptying after ingestion of a regular meal." Gastroenterology. 85(4):866-70 (Oct. 1983).
Lee et al., "Goals of Glycemic Control in Frail Older Patients with Diabetes" JAMA 305(13):1350-51 (Apr. 2011).
Lepore et al., "Pharmacokinetics and pharmacodynamics of subcutaneous injection of long-acting human insulin analog glargine, NPH insulin, and ultralente human insulin and continuous subcutaneous infusion of insulin lispro." Diabetes 49(12):2142-48 (Dec. 2000).
Mac Conell et al., "Exenatide resulted in significantly greater improvements in postprandial glycaemic control compared to sitagliptin," Diabetologia 51(Supplement 1) p. S348, Abstract 872, one page (2008).
Mainous et al., "Impact of the population at risk of diabetes on projections of diabetes burden in the United States: an epidemic on the way." Diabetologia 50(5):934-40 (May 2007; Epub Nov. 21, 2006).
Matthews et al., "Homeostasis model assessment: insulin resistance and β-cell function from fasting plasma glucose and insulin concentrations in man." Diabetologia 28(7):412-419 (Jul. 1985).
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Miller et al., "Type 2 diabetes in the child and adolescent", In: Lifshitz F (ed) Pediatric Endocrinology: 5th edition, vol. 1, New York, Marcel Dekker, pp. 169-188 (2007).
Mokdad et al., "The association of body mass index with the risk of type 2 diabetes: a case-control study nested in an electronic health records system in the United States." JAMA, 289(1):76-79 (Jan. 2003).
Monnier et al., "Contribution of fasting and postprandial plasma glucose increments to the overall diurnal hyperglycemia of type 2 diabetic patients: variations with increasing levels of HbA1c." Diabetes Care 26(3):881-85 (Mar. 2003).
Mudaliar & Edelman, "Insulin therapy in type 2 diabetes." Endocrinol Metab Clin North Am. 30(4):935-82 (Dec. 2001).
Nathan et al., "Medical Management of Hyperglycemia in Type 2 Diabetes: A Consensus Algorithm for the Initiation and Adjustment of Therapy" Diabetologia 52:17-30 (2009: Epub Oct. 22, 2008).
Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-75 (Jan. 2008).
Nathan et al., "Translating the A1c Assay Into Estimated Average Glucose values." Diabetes Care 31(8):1473-78 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
NCT00715624 Clinical Trials.gov "GLP-1 Agonist AVE0010 in Patients With Type 2 Diabetes for Glycemic Control and Safety Evaluation, on Top of Basal Insulin" (updated Mar. 2, 2011), p. 1-3.
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Mar. 10, 2014, Retrieved Aug. 31, 2016, pp. 1-5.
NCT01195454, NIH Clinical Trials, "Euglycemic clamp dose-response study comparing insulin glargine U300 with Lantus U100" last updated Sep. 3, 2010, pp. 1-3.
NCT00866658 ClinicalTrials.gov, "GLP-1 agonist AVE0010 in patients with type 2 diabetes for glycemic control and safety evaluation, on top of basal insulin +/− sulfonylurea" p. 1-3, accessed Mar. 16, 2016 (updated Aug. 3, 2010).
NICE, National Institute for Health and Care Excellence, "Type 2 diabetes in adults: management" pp. 1-45 (Dec. 2, 2015).
Nihonn-Iyakuhin-shu Iryoyaku "Pioglitazone hydrochloride, Insulin sensitizing hypoglycemic agent" 2009 Edition, Jiho Inc. p. 1901 (2009).
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Osterbye et al., "Sulfatide promotes the folding of proinsulin, preserves insulin crystals, and mediates its monomerization." Glycobiology 11(6):473-79 (Jun. 2001).
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (Jan. 2011).
Petersen & Christensen et al., "Clinical potential of lixisenatide once daily treatment for type 2 diabetes mellitus" Diabetes, Metabolic Syndrome and Obesity: Targets and Therapy, 6:217-31 (Jun. 2013).
Acunman et al., "Lixisenatide protects the neurovascular unit in diabetes retinopathy" Abstract & Poster 1045; EASD meeting in Lisbon 2017, 2 pages (Sep. 11-15, 2017).
ADIS R&D Profile "Insulin Glargine: Glargine, HOE 71GT15, HOE 71GT80, HOE 901", Drugs R&D 2(2):107-109 (Aug. 1999).
Ashford & Landi, "Stabilizing Properties of Tween 80 in Dilute Protein Solutions" Bull Parenteral Drug Assoc. 20(3):74-84 (May-Jun. 1966).
Aventis SEC Form 20-F; pp. 1-303 (Apr. 8, 2002).
Bam et al., "Tween protects recombinant human growth hormone against agitation-induced damage via hydrophobic interactions" J. Ph. Sci. 87(12):1554-59 (Dec. 1998).
Bam et al., "Stability of Protein Formulations: Investigation of Surfactant Effects by a Novel EPR Spectroscopic Technique," Pharmaceutical Research, 12(1):2-11 (Jan. 1995).
Bates et al., "Kinetics of hydrolysis of polyoxyethylene (20) sorbitan fatty acid ester surfactants," J. Pharmacy and Pharmacology 25(6):470-77 (Jun. 1973).
Berchtold & Hilgenfeld, "Binding of Phenol to R6 Insulin Hexamers" Biopolymers 51(2):165-72 (1999).
Burgstaller et al., "Shedding Light on Insulin Aggregation with the Litesizer 500" Anton Paar—Application Report, pp. 1-4 (2014).
Caprio, "Obesity and Type 2 Diabetes: The Twin Epidemic" Diabetes Spectrum 16(4):230 (2003).
Chawla et al., "Aggregation of Insulin, Containing Surfactants, in Contact with Different Materials", Diabetes 34 (5):420-24 (May 1985).
Chiasson "Early Insulin Use in Type 2 Diabetes—What are the cons?" Diabetes Care 32(Suppl. 2):S270-S274 (Nov. 2009).
Colagiuri, "Diabesity: therapeutic options" Diabetes, Obesity and Metabolism 12(6):463-73 (Jun. 2010).

(56) References Cited

OTHER PUBLICATIONS

Definition of "hypoglycemia" Stedman's Medical Dictionary, 5th Edition, Japan, published on Feb. 20, 2002, p. 853; in Japanese, English translation also submitted.
Derewenda et al., "Phenol Stabilizes More Helix in a New Symmetrical Zinc Insulin Hexamer" Nature 338 (6216):594-96 (Apr. 1989).
Dietrich et al., "The DPP4 Inhibitor Linagliptin Protects from Experimental Diabetic Retinopathy" PLoS ONE 11(12): e1067853, pp. 1-17 (Dec. 2016).
Drug Facts and Comparison; J. B. Lippincot Company, St. Louis, MO; pp. 1781-1790 (1988).
Elvert et al., "Energy loss via urine and faeces—a combustive analysis in diabetic rats and the impact of antidiabetic treatment on body weight", Diabetes, Obesity and Metabolism, 15(4):324-334 (Apr. 2013).
EMEA Public Statement on INSUMAN INFUSAT (Feb. 14, 2000), at http://www.ema.europa.eu/ema/index.jsp?curl=pages/news_and_events/news/2010/08/news_detail_001094.jsp&mid=WC0b01ac058004d5c1 (accessed Jun. 1, 2017); pp. 1-2.
European Medicines Agency, LYXUMIA 10/20 micrograms solution for injection, Summary of Product Characteristics, Date of first authorisation: Feb. 1, 2013, pp. 1-82 (retrieved from the internet on Mar. 12, 2018).
Excerpts from "Handbook of Pharmaceutical Excipients" 2nd Edition (eds. A. Wade and P.J. Weller) American Pharmaceutical Association, Washington, The Pharmaceutical Press, London; pp. 1-55 (1994).
Farag & Gaballa, "Diabesity: an overview of a rising epidemic" Nephrol Dial Transplant 26(1):28-35 (Jan. 2011; Epub Nov. 2, 2010).
Gatlin & Gatlin, "Formulation and Administration Techniques to Minimize Injection Pain and Tissue Damage Associated with Parenteral Products" in Injectable Drug Development, Chapter 17; pp. 401-421 (eds. P. K. Gupta and G.A. Brazeau) (CRC Press) (1999).
Grau & Saudek, "Stable Insulin Preparation for Implanted Insulin Pumps", Diabetes 36(12):1453-59 (Dec. 1987).
Hallas-Moller, "The Lente Insulins", Diabetes 5:7-14 (Jan.-Feb. 1956).
Heile & Schneider, "The Evolution of Insulin Therapy in Diabetes Mellitus", J Fam Pract 61(5 Suppl.):S6-12 (May 2012).
Hernandez et al., "Topical Administration of GLP-1 Receptor Agonists Prevents Retinal Neurodegeneration in Experimental Diabetes" Diabetes 65:172-187 (Jan. 2016).
INSUMAN INFUSAT entry in Rote Liste, one page (2001).
INSUMAN INFUSAT; FASS Entry for INSUMAN INFUSAT; pp. 1-6 (Jan. 2000). English translation of Jun. 5, 2017, pp. 1-8 also submitted.
Jones, "Insulin Glargine Aventis Pharma", IDrugs 3(9):1081-87 (Sep. 2000).
Jones et al. "Surfactant-Stabilized Protein Formulations: A Review of Protein-Surfactant interactions and Novel Analytical Methodologies," Therapeutic Protein & Peptide Delivery, ACS Symposium Series; Chapter 12, pp. 206-222 (1997).
Katakam et al., "Effect of Surfactants on the Physical Stability of Recombinant Human Growth Hormone" J Pharm Sci 84(6):713-16 (Jun. 1995).
Lantus® entry in Physician's Desk Reference; pp. 1-6 (2001).
Lantus®—FDA Drug Approval Letter for Lantus® (NDA 02-1081) at https://www.accessdata.fda.gov/scripts/cder/daf/index.cfm?event=overview.process&ApplNo=021081 (accessed Jan. 25, 2018), pp. 1-5.
Lantus®—FDA Drug Approval Label for Lantus® (NDA 02-1081) (Apr. 20, 2000) at https://www.accessdata.fda.gov/scripts/cder/daf/index.cfm?event=overview.process&ApplNo=021081 (accessed Jan. 25, 2018), pp. 1-14.
Lee et al., "Effect of Brij-78 on Systemic Delivery of Insulin from an Ocular Device" J Pharm Sci 86(4):430-33 (Apr. 1997).
Lee et al., "Review on the Systemic Delivery of Insulin via the Ocular Route" Int'l J Pharmaceutics 233(1-2):1-18 (Feb. 2002).
Lee et al., "Epidemiology of diabetic retinopathy, diabetic macular edema and related vision loss" Eye and Vision 2:17, pp. 1-25 (2015).
Lougheed et al., "Insulin Aggregation in Artificial Delivery Systems" Diabetologia 19(1):1-9 (Jul. 1980).
Manning et al., "Stability of Protein Pharmaceuticals," Pharm Research, 6(11):903-18 (Nov. 1989).
McKeage & Goa, "Insulin Glargine: A Review of its Therapeutic Use as Long-Acting Agent for the Management of Type 1 and Type 2 Diabetes Mellitus," Drugs 61(11):1599-1624 (Sep. 2001).
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Oct. 11, 2016, Retrieved Mar. 30, 2018, pp. 1-11.
NCT00765817, Clinical Trials.gov "Addition of Exenatide to Insulin Glargine in Type 2 Diabetes Mellitus" last updated Oct. 26, 2016, last accessed Jan. 19, 2018, pp. 1-8.
NCT01572649, "Evaluation of the Blood Levels of the Drug (Lixisenatide), the Plasma Glucose Levels and Safety in Paediatric and Adult Patients with Type 2 Diabetes", last updated May 23, 2014; accessed Jul. 5, 2018, pp. 1-6.
Nowotny et al., "Advanced Glycation End Products and Oxidative Stress in Type 2 Diabetes Mellitus" Biomolecules 5:194-222 (Mar. 2015).
Owens et al., "Pharmacokinetics of 125I-labeled insulin glargine (HOE 901) in healthy men: comparison with NPH insulin and the influence of different subcutaneous injection sites." Diabetes Care 23(6):813-19 (Jun. 2000).
Regard et al., "Anatomical profiling of G protein-coupled receptor expression" Cell 135(3):561-571 (Oct. 2008).
Sanofi-aventis Press Release (Melia), "New Diabetes Compound AVE0010 Showed Clear Dose Response Results With Once-A-Day Injection in Phase IIb Study" San Francisco, California (Jun. 7, 2008) pp. 1-3.
Schmolka, "Poloxamers in the Pharmaceutical Industry" in Polymers for Controlled Drug Delivery, Chapter 10, pp. 189-214 (CRC Press) (1991).
U.S. Appl. No. 13/382,770, filed May 29, 2012, Schoettle.
U.S. Appl. No. 13/382,442, filed Feb. 21, 2012, Schoettle.
U.S. Appl. No. 13/509,507, filed Jul. 30, 2014, Brunner-Schwarz et al.
U.S. Appl. No. 13/509,542, filed Aug. 2, 2012, Hagendorf et al.
U.S. Appl. No. 14/172,151, filed Feb. 4, 2014, Bley et al.
U.S. Appl. No. 12/617,805, filed Nov. 13, 2009, Silvestre et al.
U.S. Appl. No. 12/617,811, filed Nov. 13, 2009, Silvestre et al.
U.S. Appl. No. 14/220,562, filed Mar. 20, 2014, Becker et al.
U.S. Appl. No. 13/700,631, filed Nov. 11, 2012, Becker et al.
U.S. Appl. No. 13/595,590, filed Aug. 27, 2012, Niemoller et al.
U.S. Appl. No. 13/602,913, filed Sep. 4, 2012, Hess et al.
U.S. Appl. No. 13/633,563, filed Oct. 2, 2012, Stechl et al.
U.S. Appl. No. 13/123,835, filed Sep. 30, 2011, Werner et al.
U.S. Appl. No. 13/633,496, filed Oct. 2, 2012, Stechl et al.
U.S. Appl. No. 14/303,895, filed Jun. 13, 2014, Souhami et al.
U.S. Appl. No. 14/965,586, filed Dec. 10, 2015, Souhami et al.
U.S. Appl. No. 14/995,910, filed Jan. 14, 2016, Bergmann et al.
U.S. Appl. No. 15/073,364, filed Mar. 17, 2016, Belder et al.
U.S. Appl. No. 15/068,286, filed Mar. 11, 2016, Roy et al.
U.S. Appl. No. 15/803,589, filed Nov. 3, 2017, Hagendorf et al.
U.S. Appl. No. 15/162,563, filed May 23, 2016, Becker et al.
U.S. Appl. No. 15/730,033, filed Oct. 11, 2017, Niemoller et al.
U.S. Appl. No. 15/914,197, filed Mar. 7, 2018, Souhami et al.
U.S. Appl. No. 15/893,577, filed Feb. 9, 2018, Belder et al.
Clinical Trial for History of Changes for Study: NCT00976937 dated Oct. 11, 2018, [Accessed https://clinicaltrials.gov/ct2/history/NCT00976937?v_2=View#StudyPageTop].
English translation of Notice of Final Rejection issued in KR App. No. 10-2013-7033312, dated Oct. 12, 2018.
"Diabetes" from medical information in the National Health Care Information Portal.
Ito et al. (2000) "Importance of OGTT for diagnosing diabetes mellitus based on prevalence and incidence of retinopathy," Diabetes Research and Clinical Practice, 49:181-186.

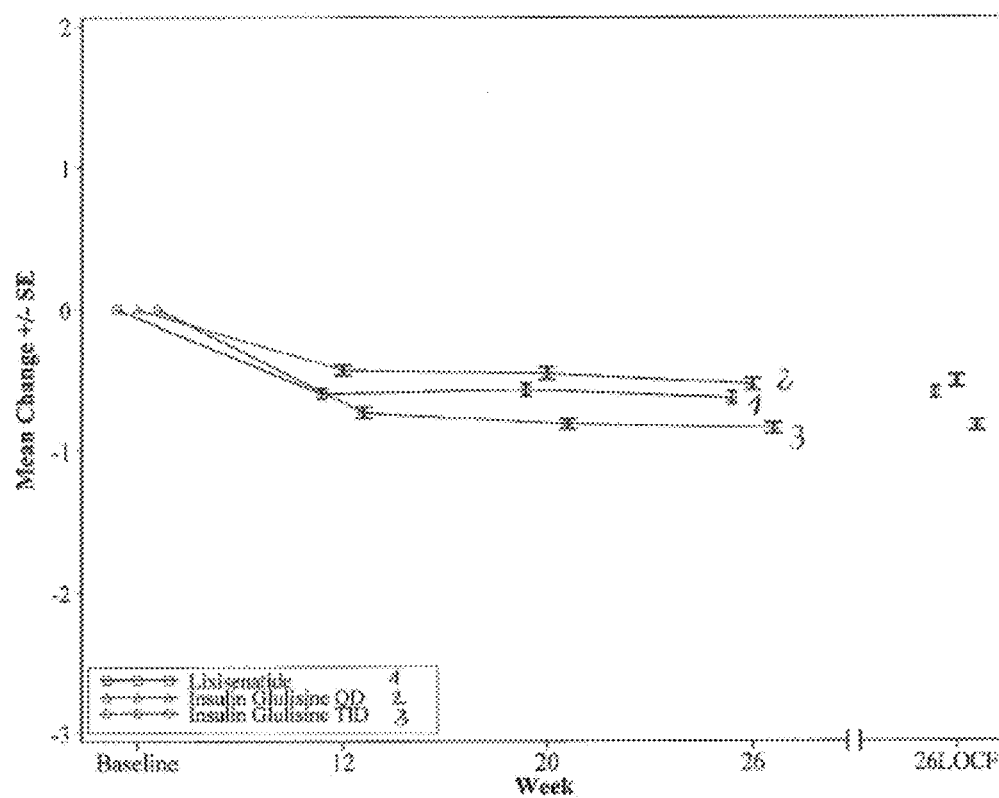
Figure 1 - mean change in HbA1c(%) from baseline by visit - mITT population
LOCF = Last observation carried forward.
Note: The plot included measurements obtained up to 14 days after the last injection of the investigational medicinal product.

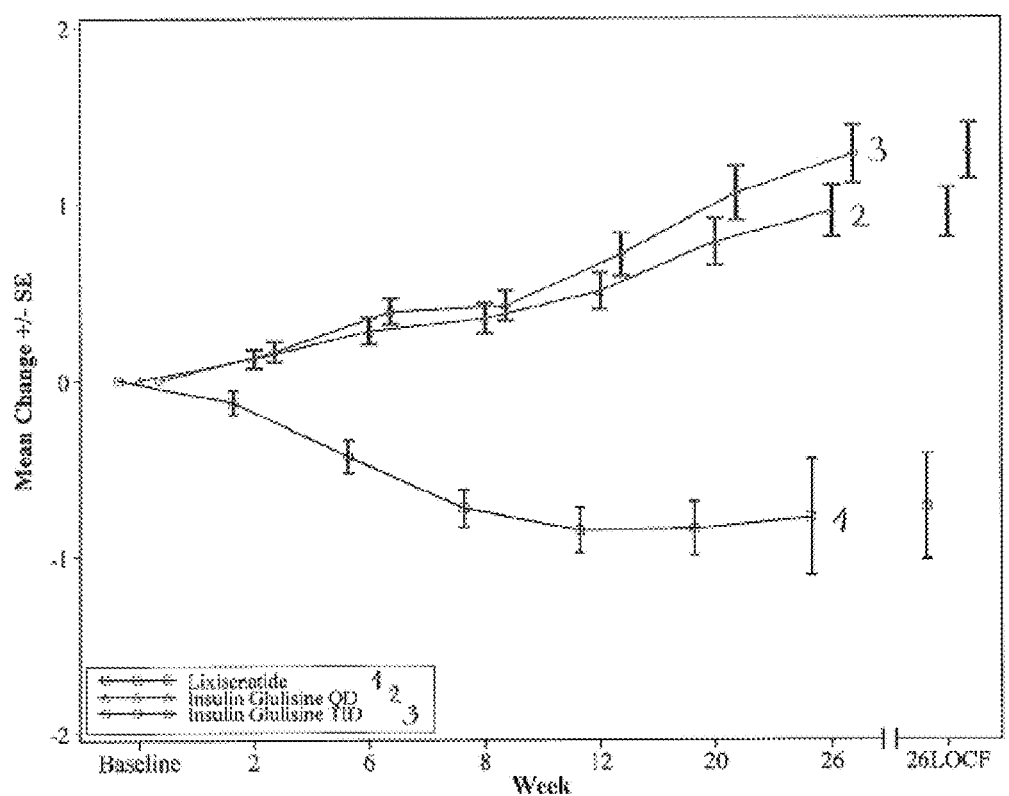
Figure 2 - mean change in body weight (kg) from baseline by visit – mITT population
LOCF = Last observation carried forward.
The analysis included measurements obtained up to 3 days after the last injection of the investigational medicinal product.

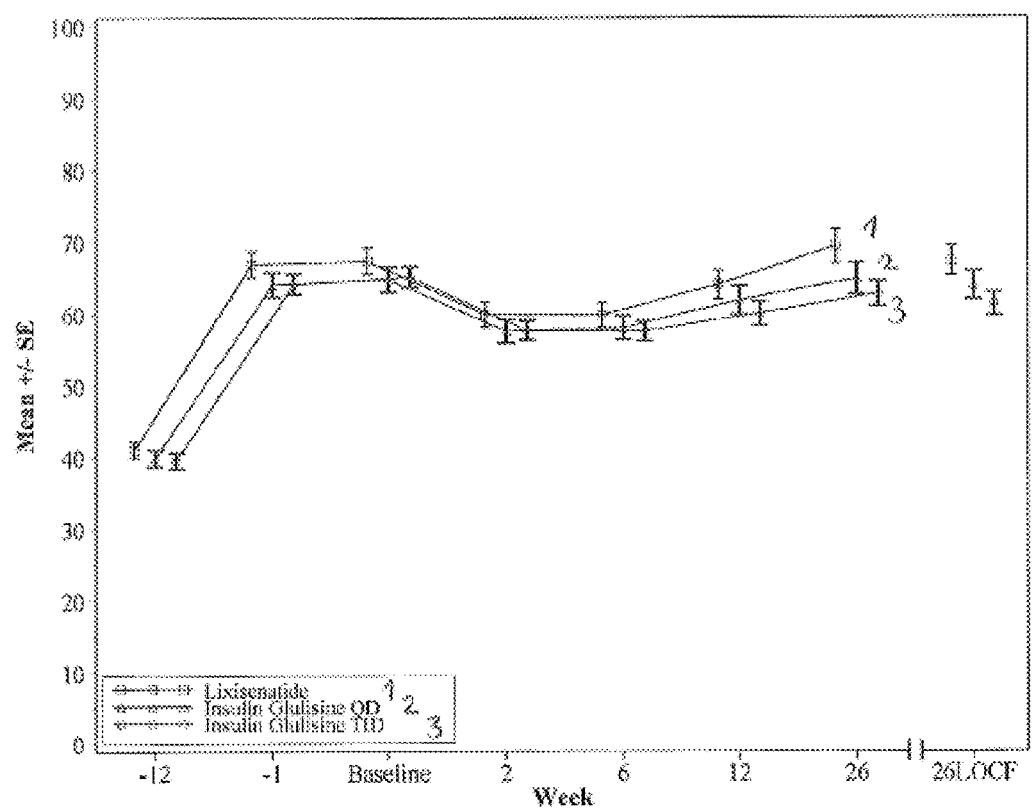

Figure 3 - mean insulin glargine daily dose (U) by visit – mITT population

LOCF = Last observation carried forward.
The analysis included measurements obtained up to the date of last injection of the investigational medicinal product.
The dose of insulin glargine are collected on 3 different days during the week prior to the visit and the values presented are the average of the collected doses except for Week -12 when the dose was collected only once for the visit.

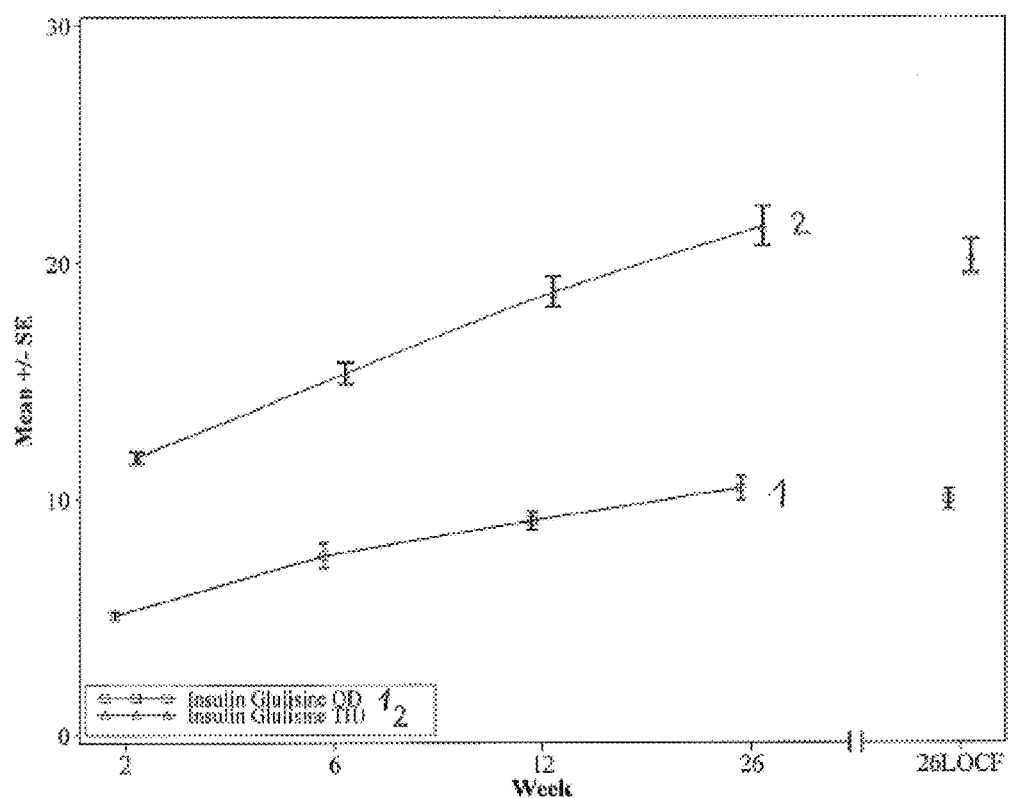

Figure 4 – mean daily insulin glulisine dose (U) by visit – mITT population

LOCF = Last observation carried forward.
The analysis included measurements obtained up to the date of last injection of the investigational medicinal product.
The insulin glulisine doses were collected on 3 different days during the week prior to the visit and the values presented are the average of the collected doses.

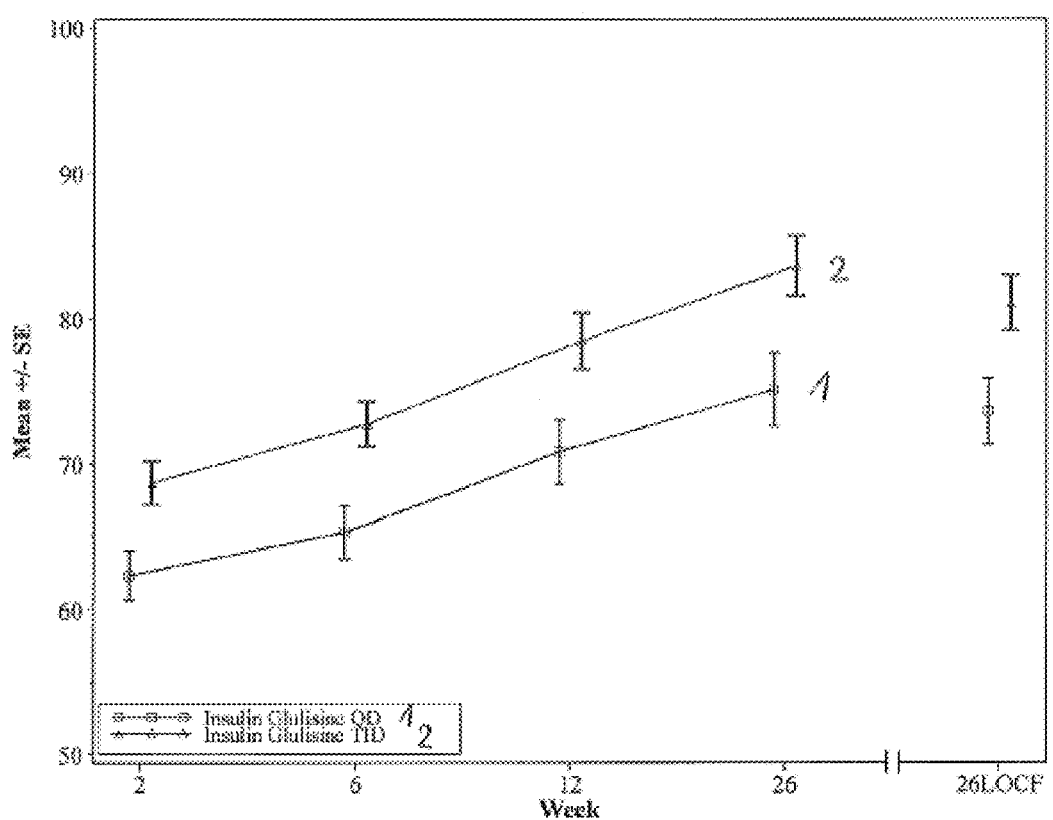
Figure 5 - mean total insulin dose (U) by visit – mITT population
LOCF = Last observation carried forward.
The analysis included measurements obtained up to the date of last injection of the investigational medicinal product.
Total insulin dose is the sum of average insulin glargine dose and average insulin glulisine dose for the visit.

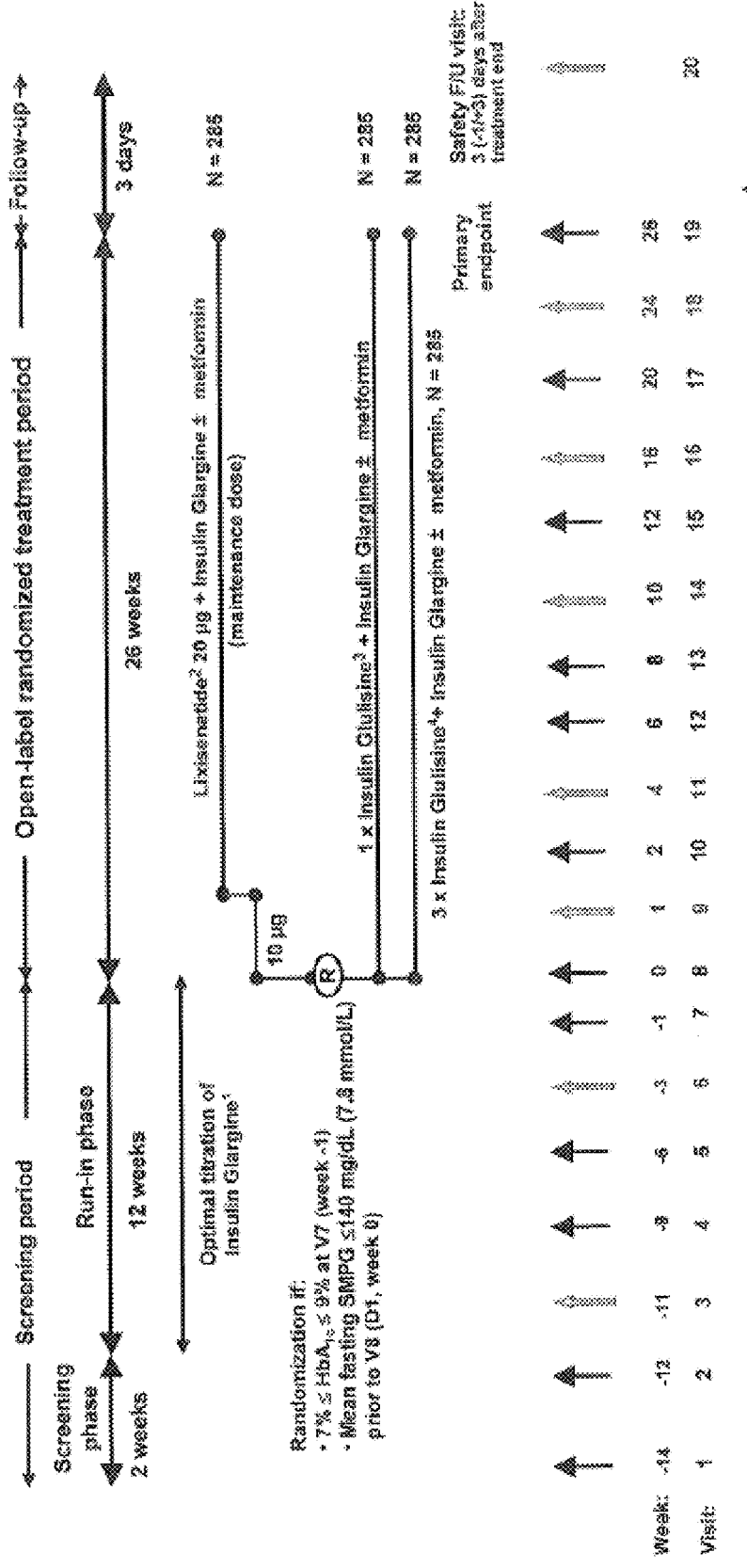

SEQUENCE LISTING

```
<160> NUMBER OF SEQ ID NOS: 2

<210> SEQ ID NO 1
<211> LENGTH: 44
<212> TYPE: PRT
<213> ORGANISM: Artificial
<220> FEATURE:
<223> OTHER INFORMATION: desPro36-Exendin-4(1-39)-Lys6-NH2

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Pro Ser
            35
```

TREATMENT TYPE 2 DIABETES MELLITUS PATIENTS

This application is a Divisional of U.S. patent application Ser. No. 15/068,286, filed Mar. 11, 2016, which claims the benefit of European Application No. 15 159 064.3, filed Mar. 13, 2015, the disclosures of which are herein incorporated by reference in their entirety.

Subject of the present invention is a pharmaceutical combination for use in glycemic control, for use in the reduction of the HbA1c value, the fasting plasma glucose or/and the 2 hour postprandial plasma glucose, for use in the prevention of weight gain or/and for inducing weight loss, for use in the reduction of the risk of hypoglycemia, in a type 2 diabetes mellitus patient, said combination comprising
  (i) lixisenatide or/and a pharmaceutically acceptable salt thereof,
  (ii) insulin glargine or/and a pharmaceutically acceptable salt thereof, and
  (iii) optionally metformin or/and a pharmaceutically acceptable salt thereof.

In a healthy person the release of insulin by the pancreas is strictly coupled to the concentration of blood glucose. An increased level of blood glucose, as appears after meals, is rapidly counterbalanced by a respective increase in insulin secretion. In fasting condition the plasma insulin level drops to a basal value which is sufficient to ensure the continuous supply of glucose to insulin-sensitive organs and tissues and to keep the hepatic glucose production at a low level at night.

In contrast to type 1 diabetes, there is not generally a lack of insulin in type 2 diabetes mellitus but in many cases, particularly in progressive cases, the treatment with insulin is regarded as the most suitable therapy, if required in combination with orally administered anti-diabetic drugs.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro and macro-vascular damages that possibly manifest themselves in retinopathies, nephropathies or neuropathies and lead to blindness, renal failure and the loss of extremities and are accompanied by an increased risk of cardiovascular diseases. It can thus be concluded that an improved therapy of diabetes primarily has to aim keeping blood glucose in the physiological range as close as possible.

A particular risk exists for overweight patients suffering from type 2 diabetes mellitus, e.g. patients with a body mass index (BMI)≥30 kg/m². In these patients the risks of diabetes overlap with the risks of overweight, leading e.g. to an increase of cardiovascular diseases compared to type 2 diabetes mellitus patients being of a normal weight.

The compound desPro³⁶Exendin-4(1-39)-Lys₆-NH₂ (AVE0010, lixisenatide) is a derivative of Exendin-4. AVE0010 is disclosed as SEQ ID NO:93 in WO 01/04156:

```
SEQ ID NO: 1: lixisenatide (44 amino acids)
H-G-E-G-T-F-T-S-D-L-S-K-Q-M-E-E-E-A-V-R-L-F-I-E-W-
L-K-N-G-G-P-S-S-G-A-P-P-S-K-K-K-K-K-K-NH₂
```

```
SEQ ID NO: 2: exendin-4 (39 amino acids)
H-G-E-G-T-F-T-S-D-L-S-K-Q-M-E-E-E-A-V-R-L-F-I-E-W-
L-K-N-G-G-P-S-S-G-A-P-P-P-S-NH₂
```

Exendins are a group of peptides which can lower blood glucose concentration. The Exendin analogue lixisenatide is characterised by C-terminal truncation of the native Exendin-4 sequence. Lixisenatide comprises six C-terminal lysine residues not present in Exendin-4.

Lixisenatide is also termed des-38-proline-exendin-4 (*Heloderma suspectum*)-(1-39)-peptidylpenta-L-lysyl-L-lysinamide (CAS number 320367-13-3). In the present invention, "lixisenatide" includes pharmaceutically acceptable salts thereof. The person skilled in the art knows suitable pharmaceutically acceptable salts of lixisenatide.

Insulin glargine is an analogue of human insulin. Insulin glargine is 31$^B$-32$^B$-Di-Arg human insulin with further substitution of asparagine in position A21 by glycine. Insulin glargine is also termed Gly(A21)-Arg(B31)-Arg(B32) human insulin. The CAS number of insulin glargine is 160337-95-1. In the present invention, "insulin glargine" includes pharmaceutically acceptable salts thereof. The person skilled in the art knows suitable pharmaceutically acceptable salts of insulin glargine.

Metformin is the international nonproprietary name of 1,1-dimethylbiguanide (CAS number 657-24-9). Metformin is a biguanide hypoglycemic agent used in the treatment of non-insulin-dependent diabetes mellitus (type 2 diabetes mellitus) not responding to dietary modification. Metformin improves glycemic control by improving insulin sensitivity and decreasing intestinal absorption of glucose. Metformin is usually administered orally. However, control of type 2 diabetes mellitus in obese patients by metformin may be insufficient. Thus, in these patients, additional measures for controlling type 2 diabetes mellitus may be required. "Metformin", as used herein, included pharmaceutically acceptable salts thereof. The person skilled in the art knows suitable pharmaceutically acceptable salts of metformin.

In the examples of the present invention, the effect of the combination of lixisenatide, insulin glargine and optionally metformin has been tested in obese type 2 diabetes mellitus patients poorly controlled with a basal insulin alone or a basal insulin in combination with one to three oral anti-diabetic drugs selected from metformin, sulfonylureas, dipeptidyl-peptidase-4 (DPP-4) inhibitors and glinides. Even by this treatment, the diabetes patients still had a fasting plasma glucose concentration of about 9.2 to 9.5 mmol/L and a HbA1c value of about 8.5%. The 2 hour postprandial plasma glucose was about 13.8 to 14.5 mmol/L (249 to 262 mg/dL). These values still exceed normoglycemic values.

Surprisingly, a reduction in fasting glucose plasma concentration to about 6.6 mmol/L (119 mg/dL) could be observed by treatment with a combination of lixisenatide, insulin glargine and optionally metformin. Reduction of body weight was statistically superior for lixisenatide in view of the comparative treatment with insulin glulisine once daily or three times daily.

Termination of the above-indicated pre-treatment and titration of insulin glargine (optionally in combination with metformin) for 12 weeks to achieve a glycemic target of 4.4 to 5.6 mmol/L in terms of fasting SMPG without recurrent or severe hypoglycemia before the onset of treatment with the combination of lixisenatide, insulin glargine and optionally metformin resulted in an initial reduction in fasting glucose plasma concentration from 9.16 mmol/L to 6.91 mmol/L and in HbA1c from 8.51% to 7.87%.

Documented hypoglycemia was numerically and significantly lower with lixisenatide in view of the comparative treatment with insulin glulisine once daily or three times daily.

In conclusion, insulin glargine combined with lixisenatide and optionally metformin may become a preferred option, attaining meaningful glycemic targets with less hypoglycemia and with weight loss compared with prandial insulin (such as insulin glulisine), as basal insulin plus oral antidiabetic compounds or basal insulin plus prandial insulin (bolus administration) in difficult to control, obese, insulin-treated type 2 diabetes mellitus patients.

A first aspect of the present invention is a pharmaceutical combination for use in glycemic control in a type 2 diabetes mellitus patient, said combination comprising
(i) lixisenatide or/and a pharmaceutically acceptable salt thereof,
(ii) insulin glargine or/and a pharmaceutically acceptable salt thereof, and
(iii) optionally metformin or/and a pharmaceutically acceptable salt thereof.

In this aspect, the type 2 diabetes mellitus to be treated preferably is not adequately controlled with compound (b) and optionally compound (c) alone.

As demonstrated by the Example disclosed herein, the combination as described herein can be used for improving glycemic control. In the present invention, "improvement of glycemic control" or "glycemic control" in particular refers to improvement of the 2 hour postprandial plasma glucose concentration, improvement of fasting plasma glucose concentration, or/and improvement of the $HbA_{1c}$ value.

In particular, "improvement of glycemic control" or "glycemic control" includes the improvement of the 2 hour postprandial plasma glucose concentration.

In particular, "improvement of glycemic control" or "glycemic control" includes the reduction of the 2 hour postprandial plasma glucose concentration. Reduction means in particular that the 2 hour postprandial plasma glucose concentration reaches normoglycemic values or at least approaches these values.

In particular, "improvement of glycemic control" or "glycemic control" includes the improvement of the fasting plasma glucose concentration.

In particular, improvement of fasting plasma glucose concentration includes the reduction of the fasting plasma glucose concentration. Reduction means in particular that the fasting plasma glucose concentration reaches normoglycemic values or at least approaches these values.

In particular, "improvement of glycemic control" or "glycemic control" includes the improvement of the $HbA_{1c}$ value.

In particular, improvement of the $HbA_{1c}$ value includes the reduction of the $HbA_{1c}$ value. Reduction of the $HbA_{1c}$ value in particular means that the $HbA_{1c}$ value is reduced below 6.5% or 7%.

Yet another aspect of the present invention is a pharmaceutical combination for use in the improvement of the HbA1c value, the fasting plasma glucose or/and the 2 hour postprandial plasma glucose in a type 2 diabetes mellitus patient, said combination comprising
(i) lixisenatide or/and a pharmaceutically acceptable salt thereof,
(ii) insulin glargine or/and a pharmaceutically acceptable salt thereof, and
(iii) optionally metformin or/and a pharmaceutically acceptable salt thereof.

In this aspect, the type 2 diabetes mellitus to be treated preferably is not adequately controlled with compound (b) and optionally compound (c) alone.

In the present invention, normoglycemic values are blood glucose concentrations of in particular 60-140 mg/dl (corresponding to 3.3 to 7.8 mmol/L). This range refers in particular to blood glucose concentrations under fasting conditions and postprandial conditions.

Criteria for a type 2 diabetes mellitus diagnosis include:
the fasting plasma glucose concentration (FPG) is ≥7.0 mmol/L (126 mg/dl), or
the post challenge plasma glucose concentration is >11.1 mmol/L (200 mg/dl), performed as described by the World Health Organization (Definition, Diagnosis and Classification of Diabetes Mellitus and its Complications. Part 1: Diagnosis and Classification of Diabetes Mellitus. WHO/NCD/NCS/99.2. Geneva; 1999), using a glucose load containing the equivalent of 75 g anhydrous glucose dissolved in water, or
symptoms of diabetes and a casual plasma glucose ≥200 mg/dl (11.1 mmol/L).

These criteria are described in the Global IDF/ISPAD Guideline for Diabetes in Childhood and Adolescence (International Diabetes Federation, ISBN 2-930229-72-1).

The diagnosis of Type 2 Diabetes should not be based on a single plasma glucose concentration. Diagnosis may require continued observation with fasting or/and postprandial blood glucose levels or/and an oral glucose tolerance test.

According to Craig (Type 2 diabetes mellitus Diabetes 2014: 15(Suppl. 20): 4-17), fasting plasma glucose (FPG) and post challenge (postload) glucose can be classified as follows:
FPG<5.6 mmol/L (100 mg/dL)=normal fasting glucose concentration.
FPG 5.6 to 6.9 mmol/L (100-125 mg/dL)=impaired fasting glucose concentration.
FPG≥7.0 mmol/L (126 mg/dL)=provisional diagnosis of diabetes (the diagnosis must be confirmed, as described above)

The corresponding categories when the Oral Glucose Tolerance Test (OGTT) is used, are as follows:
Two hour postload glucose <7.8 mmol/L (140 mg/dL)= normal glucose tolerance.
Two hour postload glucose 7.8 to <11.1 mmol/L (140-200 mg/dL)=impaired glucose tolerance.
Two hour postload glucose ≥11.1 mmol/L (200 mg/dL)= provisional diagnosis of diabetes (the diagnosis must be confirmed, as described above).

Impaired glucose tolerance (IGT) and impaired fasting glucose concentration (IFG) are intermediate stages in the natural history of disordered carbohydrate metabolism between normal glucose homeostasis and diabetes.

In the present invention, normoglycemic values of fasting plasma glucose are blood glucose concentrations of in particular <5.6 mmol/L.

In the present invention, normoglycemic values of postprandial plasma glucose, as defined herein, are blood glucose concentrations of in particular <7.8 mmol/L.

In the present invention, "not adequately controlled" by a particular anti-diabetic treatment means that this treatment is not sufficient to remove the symptoms of type 2 diabetes mellitus. In particular, "not adequately controlled" by this treatment means that the patient does not reach normoglycemic values in terms of, for example, 2 hour postprandial plasma glucose concentration, HbA1c value or/and fasting plasma glucose concentration.

The type 2 diabetes mellitus patient to be treated according to the present invention may be a subject suffering from type 2 diabetes mellitus, wherein type 2 diabetes mellitus is not adequately controlled by treatment with a basal insulin monotherapy.

The type 2 diabetes mellitus patient to be treated according to the present invention may be a subject suffering from type 2 diabetes mellitus, wherein type 2 diabetes mellitus is not adequately controlled by treatment with a combination of a basal insulin and metformin alone, for instance with (a) a dose of at least 1.0 g/day metformin or at least 1.5 g/day metformin for at least 3 months, or/and (b) a dose of at the maximum 2.0 g/day metformin for at least 3 months or at the maximum 3.5 g/day metformin for at least 3 months.

The type 2 diabetes mellitus patient to be treated according to the present invention may be a subject suffering from type 2 diabetes mellitus, wherein the type 2 diabetes mellitus to be treated is not adequately controlled with compound (b) and optionally compound (c) alone.

By the treatment according to the present invention, adequate control of type 2 diabetes mellitus may be achieved in type 2 diabetes mellitus patients not adequately controlled by a particular treatment, as described herein.

"Basal insulin", as used herein, includes insulin glargine, insulin detemir and isophane insulin (NPH insulin). The basal insulin is in particular selected from insulin glargine, insulin detemir and isophane insulin (NPH insulin).

As used herein, "to be treated according to the present invention", "treatment according to the present invention", or "therapy according to the present invention" relates to the treatment of a type 2 diabetes mellitus patient by the pharmaceutical combination comprising
(i) lixisenatide or/and a pharmaceutically acceptable salt thereof,
(ii) insulin glargine or/and a pharmaceutically acceptable salt thereof, and
(iii) optionally metformin or/and a pharmaceutically acceptable salt thereof,
as described herein.

A further aspect of the present invention is a pharmaceutical combination for use in the prevention of weight gain or/and for inducing weight loss, in a type 2 diabetes mellitus patient, said combination comprising
(i) lixisenatide or/and a pharmaceutically acceptable salt thereof,
(ii) insulin glargine or/and a pharmaceutically acceptable salt thereof, and
(iii) optionally metformin or/and a pharmaceutically acceptable salt thereof.

In this aspect, the type 2 diabetes mellitus to be treated preferably is not adequately controlled with compound (b) and optionally compound (c) alone.

The examples of the present invention demonstrate that the claimed combination can reduce body weight in type 2 diabetes patients, as defined herein, wherein the comparative treatment (insulin glulisine once daily or three times daily) induces a significant weight gain.

Yet another aspect of the present invention is a pharmaceutical combination for use in the reduction of the risk of hypoglycemia, in a type 2 diabetes mellitus patient, said combination comprising
(i) lixisenatide or/and a pharmaceutically acceptable salt thereof,
(ii) insulin glargine or/and a pharmaceutically acceptable salt thereof, and
(iii) optionally metformin or/and a pharmaceutically acceptable salt thereof.

In this aspect, the type 2 diabetes mellitus to be treated preferably is not adequately controlled with compound (b) and optionally compound (c) alone.

The examples of the present invention demonstrate that documented hypoglycemia was numerically and significantly lower with the claimed combination in view of the comparative treatment with insulin glulisine once daily or three times daily.

Hypoglycemia is the critical limiting factor in the glycemic management of diabetes in both the short and long term. Despite steady improvements in the glycemic management of diabetes, population-based data indicate that hypoglycemia continues to be a major problem for people with both type 1 and type 2 diabetes (American diabetes association, workgroup on hypoglycemia: Defining and Reporting Hypoglycemia in Diabetes. Diabetes Care 28(5), 2005, 1245-1249).

The combination of the present invention can prevent hypoglycemia when administered to a type 2 diabetes mellitus patient, as described herein. "Prevention of hypoglycemia" includes reduction of the number of hypoglycemic events and/or the severity of hypoglycemia events. The combination as described herein is suitable for use in the prevention of hypoglycemia.

In the present invention, hypoglycemia is a condition wherein a type 2 diabetes mellitus patient experiences a plasma glucose concentration of below 70 mg/dL (or below 3.9 mmol/L), below 60 mg/dL (or below 3.3 mmol/L), below 54 mg/dL (or below 3.0 mmol/L), below 50 mg/dL, below 40 mg/dL, or below 36 mg/dL.

In the present invention, "symptomatic hypoglycemia" or "symptomatic hypoglycemic event" is a condition associated with a clinical symptom that results from the hypoglycemia, wherein the plasma glucose concentration can be below 70 mg/dL (or below 3.9 mmol/L), below 60 mg/dL (or below 3.3 mmol/L), below 54 mg/dL (or below 3.0 mmol/L), below 50 mg/dL, or below 40 mg/dL. A clinical symptom can be, for example, sweating, palpitations, hunger, restlessness, anxiety, fatigue, irritability, headache, loss of concentration, somnolence, psychiatric disorders, visual disorders, transient sensory defects, transient motor defects, confusion, convulsions, and coma. In the present invention, one or more clinical symptoms of symptomatic hypoglycemia, as indicated herein, can be selected. Symptomatic hypoglycemia may be associated with prompt recovery after oral carbohydrate administration. A symptomatic hypoglycemia event preferably has a plasma glucose concentration of below 60 mg/dL (or below 3.3 mmol/L).

In the present invention, "severe symptomatic hypoglycemia" or "severe symptomatic hypoglycemic event" is a condition with a clinical symptom, as indicated herein, that results from hypoglycemia, wherein the plasma glucose concentration can be below 70 mg/dL (or below 3.9 mmol/L), below 54 mg/dL (or below 3.0 mmol/L) or below 36 mg/dL (or below 2.0 mmol/L). Severe symptomatic hypoglycemia can be associated with acute neurological impairment resulting from the hypoglycemic event. In a severe symptomatic hypoglycemia, the patient may require the assistance of another person to actively administer carbohydrate, glucagon, or other resuscitative actions. These episodes may be associated with sufficient neuroglycopenia to induce seizure, unconsciousness or coma. Plasma glucose measurements may not be available during such an event, but neurological recovery attributable to the restoration of plasma glucose to normal is considered sufficient evidence that the event was induced by a low plasma glucose concentration. A severe symptomatic hypoglycemia event preferably has a plasma glucose concentration of below 36 mg/dL (or below 2.0 mmol/L).

The definition of severe symptomatic hypoglycemia may include all episodes in which neurological impairment is severe enough to prevent self-treatment and which were thus thought to place patients at risk for injury to themselves or others. The acute neurological impairment may be at least one selected from somnolence, psychiatric disorders, visual disorders, transient sensory defects, transient motor defects, confusion, convulsions, and coma. "Requires assistance" means that the patient could not help himself or herself. Assisting a patient out of kindness, when assistance is not required, should not be considered a "requires assistance" incident.

Severe symptomatic hypoglycemia may be associated with prompt recovery after oral carbohydrate, intravenous glucose, or/and glucagon administration.

In the present invention, "documented symptomatic hypoglycemia" or "documented symptomatic hypoglycemic event" is an event during which typical symptoms of hypoglycemia accompanied by a measured plasma glucose concentration of ≤70 mg/dL (≤3.9 mmol/L), or less than or equal to 54 mg/dL (≤3.0 mmol/L). Clinical symptoms that are considered to result from a hypoglycemic episode are, e.g., increased sweating, nervousness, asthenia/weakness, tremor, dizziness, increased appetite, palpitations, headache, sleep disorder, confusion, seizures, unconsciousness, coma.

In the present invention, "asymptomatic hypoglycemia" or "asymptomatic hypoglycemic event" is an event not accompanied by typical symptoms of hypoglycemia but with a measured plasma glucose concentration less than or equal to 70 mg/dL (3.9 mmol/L), or less than or equal to 54 mg/dL (3.0 mmol/L).

In the present invention, "probable symptomatic hypoglycemia" or "probable symptomatic hypoglycemic event" is an event during which symptoms of hypoglycemia are not accompanied by a plasma glucose determination, but was presumably caused by a plasma glucose concentration less than or equal to 70 mg/dL (or less than or equal to 3.9 mmol/L), or less than or equal to 54 mg/dL (or less than or equal to 3.0 mmol/L); symptoms treated with oral carbohydrate without a test of plasma glucose.

In the present invention, "relative hypoglycemia" or "relative hypoglycemic event" is an event during which the person with diabetes reports any of the typical symptoms of hypoglycemia, and interprets the symptoms as indicative of hypoglycemia, but with a measured plasma glucose concentration greater than 70 mg/dL (or greater than 3.9 mmol/L).

In the present invention, the hypoglycemia can be a symptomatic hypoglycemia, a severe symptomatic hypoglycemia, a documented symptomatic hypoglycemia, a probable symptomatic hypoglycemia, a relative symptomatic hypoglycemia, or an asymptomatic hypoglycemia. Preferred is a symptomatic hypoglycemia, more preferably a severe symptomatic hypoglycemia.

"Reducing the risk of hypoglycemia", as used herein, can include reducing the incidence of hypoglycemia. The incidence of hypoglycemia per patient year can be computed per patient as: 365.25× (number of episodes of hypoglycemia)/ (number of days exposed) and summarized by type of event and treatment group. "Reducing the risk of hypoglycemia", as used herein, can further include prevention of hypoglycemia in a patient, when the formulation described herein is administered to a type 2 diabetes mellitus patient, as described herein. "Reducing the risk of hypoglycemia", as used herein, can further include reduction of the number of hypoglycemic events, and/or the severity of hypoglycemia events.

The type 2 diabetes mellitus patient suffering from type 2 diabetes mellitus to be treated according to the present invention may be obese. A patient can be considered as obese if the body mass index is at least 30 kg/m$^2$. In the present invention, an obese type 2 diabetes mellitus patient may have a body mass index of at least 30 kg/m$^2$. The obese type 2 diabetes mellitus patient may have a body weight of at least 87 kg, at least 88 kg, at least 89 kg or at least 90 kg. The type 2 diabetes mellitus patient may be obese prior to the onset of therapy with the combination according to the present invention.

The patient to be treated may have an age of less than 50 years. The patient may also have an age of at least 50 years, or an age in the range of 50 to 64 years. The patient may also have an age of at least 65 years, or an age in the range of 65 to 74 years. The patient may also have an age of at least 75 years. It is preferred that the patient has an age of at least 65 years.

The type 2 diabetes mellitus to be treated according to the present invention may suffer from a type 2 diabetes mellitus not adequately controlled with a basal insulin monotherapy or a basal insulin and one to three oral anti-diabetics alone selected from the group consisting of metformin, a sulfonylurea, a DPP-4 inhibitor or a glinide alone. In this context, the basal insulin is in particular selected from insulin glargine, insulin detemir and isophane insulin (NPH insulin). In addition, this type 2 diabetes mellitus to be treated preferably is not adequately controlled with compound (b) and optionally compound (c) alone.

The type 2 diabetes mellitus patient to be treated according to the present invention may have a fasting plasma glucose of at least 9 mmol/L or at least 9.5 mmol/L when treated with a basal insulin monotherapy or a basal insulin and one to three oral anti-diabetics alone selected from the group consisting of metformin, a sulfonylurea, a DPP-4 inhibitor or a glinide alone. In particular, the patient may have this fasting plasma glucose of at least 9 mmol/L L or at least 9.5 mmol/L prior to the onset of therapy with the combination according to the present invention. In this context, the basal insulin is in particular selected from insulin glargine, insulin detemir and isophane insulin (NPH insulin). In addition, this type 2 diabetes mellitus to be treated preferably is not adequately controlled with compound (b) and optionally compound (c) alone.

Prior to the onset of therapy with the combination according to the present invention, the patient may have a fasting plasma glucose in the range of 5.6 to 6.9 mmol/L when treated with compound (b) and optionally compound (c) alone. This range can be considered to be an impaired fasting plasma glucose concentration.

Prior to the onset of therapy with the combination according to the present invention, the patient may have a fasting plasma glucose of at least 6.6 mmol/L, at least 6.7 mmol/L, at least 6.8 mmol/L or at least 6.9 mmol/L, when treated with compound (b) and optionally compound (c) alone.

The type 2 diabetes mellitus patient to be treated according to the present invention may have a HbA1c of at least 8.5% when treated with a basal insulin monotherapy or a basal insulin and one to three oral anti-diabetics alone selected from the group consisting of metformin, a sulfonylurea, a DPP-4 inhibitor or a glinide alone. In particular, the patient may have this a HbA1c of at least 8.5% prior to the onset of therapy with the combination according to the present invention. In this context, the basal insulin is in particular selected from insulin glargine, insulin detemir and isophane insulin (NPH insulin). In addition, this type 2 diabetes mellitus to be treated preferably is not adequately controlled with compound (b) and optionally compound (c) alone.

Prior to the onset of therapy with the combination according to the present invention, the patient may have a HbA1c of at least 7.5% or at least 7.8% when treated with compound (b) and optionally compound (c) alone.

In particular, the patient to be treated according to the present invention does not receive concomitant treatment with at least one of a sulfonylurea, a DPP-4 inhibitor and a glinide.

In particular, in the patient to be treated according to the present invention, the type 2 diabetes mellitus has been diagnosed for at least 1 year or at least 2 years prior to the onset of a therapy according to the present invention.

The administration of the combination according to the present invention can comprise the steps:
(i) administration of compounds (b) and (c) for at least 4 weeks, and
(ii) continuing treatment by administration of compounds (a), (b) and (c),
wherein the amount of compound (b) to be administered in steps (i) or/and (ii) is adjusted (titrated) so that a predetermined fasting plasma glucose level or/and a predetermined self-monitored plasma glucose level is reached or at least approximated. In particular, adjustment (titration) of compound (b) is performed in steps (i).

In step (i), the compounds (b) and (c) of the pharmaceutical combination of the present invention may be administered for at least 4 weeks, at least 8 weeks, at least 12 weeks, or at least 16 weeks. Preferably, step (i) comprises administration of compounds (b) and (c) for at least about 12 weeks.

Step (i) may be performed for at the maximum about 8 weeks, at the maximum about 12 weeks, at the maximum about 16 weeks, at the maximum about 20 weeks, or at the maximum about 24 weeks. Preferred is a duration of step (i) of about 12 weeks.

Step (i) may be performed with the proviso that compound (a) is not administered. As demonstrated by the Example of the present invention, a treatment with a combination of insulin glargine, lixisenatide and optionally metformin can improve fasting plasma glucose concentration, $HbA_{1c}$ value, body weight and the risk of hypoglycemia if the treatment starts with administration of insulin glargine and optionally metformin alone. By this treatment protocol, the dose of insulin glargine can be reduced.

In the pharmaceutical composition of the present invention, the amount of compound (b) to be administered in steps (i) or/and (ii) is adjusted so that a predetermined fasting plasma glucose level or/and a predetermined self-monitored plasma glucose level is reached or at least approximated. The amount of compound (b) to be administered in steps (i) or/and (ii) may be adjusted on the basis of daily measurements of plasma glucose concentration. In particular the amount of compound (b) to be administered in steps (i) or/and (ii) may adjusted so that
(I) a fasting plasma glucose level or/and a fasting self-monitored plasma glucose level of about 4.4 mmol/l to about 5.6 mmol/l, or/and
(II) a self-monitored plasma glucose level (SMPG) of about 7.8 mmol/l (or about 140 mg/dl) or less
is reached or at least approximated.

"Self-monitored plasma glucose (SMPG)", as used herein, can be the "4-point Self Monitored Plasma Glucose" or the "7-point Self Monitored Plasma Glucose". The 4 point and 7-point Self Monitored Plasma Glucose value are in particular average plasma glucose concentrations including fasting and postprandial conditions.

"4-point Self Monitored Plasma Glucose" in particular refers to the measurement of plasma glucose four times a day and calculation of the average plasma glucose concentration therefrom. In particular, the 4-point Self Monitored Plasma Glucose measurements are performed pre-breakfast, post-breakfast, pre-dinner, and post-dinner.

"7-point Self Monitored Plasma Glucose" in particular refers to the measurement of plasma glucose seven times a day and calculation of the average plasma glucose concentration therefrom. In particular, the 7-point Self Monitored Plasma Glucose measurements are performed pre-breakfast, post-breakfast, pre-lunch, post-lunch, pre-dinner, post-dinner and at bed-time.

The "fasting self-monitored plasma glucose (SMPG)", as used herein, is measured by the patient before breakfast, in particular before insulin glargine or/and lixisenatide injection and optional intake of metformin.

In the present invention, a type 2 diabetes mellitus patient may have a HbA1c value in the range of 7% to 10%. In particular the type 2 diabetes mellitus patient to be treated may have a $HbA_{1c}$ value of at least about 7%, at least about 7.5%, at least about 7.8%, at least about 8%, at least about 8.5%, or at least about 9%. These values exceed normoglycemic values, indicating that the type 2 diabetes mellitus is not adequately controlled if treated with an antidiabetic compound, as described herein.

The type 2 diabetes mellitus patient to be treated according to the present invention may have a 2 hours postprandial plasma glucose concentration of at least 11.1 mmol/L, at least 12 mmol/L, at least 13 mmol/L, at least 13.5 mmol/L or at least 14 mmol/L. These plasma glucose concentrations exceed normoglycemic concentrations, indicating that the type 2 diabetes mellitus is not adequately controlled if treated with an antidiabetic compound, as described herein.

"Postprandial" is a term that is well known to a person skilled in the art of diabetology. The term "postprandial" describes in particular the phase after an ingestion of a meal or/and exposure to glucose under experimental conditions. In a healthy person this phase is characterised by an increase and subsequent decrease in blood glucose concentration. The postprandial phase typically ends up to 2 h after a meal or/and exposure to glucose (2 h postprandial plasma glucose concentration).

Determination of postprandial plasma glucose is well-known (see, e.g. Crapo et al., Diabetes, 1977, 26(12):1178-1183).

The type 2 diabetes mellitus patient to be treated according to the invention may have a fasting plasma glucose concentration of at least 8 mmol/L, at least 8.5 mmol/L, at least 9 mmol/L, or at least 9.5 mmol/L. These plasma glucose concentrations exceed normoglycemic concentrations, indicating that the type 2 diabetes mellitus is not adequately controlled if treated with an antidiabetic compound, as described herein.

In the present invention, metformin can be administered according to commonly known administration protocols of metformin in accordance with the terms of marketing authorization. For example, metformin can be administrated once daily, twice daily or three times a day. In particular, the metformin dose applied before the onset of the therapy as disclosed herein is continued in combination with (a) lixisenatide or/and a pharmaceutically acceptable salt thereof, and (b) insulin glargine or/and a pharmaceutically acceptable salt thereof, as disclosed herein.

In the present invention, metformin may be administered orally. The skilled person knows formulations of metformin suitable for treatment of type 2 diabetes mellitus by oral administration. Metformin may be administered to a type 2 diabetes mellitus patient in need thereof, in an amount sufficient to induce a therapeutic effect. Metformin may be administered in a dose of at least 1.0 g/day or at least 1.5 g/day. Metformin may be administered in a dose of at the maximum of 2.0 g/day or at the maximum of 3.5 g/day. The daily metformin dose can be divided into two or three separate doses. For oral administration, metformin may be formulated in a solid dosage form, such as a tablet or pill. Metformin may be formulated with suitable pharmaceutically acceptable carriers, adjuvants, or/and auxiliary substances.

In the present invention, lixisenatide or/and a pharmaceutically acceptable salt may be administered in an add-on therapy to administration of insulin glargine and optionally metformin.

In the present invention, the terms "add-on", "add-on treatment" and "add-on therapy" relate to treatment according to the present invention with insulin glargine and lixisenatide, and optionally metformin. Metformin, insulin glargine or/and lixisenatide each may be administered in a once-a-day-dosage. Metformin, insulin glargine and lixisenatide may be administered by different administration routes. Metformin may be administered orally, and lixisenatide and insulin glargine may be administered parenterally.

In particular, "add-on", "add-on treatment" and "add-on therapy" mean that the dose of metformin administered before the onset of the treatment according to the present invention, as disclosed herein, can be continued in the treatment of the present invention.

In the present invention, lixisenatide includes pharmaceutically acceptable salts thereof. The person skilled in the art knows suitable pharmaceutically acceptable salts of lixisenatide. A preferred pharmaceutically acceptable salt of lixisenatide employed in the present invention is the acetate salt of lixisenatide.

In the present invention, lixisenatide or/and the pharmaceutically acceptable salt thereof may be administered to a type 2 diabetes mellitus patient in need thereof, in an amount sufficient to induce a therapeutic effect.

In the present invention, lixisenatide or/and the pharmaceutically acceptable salt thereof may be formulated with suitable pharmaceutically acceptable carriers, adjuvants, or/and auxiliary substances.

Lixisenatide or/and a pharmaceutically acceptable salt thereof may be administered parenterally, e.g. by injection (such as by intramuscular or by subcutaneous injection). Suitable injection devices, for instance the so-called "pens" comprising a cartridge comprising the active ingredient, and an injection needle, are known. Lixisenatide or/and a pharmaceutically acceptable salt thereof may be administered in a suitable amount, for instance in an amount in the range of 10 µg to 20 µg per dose.

In the present invention, lixisenatide or/and a pharmaceutically acceptable salt thereof may be administered in a daily dose in the range of 10 µg to 20 µg. Lixisenatide or/and a pharmaceutically acceptable salt thereof may be administered by one injection per day. Lixisenatide or/and a pharmaceutically acceptable salt thereof may be administered about 30 min before breakfast.

In the present invention, lixisenatide or/and a pharmaceutically acceptable salt thereof may be provided in a liquid composition, which preferably is an aqueous formulation. It is preferred that the liquid composition is suitable for parenteral administration, in particular for injection. The skilled person knows such liquid compositions of lixisenatide. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition comprising lixisenatide or/and a pharmaceutically acceptable salt thereof may comprise a suitable preservative. A suitable preservative may be selected from phenol, m-cresol, benzyl alcohol and p-hydroxybenzoic acid ester. A preferred preservative is m-cresol.

The liquid composition comprising lixisenatide or/and a pharmaceutically acceptable salt thereof may comprise a tonicity agent. A suitable tonicity agent may be selected from glycerol, lactose, sorbitol, mannitol, glucose, NaCl, calcium or magnesium containing compounds such as $CaCl_2$. The concentration of glycerol, lactose, sorbitol, mannitol and glucose may be in the range of 100-250 mM. The concentration of NaCl may be up to 150 mM. A preferred tonicity agent is glycerol.

The liquid composition comprising lixisenatide or/and a pharmaceutically acceptable salt thereof may comprise methionine from 0.5 µg/mL to 20 µg/mL, preferably from 1 µg/ml to 5 µg/ml. Preferably, the liquid composition comprises L-methionine.

In the present invention, insulin glargine or/and a pharmaceutically acceptable salt thereof may be provided in a liquid composition, which preferably is an aqueous formulation. It is preferred that the liquid composition is suitable for parenteral administration, in particular for injection. The skilled person knows such liquid compositions of insulin glargine.

Surfactants can be added to pharmaceutical formulation comprising insulin glargine, for example, inter alia, non-ionic surfactants. In particular, pharmaceutically customary surfactants are preferred, such as, for example: partial and fatty acid esters and ethers of polyhydric alcohols such as of glycerol, sorbitol and the like (Span®, Tween®, in particular Tween® 20 and Tween® 80, Myrj®, Brij®), Cremophor® or poloxamers. The surfactants are present in the pharmaceutical composition in a concentration of 5-200 µg/ml, preferably of 5-120 µg/ml and particularly preferably of 20-75 µg/ml.

The formulation comprising insulin glargine or/and a pharmaceutically acceptable salt thereof can additionally contain preservatives (e.g. phenol, m-cresol, p-cresol, parabens), isotonic agents (e.g. mannitol, sorbitol, lactose, dextrose, trehalose, sodium chloride, glycerol), buffer substances, salts, acids and alkalis and also further excipients. These substances can in each case be present individually or alternatively as mixtures.

Glycerol, dextrose, lactose, sorbitol and mannitol can be present in the pharmaceutical formulation comprising insulin glargine or/and a pharmaceutically acceptable salt thereof in a concentration of 100-250 mM, NaCl in a concentration of up to 150 mM. Buffer substances, such as, for example, phosphate, acetate, citrate, arginine, glycylglycine or TRIS (i.e. 2-amino-2-hydroxymethyl-1,3-propanediol) buffer and corresponding salts, can be present in a concentration of 5-250 mM, preferably 10-100 mM. Further excipients can be, inter alia, salts or arginine.

The zinc concentration of the formulation comprising insulin glargine or/and a pharmaceutically acceptable salt thereof is in the range of the concentration which is reached by the presence of 0-1000 µg/mL, preferably 20-400 µg/mL zinc, most preferably 90 µg/mL. However, the zinc may be present in form of zinc chloride, but the salt is not limited to be zinc chloride.

In the pharmaceutical formulation comprising insulin glargine or/and a pharmaceutically acceptable salt thereof glycerol and/or mannitol can be present in a concentration of 100-250 mmol/L, and/or NaCl is preferably present in a concentration of up to 150 mmol/L.

In the pharmaceutical formulation comprising insulin glargine or/and a pharmaceutically acceptable salt thereof a buffer substance can be present in a concentration of 5-250 mmol/L.

Insulin glargine or/and a pharmaceutically acceptable salt thereof can be present in the pharmaceutical formulation in a concentration of 60-6000 nmol/ml, preferably 240-3000 nmol/ml.

The pH of the formulation comprising insulin glargine or/and a pharmaceutically acceptable salt thereof can be in the range of pH 1-6.8, preferably pH 3.5-6.8, more preferred pH 3.5-4.5, even more preferred pH 4.0-4.5.

Yet another aspect of the present invention is the use of a combination comprising
 (a) lixisenatide or/and a pharmaceutically acceptable salt thereof,
 (b) insulin glargine or/and a pharmaceutically acceptable salt thereof, and
 (c) optionally metformin or/and a pharmaceutically acceptable salt thereof,
for the manufacture of a medicament for glycemic control in a type 2 diabetes mellitus patient, wherein the type 2 diabetes mellitus to be treated preferably is not adequately controlled with compound (b) and optionally compound (c) alone. In this aspect, the patient may be a patient as defined herein.

Yet another aspect of the present invention is the use of a combination comprising
 (a) lixisenatide or/and a pharmaceutically acceptable salt thereof,
 (b) insulin glargine or/and a pharmaceutically acceptable salt thereof, and
 (c) optionally metformin or/and a pharmaceutically acceptable salt thereof,
for the manufacture of a medicament for the improvement of the HbA1c value, the fasting plasma glucose or/and the 2 hour postprandial plasma glucose in a type 2 diabetes mellitus patient, wherein the type 2 diabetes mellitus to be treated preferably is not adequately controlled with compound (b) and optionally compound (c) alone. In this aspect, the patient may be a patient as defined herein.

Yet another aspect of the present invention is the use of a combination comprising
 (a) lixisenatide or/and a pharmaceutically acceptable salt thereof,
 (b) insulin glargine or/and a pharmaceutically acceptable salt thereof, and
 (c) optionally metformin or/and a pharmaceutically acceptable salt thereof,
for the manufacture of a medicament for the prevention of weight gain or/and for inducing weight loss in a type 2 diabetes mellitus patient, wherein the type 2 diabetes mellitus to be treated preferably is not adequately controlled with compound (b) and optionally compound (c) alone. In this aspect, the patient may be a patient as defined herein.

Yet another aspect of the present invention is the use of a combination comprising
 (a) lixisenatide or/and a pharmaceutically acceptable salt thereof,
 (b) insulin glargine or/and a pharmaceutically acceptable salt thereof, and
 (c) optionally metformin or/and a pharmaceutically acceptable salt thereof,
for the manufacture of a medicament for the reduction of the risk of hypoglycemia in a type 2 diabetes mellitus patient, wherein the type 2 diabetes mellitus to be treated preferably is not adequately controlled with compound (b) and optionally compound (c) alone. In this aspect, the patient may be a patient as defined herein.

Yet another aspect of the present invention is method for glycemic control in a type 2 diabetes mellitus patient, said method comprising administration of a combination comprising
 (a) lixisenatide or/and a pharmaceutically acceptable salt thereof,
 (b) insulin glargine or/and a pharmaceutically acceptable salt thereof, and
 (c) optionally metformin or/and a pharmaceutically acceptable salt thereof,
wherein the type 2 diabetes mellitus to be treated preferably is not adequately controlled with compound (b) and optionally compound (c) alone. In this aspect, the patient may be a patient as defined herein.

Yet another aspect of the present invention is method for the improvement of the HbA1c value, the fasting plasma glucose or/and the 2 hour postprandial plasma glucose in a type 2 diabetes mellitus patient, said method comprising administration the use of a combination comprising
 (a) lixisenatide or/and a pharmaceutically acceptable salt thereof,
 (b) insulin glargine or/and a pharmaceutically acceptable salt thereof, and
 (c) optionally metformin or/and a pharmaceutically acceptable salt thereof,
wherein the type 2 diabetes mellitus to be treated preferably is not adequately controlled with compound (b) and optionally compound (c) alone. In this aspect, the patient may be a patient as defined herein.

Yet another aspect of the present invention is method for the prevention of weight gain or/and for inducing weight loss in a type 2 diabetes mellitus patient, said method comprising administration the use of a combination comprising
 (a) lixisenatide or/and a pharmaceutically acceptable salt thereof,
 (b) insulin glargine or/and a pharmaceutically acceptable salt thereof, and
 (c) optionally metformin or/and a pharmaceutically acceptable salt thereof,
wherein the type 2 diabetes mellitus to be treated preferably is not adequately controlled with compound (b) and optionally compound (c) alone. In this aspect, the patient may be a patient as defined herein.

Yet another aspect of the present invention is method for the reduction of the risk of hypoglycemia in a type 2 diabetes mellitus patient, said method comprising administration the use of a combination comprising
 (a) lixisenatide or/and a pharmaceutically acceptable salt thereof,
 (b) insulin glargine or/and a pharmaceutically acceptable salt thereof, and (c) optionally metformin or/and a pharmaceutically acceptable salt thereof, wherein the type 2 diabetes mellitus to be treated preferably is not adequately controlled with compound (b) and optionally compound (c) alone. In this aspect, the patient may be a patient as defined herein.

Subject-matter of the present application is described in the following items:

1. A pharmaceutical combination for use in glycemic control, for use in the reduction of the HbA1c value, the fasting plasma glucose or/and the 2 hour postprandial plasma glucose, for use in the prevention of weight gain or/and for inducing weight loss, for use in the reduction of the risk of hypoglycemia, in a type 2 diabetes mellitus patient, said combination comprising
   (i) lixisenatide or/and a pharmaceutically acceptable salt thereof,
   (ii) insulin glargine or/and a pharmaceutically acceptable salt thereof, and
   (iii) optionally metformin or/and a pharmaceutically acceptable salt thereof.
2. The pharmaceutical combination for use according to item 1, wherein the type 2 diabetes mellitus to be treated is not adequately controlled with compound (b) and optionally compound (c) alone.
3. The pharmaceutical combination for use according to item 1 or 2, wherein the patient to be treated is obese.
4. The pharmaceutical combination for use according to any of the preceding items, wherein the patient to be treated has a body mass index of at least 30 kg/m$^2$.
5. The pharmaceutical combination for use according to any of the preceding items, wherein the patient to be treated has an age of at least 65 years.
6. The pharmaceutical combination for use according to any of the preceding items, wherein prior to the onset of therapy with the combination according to item 1, the patient has a fasting plasma glucose of at least 9 mmol/L when treated with a basal insulin monotherapy or a basal insulin and one to three oral anti-diabetics alone selected from the group consisting of metformin, a sulfonylurea, a DPP-4 inhibitor or a glinide alone.
7. The pharmaceutical combination for use according to any of the preceding items, wherein prior to the onset of therapy with the combination according to item 1, the patient has a fasting plasma glucose concentration in the range of 5.6 to 6.9 mmol/L or a fasting plasma glucose concentration of at least 6.6 mmol/L when treated with compound (b) and optionally compound (c) alone.
8. The pharmaceutical combination for use according to any of the preceding items, wherein prior to the onset of therapy with the combination according to item 1, the patient has a HbA1c of at least 8.5% when treated with a basal insulin monotherapy or a basal insulin and one to three oral anti-diabetics alone selected from the group consisting of metformin, a sulfonylurea, a DPP-4 inhibitor or a glinide alone.
9. The pharmaceutical combination for use according to any of the preceding items, wherein prior to the onset of therapy with the combination according to item 1, the patient has a HbA1c of at least 7.5% when treated with compound (b) and optionally compound (c) alone.
10. The pharmaceutical combination for use according to any of the items 6 to 9, wherein the basal insulin is selected from insulin glargine, insulin detemir and isophane insulin (NPH insulin).
11. The pharmaceutical combination for use of any of the preceding items, wherein the patient does not receive concomitant treatment with at least one of a sulfonylurea, a DPP-4 inhibitor and a glinide.
12. The pharmaceutical combination for use of any of the preceding items, wherein in the patient to be treated, type 2 diabetes mellitus has been diagnosed for at least 1 year or at least 2 years prior to the onset of a therapy with compounds (a), (b) and optionally (c).
13. The pharmaceutical combination for use of any of the preceding items, wherein the administration of the combination comprises the steps:
    (i) administration of compounds (b) and (c) for at least 4 weeks, and
    (ii) continuing treatment by administration of compounds (a), (b) and (c),
    wherein the amount of compound (b) to be administered in step (i) is adjusted so that a predetermined fasting plasma glucose level or/and a predetermined self-monitored plasma glucose level is reached or at least approximated.
14. The pharmaceutical combination for use according to item 13, wherein the amount of compound (b) to be administered in step (i) is adjusted so that
    (I) a fasting plasma glucose level or/and a fasting self-monitored plasma glucose level of about 4.4 mmol/l to about 5.6 mmol/l, or/and
    (II) a self-monitored plasma glucose level (SMPG) of about 7.8 mmol/l (or about 140 mg/dl) or less
    is reached or at least approximated.
15. The pharmaceutical combination for use according to item 14, wherein the self-monitored plasma glucose level in (II) is a 4-point self-monitored plasma glucose level or a 7-point self-monitored plasma glucose level.
16. The pharmaceutical combination for use of any of the preceding items, wherein lixisenatide or/and the pharmaceutically acceptable salt thereof is prepared for parenteral administration.
17. The pharmaceutical combination for use according to any of the preceding items, wherein lixisenatide or/and the pharmaceutically acceptable salt thereof is prepared for administration in a daily dose selected from the range of 10 µg to 20 µg.
18. The pharmaceutical combination for use according to any of the preceding items, wherein insulin glargine or/and or/and the pharmaceutically acceptable salt thereof is prepared for parenteral administration.
19. The pharmaceutical combination for use of any of the preceding items, wherein the metformin or/and the pharmaceutically acceptable salt thereof is prepared for oral administration.
20. A method for improving glycemic control, for the reduction of the HbA1c value or/and the fasting plasma glucose, for use in the prevention of weight gain or/and for inducing weight loss, for use in the reduction of the risk of hypoglycemia, said method comprising administering the combination of any one of the items 1 to 18 to a subject in need thereof.
21. The method of item 20, wherein the type 2 diabetes mellitus to be treated is not adequately controlled with compound (b) and optionally compound (c) alone.
22. The method of item 20 or 21, wherein the subject is the subject defined in any one of the items 2 to 15.

The invention is further illustrated by the following examples and figures.

FIGURE LEGENDS

FIG. 1—Plot of mean change in HbA1c (%) from baseline by visit—mITT population FIG. 2—Plot of mean change in body weight (kg) from baseline by visit—mITT population FIG. 3—Plot of mean insulin glargine daily dose (U) by visit—mITT population FIG. 4—Plot of mean daily insulin glulisine dose (U) by visit—mITT population FIG. 5—Plot of mean total insulin dose (U) by visit—mITT population FIG. 6—Graphical study design. [1] Insulin glargine should be injected subcutaneously once daily at dinner or breakfast time (according to patient's/investigators' preference). Injection time (dinner or breakfast) should be fixed at V2 and remain the same throughout the study. [2] Injection of lixisenatide should be performed 30-60 minutes prior to dinner or breakfast (the one associated with the highest self-monitored 2 h-PPG median value across 3 different days). Meal used for lixisenatide dosing should remain the same throughout the 26-week treatment period. [3] Injection of insulin glulisine should be done 0 to 15 minutes before dinner or breakfast (the one associated with the highest self-monitored 2 h-PPG median value across 3 different days). Meal used for insulin glulisine dosing should remain the same throughout the 26-week treatment period. [4] Injection of insulin glulisine prior to breakfast, lunch and dinner.

EXAMPLE 1

A Randomized, Open-Label, Active-Controlled, 3-Arm Parallel-Group, 26-Week Study Comparing the Efficacy and Safety of Lixisenatide to that of Insulin Glulisine Once Daily and Insulin Glulisine Three Times Daily in Patients with Type 2 Diabetes Insufficiently Controlled with Insulin Glargine with or without Metformin 1 Abbreviations AE: Adverse event
ANCOVA: Analysis of covariance
BMI: Body mass index
CI: Confidence interval
CMH: Cochran-Mantel-Haenszel
ECG: Electrocardiogram
FPG: Fasting plasma glucose
GLP-1: Glucagon-like peptide-1
IMP: Investigational medicinal product
LOCF: Last observation carried forward
LS: Least square
mITT: Modified Intent-To-Treat
PG: Plasma glucose
PT: Preferred term
QD: Quaque die (Once a day)
SAE: Serious adverse event
SMPG: Self-measured plasma glucose
SOC: System organ class
TEAE: Treatment-emergent adverse event
TID: Ter in die (Three times a day)

2  SYNOPSIS

| | |
|---|---|
| Title of the study: A randomized, open-label, active-controlled, 3-arm parallel-group, 26-week study comparing the efficacy and safety of lixisenatide to that of insulin glulisine once daily and insulin glulisine three times daily in patients with Type 2 diabetes insufficiently controlled with insulin glargine with or without metformin. | |

| | |
|---|---|
| Study center(s): Multicenter (199 centers in 18 countries) | |
| Publications (reference): NA | |
| Graphical study design: Figure 6 | |
| Phase of development: Phase 3 | |
| Objectives: Primary Objective To demonstrate in type 2 diabetic patients not adequately controlled on insulin glargine ± metformin:<br>• Versus insulin glulisine once daily (QD) non inferiority of lixisenatide in terms of HbA1c reduction at week 26.<br>• Versus insulin glulisine three times daily (TID) non inferiority of lixisenatide in terms of HbA1c reduction <u>or</u> superiority of lixisenatide on body weight change at week 26. | |
| Methodology: open-label, 1:1:1 randomized, active-controlled 3-arm (insulin glargine ± metformin + lixisenatide or insulin glulisine QD or insulin glulisine TID) parallel-group study stratified by V7 (week -1) strata of HbA1c (<8%, ≥8 %) and metformin use (yes, no). | |

| Number of patients: | Planned: 855 |
|---|---|
| | Randomized: 894 |
| | Treated: 893 |
| Evaluated: | Efficacy: 890 |
| | Safety: 893 |

| |
|---|
| • Diagnosis and criteria for inclusion: Inclusion criteria: Adult patients with type 2 diabetes mellitus diagnosed for at least 1 year, treated with basal insulin for at least 6 months prior to screening visit, and with a stable basal insulin regimen for at least 3 months prior to screening. Patients could be treated with basal insulin alone or in combination with 1 to 3 oral anti-diabetic drugs (OADs) that could be: metformin (≥1.5g/day or maximal tolerated dose), a sulfonylurea (SU), a dipeptidyl-peptidase-4 (DPP-4) inhibitor, a glinide. Key exclusion criteria at screening: HbA1c <7.5% or >10.0% for patients treated with basal insulin alone or in combination with metformin only; HbA1c <7.0% and >10.0% for patients treated with basal insulin and a combination of OADs which included a SU and/or a DPP-4 inhibitor and/or a glinide. Key exclusion criteria for randomization: HbA1c<7.0% or >9.0%; Mean fasting SMPG>140mg/dL (7.8mmol/L). |
| Study treatments Investigational medicinal products (IMPs): Lixisenatide and insulin glulisine <u>Formulation:</u> Lixisenatide was supplied as a sterile aqueous solution for subcutaneous (s.c.) injection in a 3-mL glass cartridge containing 300 μg of the active ingredient (ie, 100 μg/mL), Glycerol, Sodium acetate trihydrate, Methionine, Metacresol, HCL/NaOH, water for injection.<br>Insulin glulisine was supplied as Apidra® SoloSTAR®<br><u>Route of administration:</u> Lixisenatide was injected subcutaneously using Delta 14 self-injector device<br>Insulin glulisine was injected subcutaneously using the disposable SoloSTAR® self-injector device. |

Dose regimen:

Lixisenatide

Lixisenatide was started with QD injections of 10 µg for 2 weeks then continued at the maintenance dose of 20 µg QD up to the end of the treatment period. If the target maintenance dose of 20 µg was not tolerated, lixisenatide dose could be reduced to 10 µg. Lixisenatide was administered before breakfast or before dinner and remained the same regimen throughout the 26-week treatment period.

Insulin glulisine once daily (Basal Plus regimen)

The starting dose was 3 to 5 U. The dose of insulin glulisine was then titrated to obtain a bedtime (if injected at dinner) or pre-lunch (if injected at breakfast) SMPG value >100 mg/dL (5.6 mmol/L) and ≤140 mg/dL (7.8 mmol/L) while avoiding hypoglycemia. Insulin glulisine QD was administered before breakfast or before dinner and remained the same regimen throughout the 26-week treatment period.

Insulin glulisine three times daily (Basal Bolus regimen)

The starting dose for each meal was 3 to 5 U. The dose of insulin glulisine was then titrated to obtain before the next meal (pre-lunch or pre-dinner) or at bedtime (for the injection performed before dinner) a SMPG value >100 mg/dL (5.6 mmol/L) and ≤140 mg/dL (7.8 mmol/L) while avoiding hypoglycemia.

Stopping Rule:

In case HbA1c was above 8.5% at week 12 or later on, and appropriate corrective action (including appropriate titration of insulin glargine and/or insulin glulisine) failed and if the repeated HbA1c 4 weeks later remained above 8.5%, the assessment planned at visit 19 (final assessment on-treatment visit) and post-treatment follow-up visit was to be performed and the patient was to be discontinued from IMP and from the study.

Noninvestigational medicinal product(s) (background therapy):

Insulin glargine (Lantus®)

- Insulin glargine was supplied as Lantus® SoloSTAR® and was started at V2 (for those patients not already receiving insulin glargine) and injected subcutaneously using the disposable SoloSTAR® self-injector device.
- Metformin If patients were on metformin, it was to be at a stable dose of at least 1.5 g/day or maximal tolerated dose for at least 3 months prior to screening. This was continued at stable dose throughout the study.

Sulfonylureas, DPP-4 inhibitors and glinides were stopped at the start of run-in (Visit 2).

Insulin glargine was injected subcutaneously once daily at breakfast or dinner time according to patients'/ Investigators' preference. The injection time was to remain the same throughout the study.

Insulin glargine dose was titrated to achieve glycemic targets [fasting SMPG in the range of 80 to 100 mg/dL (4.4 to 5.6 mmol/L) without recurrent or severe hypoglycemia, except during the 4 weeks following randomization when a stable dose should be maintained. Doses could be reduced or modified at any time for recurrent or severe hypoglycemia.

If HbA1c at visit V7 (week -1) was ≥7% but ≤8.0%, the insulin glargine dose was to be reduced in order to avoid hypoglycemia when starting the IMP (lixisenatide or insulin glulisine).

Duration of treatment: 26 weeks

Duration of observation: Maximum duration was approximately 40 weeks.

Criteria for evaluation:

Primary efficacy endpoints:

The primary efficacy analysis was based on two co-primary endpoints:

- Change in HbA1c from baseline to week 26 (lixisenatide versus each insulin glulisine regimen).
- Change in body weight from baseline to week 26 (lixisenatide versus insulin glulisine TID).

Secondary efficacy endpoints included:

- Change in body weight from baseline to week 26 (lixisenatide versus insulin glulisine QD).
- Change in Fasting Plasma Glucose (FPG) from baseline to week 26
- Change in Insulin glargine dose from baseline to week 26.
- Insulin glulisine dose and total insulin dose at week 26.

Safety endpoints:

- Adverse events, serious adverse events, vital signs.
- Documented (PG <60 mg/dl) symptomatic hypoglycemia, severe hypoglycemia (percentage of subjects with at least one episode, number of events per patient-year).

Statistical methods:

Primary Analysis:

The primary analysis was based on a co-primary endpoint:
1  Non-inferiority of lixisenatide versus insulin glulisine QD on HbA1c change from baseline to Week 26,
2a  Non-inferiority of lixisenatide versus insulin glulisine TID on HbA1c change from baseline to Week 26,
2b  Superiority of lixisenatide versus Insulin glulisine TID on body weight change from baseline to Week 26.

Study was declared positive if both 1 and 2 (at least one of 2a or 2b) were met.

Overall, the statistical assessment was performed at α=0.025 (1-sided) for the co-primary endpoint. Both 1 and 2 (either 2a or 2b) were assessed at α=0.025 (1-sided), and both 1 and 2a were assessed at a non-inferiority margin for HbA1c of 0.4%.

For the co-primary endpoint 1, the non-inferiority was assessed using the upper bound of the 2-sided 95% CI. If the upper bound of the 95% CI was less than 0.4%, the non-inferiority of lixisenatide versus insulin glulisine QD was achieved.

For the co-primary endpoint 2 (2a and 2b), Hochberg procedure was used for these 2 comparisons at α=0.025 (1-sided) in order to control the type 1 error: If non-inferiority of lixisenatide versus insulin glulisine TID on HbA1c and superiority of lixisenatide versus insulin glulisine TID on body weight were both met at α=0.025 (1-sided), then endpoint 2 was met at α=0.025 (1-sided). If only one of them was met, then the one met should be tested at α=0.0125 (1-sided). The non-inferiority on HbA1c was assessed using the upper bound of the 2-sided 95% CI (or 97.5% CI). If the upper bound of the 95% CI (or 97.5% CI) on HbA1c was less than 0.4%, the non-inferiority of lixisenatide versus insulin glulisine TID on HbA1c was met at 1-sided α=0.025 (or α=0.0125). The superiority on body weight was assessed by comparing the p-value with the 1-sided α=0.025 (or α=0.0125).

The primary endpoints were analyzed using an analysis of covariance (ANCOVA) model with treatment (lixisenatide, insulin glulisine QD and insulin glulisine TID), V7 (week -1) strata of HbA1c (<8%, ≥8 %), randomization strata of metformin use (yes, no) and country as fixed effects and using the corresponding baseline value as a covariate. Difference between lixisenatide and insulin glulisine QD and the associated two sided 95% confidence interval were estimated. Similarly, difference between lixisenatide and insulin glulisine TID and the associated 2-sided 95% confidence interval (or 97.5% confidence interval if either 2a or 2b was not met) were estimated for HbA1c and body weight.

Analysis of secondary endpoints:

All continuous secondary efficacy endpoints (except for insulin glulisine and total daily insulin doses) were analyzed using the same ANCOVA model as described for the primary endpoint. Differences between treatment groups and confidence intervals were estimated. Insulin glulisine and total daily insulin doses were summarized by treatment group.

All categorical efficacy parameters were analyzed using the Cochran-Mantel-Haenszel (CMH) method stratified by V7 (week -1) strata of HbA1c (<8%, ≥8 %), and randomization strata of metformin use (Y, N). Missing efficacy endpoint values including that of primary endpoints were imputed using LOCF method.

Safety analyses:

Safety analyses for the 26-week open-label treatment period were descriptive, based on the safety population.

Summary:

Population characteristics: A total of 894 patients were randomized to one of the three treatment groups (298 patients each): lixisenatide, insulin glulisine QD and insulin glulisine TID. One patient randomized to insulin glulisine TID group was not exposed to the IMP, and 890 patients were included in the mITT population. Four patients randomized to the insulin glulisine TID arm were included in the insulin glulisine QD arm of the safety population since they injected insulin glulisine once a day more than 50% of the time. One patient randomized to the insulin glulisine QD arm was included in the insulin glulisine TID arm of safety population since he injected insulin glulisine three times a day more than 50% of the time. (Table 1). Demographics and baseline characteristics were generally similar across the treatment groups. The median age was 60 years. The study population was primarily Caucasian (92.6%), and 54.7% of the population were female patients (Table 2).

Efficacy results:

Primary analysis

Change in HbA1c from baseline to Week 26: lixisenatide versus insulin glulisine QD Mean changes in HbA1c were -0.63% for the lixisenatide group and -0.58% for the insulin glulisine QD group (Difference = -0.05%, 95% CI: -0.170% to 0.064%). The non-inferiority of lixisenatide compared to insulin glulisine QD was demonstrated, as the upper bound of the two-sided 95% CI of the treatment difference was less than the predefined non-inferiority margin of 0.4% (Table 6).

Change in HbA1c from baseline to Week 26: lixisenatide versus insulin glulisine TID Mean changes in HbA1c were -0.63% for the lixisenatide group and -0.84% for the insulin glulisine TID group (Difference = 0.21%, 95% CI: 0.095% to 0.328%). The non-inferiority of lixisenatide compared to the insulin glulisine TID was demonstrated, as the upper bound of the two-sided 95% CI of the treatment difference was less than the predefined non-inferiority margin of 0.4% (Table 6).

Change in body weight from baseline to Week 26: lixisenatide versus insulin glulisine TID Mean changes body weight were -0.63 kg for the lixisenatide group and 1.37 kg for the insulin glulisine TID group (Difference = -1.99 kg, p-value<0.0001). The superiority of lixisenatide compared to insulin glulisine TID in body weight was demonstrated at $\alpha=0.025$ one-sided (Table 7).

Secondary efficacy endpoints:

Mean changes from baseline to Week 26 in body weight were -0.63 kg for the lixisenatide group and 1.03 kg for the insulin glulisine QD group (Difference = -1.66 kg, 95% CI: -2.257 to -1.062 kg) (Table 7).

Mean changes in FPG were -0.23 mmol/L in the lixisenatide group, -0.21 mmol/L in the glulisine QD group and -0.06 mmol/L in the glulisine TID group (Differences: lixisenatide versus glulisine QD = -0.01 mmol/L, 95% CI: [-0.319 to 0.298]; lixisenatide versus glulisine TID = -0.17 mmol/L, 95% CI: [-0.475 to 0.143]) (Table 8).

Changes in insulin glargine dose were 0.70 U in the lixisenatide group, -0.06 U in the glulisine QD group and -3.13 U in the glulisine TID group (Table 9).

Mean daily insulin glulisine dose at Week 26 was 9.97 U in the insulin glulisine QD group and 20.24 U in the insulin glulisine TID group (Figure 4). Mean total daily insulin dose at Week 26 was 73.61 U in the insulin glulisine QD group and 81.05 U in the insulin glulisine TID group (Figure 5).

Safety results:

The percentages of patients with any TEAEs were: lixisenatide 74.2%, insulin glulisine QD 73.8% and insulin glulisine TID 80.3%. The two most frequent TEAEs were "hypoglycemia" which were reported in 107 patients (35.9%) in the lixisenatide group, 140 patients (46.5%) in the insulin glulisine QD group, and 154 patients (52.4%) in the insulin glulisine TID group, and "blood glucose decreased" (events not accompanied by typical symptoms of hypoglycemia) which were reported in 60 patients (20.1%) in the lixisenatide group, 67 patients (22.3%) in the insulin glulisine QD group, and 82 patients (27.9%) in the insulin glulisine TID group. Nausea was reported in 75 patients (25.2%) in lixisenatide group, 5 patients (1.7%) in the insulin glulisine QD group and 3 patients (1.0%) in the insulin glulisine TID group (Table 11).

Serious TEAEs were reported by a similar number of patients in all treatment groups (lixisenatide: 11/298 [3.7%], glulisine QD: 11/301 [3.7%] and glulisine TID: 14/294 [4.8%]) (Table 12). Three patients died during the study due to a TEAE, one from the lixisenatide group and two from the insulin glulisine TID group:

- lixisenatide group: metastatic pancreatic cancer. A 67 year-old male patient was diagnosed with metastatic pancreatic cancer 35 days after the first administration of the IMP. The patient permanently discontinued lixisenatide. Further evaluation showed a tumor classified T4N+M1 of the corpus part of the pancreatic gland with infiltration into the vein of the left kidney and into the left adrenal gland with multiple metastases in the liver, intra-abdominal lymphadenopathy, peritoneal dissemination, and ascites. The patient underwent palliative care and died on study day 52. The event was adjudicated by PSAC as probable malignant pancreatic neoplasm unrelated to IMP.

- glulisine TID: skin ulcer haemorrhage. A 75 year-old male patient died of exsanguination due to severe bleeding from a skin ulcer 155 days after the first intake of insulin glulisine.

- glulisine TID: cardiac failure chronic. A 59 year-old male was found dead on study day 145. Autopsy was performed and the reason of death was reported as exacerbation of chronic heart insufficiency.

None of the deaths were considered related to IMP.

One additional patient died during the run-in period due to worsening of chronic obstructive pulmonary disease (pre-treatment AE).

More patients in the lixisenatide group experienced at least one TEAE leading to permanent treatment discontinuation compared to the insulin glulisine groups (lixisenatide: 15/298 [5.0%], glulisine QD: 2/301 [0.7%] and glulisine TID: 3/294 [1.0%]), mainly due to gastrointestinal disorders (3.7% in the lixisenatide group versus none in glulisine QD or TID group) including nausea and vomiting in four patients (1.3%) each. (Table 13).

Protocol defined TEAEs of symptomatic hypoglycemia (either accompanied by plasma glucose < 60 mg/dL [3.3 mmol/L] or associated with prompt recovery after countermeasures if no plasma glucose was available) were experienced by more patients in the insulin glulisine groups compared to the lixisenatide group (lixisenatide: 98/298 [32.9%]; glulisine QD: 117/301 [38.9%]; glulisine TID: 132/294 [44.9%]). Similarly, more TEAEs of symptomatic hypoglycemia per 100 patient years occurred in the insulin glulisine QD group and insulin glulisine TID group (266.4 and 410.4, respectively) than in the lixisenatide group (229.6) (Table 14). Two patients (both from the insulin glulisine QD group) experienced TEAEs defined as severe symptomatic hypoglycemia per protocol. Thirteen patients in the insulin glulisine QD group and 20 patients in the insulin glulisine TID group reported symptomatic or asymptomatic accidental overdose with IMP versus none in lixisenatide group.

Three lixisenatide-treated patients (1.0%) and 1 (0.3%) patient in the glulisine TID group had a TEAE adjudicated as allergic reaction by ARAC, however none were adjudicated as possibly related to IMP (Table 15).

One patient (0.3%) in the lixisenatide group had one TEAE adjudicated by PSAC as acute pancreatitis of mild intensity (Table 16):

- A 57-year old female patient had a TEAE of suspected pancreatitis of moderate intensity 89 days after first lixisenatide administration. Four days before the onset of the event routine laboratory results revealed lipase 3.37 x ULN. The investigator reported that the event consisted of epigastric pain of mild intensity, nausea and diarrhea. Abdominal US performed on Day 90 revealed steatohepatitis, which was reported as a new TEAE; no signs consistent with pancreatitis were observed. Lipase retested on Day 90 was within the normal range. The IMP was temporarily discontinued from Day 91 and was resumed on Day 102. The subject was considered recovered from the event on Day 92 without sequelae and completed the study treatment with lixisenatide as per protocol. Further scheduled central laboratory test showed pancreatic enzymes within normal ranges. The investigator considered the event as related to lixisenatide.

Two patients in the lixisenatide group and one patient in the insulin glulisine TID group had a TEAE of increased calcitonin (≥20 pg/mL) that were reported on the specific AE form (Table 17).

Preliminary Conclusions:

This study in 894 patients with T2DM not adequately controlled on insulin glargine ± metformin met its primary objective, demonstrating non-inferiority of lixisenatide versus insulin glulisine QD as well as insulin glulisine TID in reducing HbA1c levels, and demonstrating superiority of lixisenatide versus insulin glulisine TID in body weight change.

The study medication was well tolerated by patients in all three treatment groups, more patients in the insulin glulisine groups reported protocol defined events of symptomatic hypoglycemia. More patients in the lixisenatide group discontinued the study prematurely mostly due to gastrointestinal TEAEs. In the lixisenatide group, 1 event was adjudicated by PSAC as probable malignant pancreatic neoplasm unrelated to IMP, and 1 event was adjudicated by PSAC as acute pancreatitis of mild intensity.

3 Results
3.1 Study Patients
3.1.1 Patient Accountability

TABLE 1

| Analysis populations | | | | |
|---|---|---|---|---|
| | Lixisenatide | Insulin Glulisine QD | Insulin Glulisine TID | All |
| Randomized population Efficacy population | 298 (100%) | 298 (100%) | 298 (100%) | 894 (100%) |
| Modified Intent-to-Treat (mITT) | 297 (99.7%) | 298 (100%) | 295 (99.0%) | 890 (99.6%) |
| Safety population | 298 | 301 | 294 | 893 |

Note:
The safety population patients are tabulated according to treatment actually received (as treated). For the other populations, patients are tabulated according to their randomized treatment.

3.1.2 Study Disposition

TABLE 2

| Patient disposition - Randomized population | | | |
|---|---|---|---|
| | Lixisenatide (N = 298) | Insulin Glulisine QD (N = 298) | Insulin Glulisine TID (N = 298) |
| Randomized and not treated | 0 | 0 | 1 (0.3%) |
| Randomized and treated | 298 (100%) | 298 (100%) | 297 (99.7%) |
| Completed study treatment period | 268 (89.9%) | 281 (94.3%) | 285 (95.6%) |
| Did not complete study treatment period | 30 (10.1%) | 17 (5.7%) | 12 (4.0%) |
| Subject's decision for treatment discontinuation | 18 (6.0%) | 11 (3.7%) | 8 (2.7%) |
| Reason for treatment discontinuation | | | |
| Adverse event | 14 (4.7%) | 2 (0.7%) | 5 (1.7%) |
| Lack of efficacy[a] | 6 (2.0%) | 4 (1.3%) | 0 |
| Poor compliance to protocol | 0 | 3 (1.0%) | 2 (0.7%) |
| Lost to follow-up | 0 | 0 | 0 |
| Other reasons | 9 (3.0%) | 8 (2.7%) | 5 (1.7%) |

[a] No rescue therapy was planned for the study, instead discontinuation was recommended if HbA1c value is above 8.5% at Week 12 or later on, and if appropriate corrective action fails and the repeated HbA1c 4 weeks later remains above 8.5%.

Note:
Percentages are calculated using the number of patients randomized as denominator.

3.1.3 Demographics and Baseline Characteristics

TABLE 3

| Demographics and patient characteristics at screening or baseline - Randomized population | | | | |
|---|---|---|---|---|
| | Lixisenatide (N = 298) | Insulin Glulisine QD (N = 298) | Insulin Glulisine TID (N = 298) | All (N = 894) |
| Age (years) | | | | |
| Number | 298 | 298 | 298 | 894 |
| Mean (SD) | 59.8 (8.6) | 60.2 (8.6) | 59.4 (9.5) | 59.8 (8.9) |
| Median | 60.0 | 60.0 | 60.0 | 60.0 |
| Min:Max | 35:79 | 35:78 | 32:87 | 32:87 |
| Age group (years) [n (%)] | | | | |
| Number | 298 | 298 | 298 | 894 |
| <50 | 39 (13.1%) | 33 (11.1%) | 48 (16.1%) | 120 (13.4%) |
| ≥50 to <65 | 170 (57.0%) | 172 (57.7%) | 154 (51.7%) | 496 (55.5%) |
| ≥65 to <75 | 76 (25.5%) | 76 (25.5%) | 85 (28.5%) | 237 (26.5%) |
| ≥75 | 13 (4.4%) | 17 (5.7%) | 11 (3.7%) | 41 (4.6%) |
| Gender [n (%)] | | | | |
| Number | 298 | 298 | 298 | 894 |
| Male | 138 (46.3%) | 135 (45.3%) | 132 (44.3%) | 405 (45.3%) |
| Female | 160 (53.7%) | 163 (54.7%) | 166 (55.7%) | 489 (54.7%) |
| Race [n (%)] | | | | |
| Number | 298 | 298 | 298 | 894 |
| Caucasian/White | 276 (92.6%) | 280 (94.0%) | 272 (91.3%) | 828 (92.6%) |
| Black | 13 (4.4%) | 11 (3.7%) | 12 (4.0%) | 36 (4.0%) |
| Asian/Oriental | 9 (3.0%) | 7 (2.3%) | 13 (4.4%) | 29 (3.2%) |
| Other | 0 | 0 | 1 (0.3%) | 1 (0.1%) |

TABLE 3-continued

Demographics and patient characteristics at screening or baseline - Randomized population

|  | Lixisenatide (N = 298) | Insulin Glulisine QD (N = 298) | Insulin Glulisine TID (N = 298) | All (N = 894) |
|---|---|---|---|---|
| V1 (Week −14) HbA1c (%) | | | | |
| Number | 297 | 298 | 298 | 893 |
| Mean (SD) | 8.51 (0.72) | 8.49 (0.72) | 8.51 (0.78) | 8.50 (0.74) |
| Median | 8.50 | 8.40 | 8.50 | 8.50 |
| Min:Max | 7.1:10.0 | 7.0:10.0 | 7.0:10.0 | 7.0:10.0 |
| V7 (Week −1) HbA1c (%) | | | | |
| Number | 298 | 297 | 298 | 893 |
| Mean (SD) | 7.87 (0.53) | 7.82 (0.52) | 7.89 (0.54) | 7.86 (0.53) |
| Median | 7.80 | 7.80 | 7.90 | 7.80 |
| Min:Max | 7.0:9.0 | 7.0:8.9 | 7.0:9.0 | 7.0:9.0 |
| Randomization strata of HbA1c category (%) [n (%)] | | | | |
| Number | 298 | 298 | 298 | 894 |
| <8% | 172 (57.7%) | 171 (57.4%) | 172 (57.7%) | 515 (57.6%) |
| ≥8% | 126 (42.3%) | 127 (42.6%) | 126 (42.3%) | 379 (42.4%) |
| Randomization strata of metformin use (%) [n (%)] | | | | |
| Number | 298 | 298 | 298 | 894 |
| Yes | 257 (86.2%) | 258 (86.6%) | 257 (86.2%) | 772 (86.4%) |
| No | 41 (13.8%) | 40 (13.4%) | 41 (13.8%) | 122 (13.6%) |
| V2 (Week −12) FPG (mmol/L) | | | | |
| Number | 296 | 293 | 297 | 886 |
| Mean (SD) | 9.16 (2.94) | 9.28 (2.88) | 9.51 (2.96) | 9.32 (2.93) |
| Median | 9.05 | 9.10 | 9.30 | 9.10 |
| Min:Max | 3.6:20.5 | 2.9:20.2 | 3.4:22.6 | 2.9:22.6 |
| V7 (Week −1) FPG (mmol/L) | | | | |
| Number | 289 | 291 | 289 | 869 |
| Mean (SD) | 6.91 (2.07) | 6.75 (1.80) | 6.65 (1.86) | 6.77 (1.91) |
| Median | 6.60 | 6.50 | 6.40 | 6.50 |
| Min:Max | 2.8:13.6 | 2.9:13.6 | 3.0:14.1 | 2.8:14.1 |
| V2 (Week −12) Body Weight (kg) | | | | |
| Number | 298 | 298 | 298 | 894 |
| Mean (SD) | 89.75 (17.37) | 87.93 (15.84) | 89.66 (17.28) | 89.11 (16.85) |
| Median | 88.20 | 87.55 | 87.75 | 88.00 |
| Min:Max | 54.1:155.8 | 51.0:132.8 | 46.4:152.0 | 46.4:155.8 |
| Meal for IMP injection[a] | | | | |
| Number | 298 | 298 | | |
| Breakfast | 90 (30.2%) | 88 (29.5%) | | |
| Dinner | 207 (69.5%) | 208 (69.8%) | | |
| Missing | 1 (0.3%) | 2 (0.7%) | | |

BMI = Body Mass Index.
[a]Meal for IMP injection as determined by 4-point SMPG, only presented for lixisenatide and insulin glulisine QD groups.

TABLE 4

Disease characteristics at screening or baseline - Randomized population

|  | Lixisenatide (N = 298) | Insulin Glulisine QD (N = 298) | Insulin Glulisine TID (N = 298) | All (N = 894) |
|---|---|---|---|---|
| Duration of diabetes (years) | | | | |
| Number | 298 | 298 | 298 | 894 |
| Mean (SD) | 11.89 (6.43) | 12.33 (6.75) | 12.41 (6.80) | 12.21 (6.66) |
| Median | 11.03 | 11.44 | 11.45 | 11.34 |
| Min:Max | 1.3:37.9 | 1.1:50.2 | 1.0:37.1 | 1.0:50.2 |
| Duration of treatment with basal insulin treatment (years) | | | | |
| Number | 298 | 298 | 298 | 894 |
| Mean (SD) | 3.07 (2.64) | 3.26 (3.46) | 3.19 (3.13) | 3.17 (3.09) |

TABLE 4-continued

Disease characteristics at screening or baseline - Randomized population

|  | Lixisenatide (N = 298) | Insulin Glulisine QD (N = 298) | Insulin Glulisine TID (N = 298) | All (N = 894) |
|---|---|---|---|---|
| Median | 2.32 | 2.28 | 2.01 | 2.15 |
| Min:Max | 0.1:16.9 | 0.2:35.8 | 0.3:20.1 | 0.1:35.8 |
| Daily dose of basal insulin by types at screening (U) | | | | |
| Glargine | | | | |
| Number | 199 | 203 | 191 | 593 |
| Mean (SD) | 41.70 (23.23) | 41.36 (23.35) | 40.23 (22.73) | 41.11 (23.08) |
| Median | 35.00 | 34.00 | 33.00 | 34.00 |
| Min:Max | 12.0:140.0 | 16.0:160.0 | 12.0:160.0 | 12.0:160.0 |
| Detemir | | | | |
| Number | 25 | 32 | 30 | 87 |
| Mean (SD) | 41.00 (29.69) | 39.59 (25.27) | 39.43 (21.59) | 39.94 (25.18) |
| Median | 32.00 | 30.00 | 35.00 | 32.00 |
| Min:Max | 20.0:160.0 | 18.0:120.0 | 20.0:125.0 | 18.0:160.0 |
| NPH | | | | |
| Number | 74 | 63 | 77 | 214 |
| Mean (SD) | 40.61 (20.43) | 38.97 (18.20) | 40.92 (20.26) | 40.24 (19.66) |
| Median | 33.00 | 36.00 | 36.00 | 34.50 |
| Min:Max | 20.0:116.0 | 16.0:100.0 | 16.0:116.0 | 16.0:116.0 |
| Daily dose of insulin glargine at V2 (Week −12) (U) | | | | |
| Number | 298 | 298 | 298 | 894 |
| Mean (SD) | 40.92 (21.78) | 39.83 (22.04) | 39.46 (21.00) | 40.07 (21.60) |
| Median | 34.00 | 34.00 | 34.50 | 34.00 |
| Min:Max | 16.0:134.0 | 16.0:160.0 | 12.0:160.0 | 12.0:160.0 |
| Daily dose of insulin glargine at V8 (Week 0) (U) | | | | |
| Number | 292 | 295 | 296 | 883 |
| Mean (SD) | 67.88 (31.90) | 64.72 (32.12) | 65.14 (26.90) | 65.91 (30.39) |
| Median | 62.00 | 58.00 | 60.83 | 60.00 |
| Min:Max | 13.0:192.0 | 14.0:205.3 | 18.0:204.0 | 13.0:205.3 |
| Metformin use at screening [n (%)] | | | | |
| Number | 298 | 298 | 298 | 894 |
| Yes | 262 (87.9%) | 260 (87.2%) | 259 (86.9%) | 781 (87.4%) |
| No | 36 (12.1%) | 38 (12.8%) | 39 (13.1%) | 113 (12.6%) |
| Daily dose of metformin at baseline (mg) | | | | |
| Number | 262 | 260 | 258 | 780 |
| Mean (SD) | 2069.37 (486.66) | 2089.13 (477.03) | 2114.15 (446.74) | 2090.77 (470.31) |
| Median | 2000.00 | 2000.00 | 2000.00 | 2000.00 |
| Min:Max | 500.0:3000.0 | 750.0:3400.0 | 850.0:3000.0 | 500.0:3400.0 |

GLP-1 = Glucagon like peptide-1.

3.1.4 Dosage and Treatment Compliance

TABLE 5

Treatment compliance - Safety population

|  | Lixisenatide (N = 298) | Insulin Glulisine QD (N = 301) | Insulin Glulisine TID (N = 294) |
|---|---|---|---|
| Compliance rate (%) | | | |
| Number | 297 | 301 | 294 |
| Mean (SD) | 99.34 (2.69) | 98.72 (6.00) | 97.12 (15.97) |
| Median | 100.00 | 100.00 | 100.00 |
| Min:Max | 68.2:102.7 | 44.4:113.3 | 0.0:298.4 |
| Overall compliance [n (%)] | | | |
| Number | 297 | 301 | 294 |
| Patients with <60% | 0 | 3 (1.0%) | 4 (1.4%) |
| Patients with ≥60% to <80% | 2 (0.7%) | 1 (0.3%) | 12 (4.1%) |

TABLE 5-continued

Treatment compliance - Safety population

| | Lixisenatide (N = 298) | Insulin Glulisine QD (N = 301) | Insulin Glulisine TID (N = 294) |
|---|---|---|---|
| Patients with ≥80% to ≤100% | 294 (99.0%) | 296 (98.3%) | 273 (92.9%) |
| Patients with >100% | 1 (0.3%) | 1 (0.3%) | 5 (1.7%) |
| Missing | 1 | 0 | 0 |

IMP: Investigational Medicinal Product
Note:
Compliance rate (%) = (Total number of actual IMP injections for the dosing interval/Total number of expected IMP injections for the dosing interval) × 100.

3.2 Efficacy
3.2.1 Primary Efficacy Endpoint

TABLE 6

Mean change in HbA1c (%) from baseline to Week 26 - mITT population

| HbA1c (%) | Lixisenatide (N = 297) | Insulin Glulisine QD (N = 298) | Insulin Glulisine TID (N = 295) |
|---|---|---|---|
| Baseline | | | |
| Number | 292 | 292 | 295 |
| Mean (SD) | 7.76 (0.56) | 7.72 (0.58) | 7.79 (0.60) |
| Median | 7.70 | 7.70 | 7.70 |
| Min:Max | 6.4:9.8 | 6.5:9.5 | 6.5:12.1 |
| Week 26 (LOCF) | | | |
| Number | 292 | 292 | 295 |
| Mean (SD) | 7.17 (0.77) | 7.21 (0.79) | 6.96 (0.73) |
| Median | 7.10 | 7.10 | 7.00 |
| Min:Max | 5.1:9.8 | 5.2:10.5 | 5.1:9.1 |
| Change from baseline to Week 26 (LOCF) | | | |
| Number | 292 | 292 | 295 |
| Mean (SD) | −0.59 (0.79) | −0.51 (0.80) | −0.82 (0.78) |
| Median | −0.60 | −0.50 | −0.90 |
| Min:Max | −3.4:2.0 | −2.6:2.5 | −5.6:1.7 |
| LS Mean (SE) [a] | −0.63 (0.054) | −0.58 (0.054) | −0.84 (0.053) |
| LS Mean difference (SE) of Lixisenatide vs. [a,b] | — | −0.05 (0.059) | 0.21 (0.059) |
| 95% CI | — | (−0.170 to 0.064) | (0.095 to 0.328) |

LOCF = Last observation carried forward.
[a] Analysis of covariance (ANCOVA) model with treatment groups (lixisenatide, insulin glulisine QD, and insulin glulisine TID), Visit 7 (Week −1) strata of HbA1c [<8.0, ≥8.0%], randomization strata of metformin use, and country as fixed effects and baseline HbA1c value as a covariate.
[b] Difference in LS Mean between lixisenatide vs. insulin glulisine QD, or lixisenatide vs. insulin glulisine TID.
The analysis included measurements obtained up to 14 days after the last injection of the investigational medicinal product.
Patients with both baseline and Week 26 (LOCF) measurements are included.

TABLE 7

Mean change in body weight (kg) from baseline to Week 26 - mITT population

| Body weight (kg) | Lixisenatide (N = 297) | Insulin Glulisine QD (N = 298) | Insulin Glulisine TID (N = 295) |
|---|---|---|---|
| Baseline | | | |
| Number | 295 | 295 | 295 |
| Mean (SD) | 90.10 (17.39) | 88.37 (15.88) | 90.00 (17.21) |
| Median | 88.00 | 88.00 | 88.70 |
| Min:Max | 54.2:158.4 | 53.6:132.8 | 49.0:154.2 |
| Week 26 (LOCF) | | | |
| Number | 295 | 295 | 295 |
| Mean (SD) | 89.37 (18.14) | 89.31 (16.27) | 91.29 (17.27) |
| Median | 87.30 | 88.40 | 90.50 |

TABLE 7-continued

Mean change in body weight (kg) from baseline to Week 26 - mITT population

| Body weight (kg) | Lixisenatide (N = 297) | Insulin Glulisine QD (N = 298) | Insulin Glulisine TID (N = 295) |
|---|---|---|---|
| Min:Max | 54.2:191.1 | 55.0:134.8 | 50.3:155.0 |
| Change from baseline to Week 26 (LOCF) | | | |
| Number | 295 | 295 | 295 |
| Mean (SD) | −0.72 (5.16) | 0.94 (2.50) | 1.29 (2.80) |
| Median | −0.50 | 0.90 | 1.20 |
| Min:Max | −16.4:72.5 | −8.2:10.9 | −9.5:12.4 |
| LS Mean (SE) [a] | −0.63 (0.276) | 1.03 (0.276) | 1.37 (0.271) |
| LS Mean difference (SE) of Lixisenatide vs. [ab] | — | −1.66 (0.305) | −1.99 (0.305) |
| 95% CI | — | (−2.257 to −1.062) | (−2.593 to −1.396) |
| p-value | | <.0001 | <.0001 |

LOCF = Last observation carried forward.
[a] Analysis of covariance (ANCOVA) model with treatment groups (lixisenatide, insulin glulisine QD, and insulin glulisine TID), Visit 7 (Week −1) strata of HbA1c [<8.0, ≥8.0%], randomization strata of metformin use, and country as fixed effects and baseline body weight as a covariate.
[b] Difference in LS Mean between lixisenatide vs. insulin glulisine QD, or lixisenatide vs. insulin glulisine TID.
The analysis included measurements obtained up to 3 days after the last injection of the investigational medicinal product.
Patients with both baseline and Week 26 (LOCF) measurements are included.

FIG. 1 shows the mean change in HbA1c (%) from baseline by visit in the mITT population. FIG. 2 shows the mean change in body weight (kg) from baseline by visit in the mITT population.

3.2.2 Other Key Efficacy Endpoints

TABLE 8

Mean change in fasting plasma glucose (mmol/L) from baseline to Week 26 - mITT population

| Fasting plasma glucose (mmol/L) | Lixisenatide (N = 297) | Insulin Glulisine QD (N = 298) | Insulin Glulisine TID (N = 295) |
|---|---|---|---|
| Baseline | | | |
| Number | 295 | 295 | 294 |
| Mean (SD) | 6.58 (1.83) | 6.85 (1.99) | 6.65 (1.89) |
| Median | 6.40 | 6.50 | 6.40 |
| Min:Max | 2.9:16.1 | 2.9:13.8 | 2.9:13.4 |
| Week 26 (LOCF) | | | |
| Number | 295 | 295 | 294 |
| Mean (SD) | 6.59 (1.96) | 6.66 (1.94) | 6.71 (2.02) |
| Median | 6.20 | 6.40 | 6.50 |
| Min:Max | 2.9:15.3 | 2.9:16.1 | 2.7:16.2 |
| Change from baseline to Week 26 (LOCF) | | | |
| Number | 295 | 295 | 294 |
| Mean (SD) | 0.01 (2.15) | −0.19 (2.52) | 0.05 (2.47) |
| Median | −0.15 | −0.10 | −0.20 |
| Min:Max | −7.0:7.9 | −8.4:7.5 | −7.5:10.7 |
| LS Mean (SE) [a] | −0.23 (0.143) | −0.21 (0.142) | −0.06 (0.140) |
| LS Mean difference (SE) of Lixisenatide vs. [ab] | — | −0.01 (0.157) | −0.17 (0.158) |
| 95% CI | — | (−0.319 to 0.298) | (−0.475 to 0.143) |

LOCF = Last observation carried forward.
[a] Analysis of covariance (ANCOVA) model with treatment groups (lixisenatide, insulin glulisine QD, insulin glulisine TID), Visit 7 (Week −1) strata of HbA1c [<8.0, ≥8.0%], randomization strata of metformin use, and country as fixed effects and baseline fasting plasma glucose as a covariate
[b] Difference in LS Mean between lixisenatide vs. insulin glulisine QD, or lixisenatide vs. insulin glulisine TID.
The analysis included measurements obtained up to one day after the last injection of the investigational medicinal product.
Patients with both baseline and Week 26 (LOCF) measurements are included.

TABLE 9

Mean change in insulin glargine dose (U) from baseline to Week 26 - mITT population

| Insulin glargine dose (Units) | Lixisenatide (N = 297) | Insulin Glulisine QD (N = 298) | Insulin Glulisine TID (N = 295) |
|---|---|---|---|
| Baseline | | | |
| Number | 292 | 294 | 294 |
| Mean (SD) | 67.45 (31.68) | 64.79 (32.09) | 65.05 (27.01) |
| Median | 62.00 | 58.00 | 60.67 |
| Min:Max | 13.0:192.0 | 14.0:205.3 | 18.0:204.0 |
| Week 26 (LOCF) | | | |
| Number | 292 | 294 | 294 |
| Mean (SD) | 67.22 (36.22) | 63.89 (35.67) | 61.16 (29.33) |
| Median | 60.00 | 54.00 | 57.00 |
| Min:Max | 14.0:224.7 | 9.3:254.0 | 14.0:230.0 |
| Change from baseline to Week 26 (LOCF) | | | |
| Number | 292 | 294 | 294 |
| Mean (SD) | −0.22 (13.59) | −0.91 (13.41) | −3.89 (13.28) |
| Median | −1.00 | −1.33 | −4.00 |
| Min:Max | −36.0:60.0 | −72.7:76.0 | −56.0:35.3 |
| LS Mean (SE) [a] | 0.70 (1.002) | −0.06 (0.999) | −3.13 (0.982) |
| LS Mean difference (SE) of Lixisenatide vs. [a,b] | — | 0.76 (1.104) | 3.83 (1.106) |
| 95% CI | — | (−1.410 to 2.923) | (1.658 to 6.001) |

LOCF = Last observation carried forward.
[a] Analysis of covariance (ANCOVA) model with treatment groups (lixisenatide, insulin glulisine QD, insulin glulisine TID), Visit 7 (Week −1) strata of HbA1c [<8.0, ≥8.0%], randomization strata of metformin use, and country as fixed effects and baseline insulin glargine dose as a covariate.
[b] Difference in LS Mean between lixisenatide vs. insulin glulisine QD, or lixisenatide vs. insulin glulisine TID.
The analysis included measurements obtained up to the date of the last injection of the investigational medicinal product.
Patients with both baseline and Week 26 (LOCF) measurements are included.

FIG. 3 shows the mean insulin glargine daily dose (U) by visit in the mITT population. FIG. 4 shows the mean daily insulin glulisine dose (U) by visit in the mITT population. FIG. 5 shows the mean total insulin dose (U) by visit in the mITT population 3.3 Safety
3.3.1 Treatment-Emergent Adverse Events

TABLE 10

Overview of adverse event profile: treatment emergent adverse events - Safety

| | Lixisenatide (N = 298) | Insulin Glulisine QD (N = 301) | Insulin Glulisine TID (N = 294) |
|---|---|---|---|
| Patients with any TEAE | 221 (74.2%) | 222 (73.8%) | 236 (80.3%) |
| Patients with any treatment emergent SAE | 11 (3.7%) | 11 (3.7%) | 14 (4.8%) |
| Patients with any TEAE leading to death | 1 (0.3%) | 0 | 2 (0.7%) |
| Patients with any TEAE leading to permanent treatment discontinuation | 15 (5.0%) | 2 (0.7%) | 3 (1.0%) |

TEAE: Treatment emergent adverse event,
SAE: Serious adverse event
n (%) = number and percentage of patients with at least one TEAE

TABLE 11

Number (%) of patients with TEAE(s) that occurred with PT ≥ 3% in any treatment group by primary SOC and PT - Safety

| Primary System Organ Class Preferred Term n (%) | Lixisenatide (N = 298) | Insulin Glulisine QD (N = 301) | Insulin Glulisine TID (N = 294) |
|---|---|---|---|
| Any class | 221 (74.2%) | 222 (73.8%) | 236 (80.3%) |
| Infections and infestations | 70 (23.5%) | 70 (23.3%) | 81 (27.6%) |

TABLE 11-continued

Number (%) of patients with TEAE(s) that occurred with PT ≥ 3% in any treatment group by primary SOC and PT - Safety

| Primary System Organ Class<br>Preferred Term n (%) | Lixisenatide<br>(N = 298) | Insulin<br>Glulisine QD<br>(N = 301) | Insulin<br>Glulisine TID<br>(N = 294) |
|---|---|---|---|
| Nasopharyngitis | 14 (4.7%) | 21 (7.0%) | 18 (6.1%) |
| Upper respiratory tract infection | 8 (2.7%) | 5 (1.7%) | 11 (3.7%) |
| Influenza | 5 (1.7%) | 8 (2.7%) | 14 (4.8%) |
| Metabolism and nutrition disorders | 111 (37.2%) | 143 (47.5%) | 157 (53.4%) |
| Hypoglycaemia | 107 (35.9%) | 140 (46.5%) | 154 (52.4%) |
| Nervous system disorders | 32 (10.7%) | 22 (7.3%) | 29 (9.9%) |
| Headache | 20 (6.7%) | 8 (2.7%) | 12 (4.1%) |
| Gastrointestinal disorders | 105 (35.2%) | 26 (8.6%) | 22 (7.5%) |
| Nausea | 75 (25.2%) | 5 (1.7%) | 3 (1.0%) |
| Vomiting | 26 (8.7%) | 5 (1.7%) | 6 (2.0%) |
| Diarrhoea | 20 (6.7%) | 10 (3.3%) | 4 (1.4%) |
| Investigations | 69 (23.2%) | 76 (25.2%) | 92 (31.3%) |
| Blood glucose decreased | 60 (20.1%) | 67 (22.3%) | 82 (27.9%) |
| Injury, poisoning and procedural complications | 14 (4.7%) | 20 (6.6%) | 28 (9.5%) |
| Accidental overdose | 0 | 13 (4.3%) | 20 (6.8%) |

TEAE: Treatment emergent adverse event, SOC: System organ class
MedDRA 17.1
n (%) = number and percentage of patients with at least one TEAE
Note:
Table sorted by SOC internationally agreed order and decreasing frequency of PT in Lixisenatide main meal group.

3.3.2 Serious Treatment-emergent Adverse Events

TABLE 12

Number (%) of patients with treatment emergent SAE presented by primary SOC and PT - Safety population

| Primary System Organ Class<br>Preferred Term n (%) | Lixisenatide<br>(N = 298) | Insulin<br>Glulisine<br>QD<br>(N = 301) | Insulin<br>Glulisine<br>TID<br>(N = 294) |
|---|---|---|---|
| Any class | 11 (3.7%) | 11 (3.7%) | 14 (4.8%) |
| Infections and infestations | 3 (1.0%) | 1 (0.3%) | 1 (0.3%) |
| Cellulitis | 0 | 1 (0.3%) | 1 (0.3%) |
| Erysipelas | 1 (0.3%) | 0 | 0 |
| Penile infection | 1 (0.3%) | 0 | 0 |
| Septic arthritis staphylococcal | 1 (0.3%) | 0 | 0 |
| Neoplasms benign, malignant and unspecified (incl cysts and polyps) | 3 (1.0%) | 0 | 3 (1.0%) |
| Invasive ductal breast carcinoma | 1 (0.3%) | 0 | 1 (0.3%) |
| Pancreatic carcinoma metastatic | 1 (0.3%) | 0 | 0 |
| Uterine cancer | 1 (0.3%) | 0 | 0 |
| Basal cell carcinoma | 0 | 0 | 1 (0.3%) |
| Neoplasm malignant [a] | 0 | 0 | 1 (0.3%) |
| Metabolism and nutrition disorders | 1 (0.3%) | 2 (0.7%) | 0 |
| Hypoglycaemia | 0 | 1 (0.3%) | 0 |
| Decreased appetite | 1 (0.3%) | 0 | 0 |
| Dehydration | 1 (0.3%) | 1 (0.3%) | 0 |
| Nervous system disorders | 1 (0.3%) | 3 (1.0%) | 2 (0.7%) |
| Cerebrovascular accident | 1 (0.3%) | 0 | 2 (0.7%) |
| Hypoglycaemic unconsciousness | 0 | 2 (0.7%) | 0 |
| Neuritis cranial | 0 | 1 (0.3%) | 0 |
| Cardiac disorders | 1 (0.3%) | 3 (1.0%) | 5 (1.7%) |
| Angina pectoris | 1 (0.3%) | 0 | 1 (0.3%) |
| Cardiac failure chronic | 0 | 0 | 1 (0.3%) |
| Cardiac failure congestive | 0 | 0 | 1 (0.3%) |
| Myocardial ischaemia | 0 | 0 | 1 (0.3%) |
| Angina unstable | 0 | 1 (0.3%) | 0 |
| Atrial fibrillation | 0 | 1 (0.3%) | 0 |
| Atrioventricular block complete | 0 | 0 | 1 (0.3%) |
| Myocardial infarction | 0 | 1 (0.3%) | 0 |
| Vascular disorders | 0 | 0 | 1 (0.3%) |
| Hypertension | 0 | 0 | 1 (0.3%) |
| Gastrointestinal disorders | 2 (0.7%) | 0 | 0 |
| Abdominal pain | 1 (0.3%) | 0 | 0 |
| Epigastric discomfort | 1 (0.3%) | 0 | 0 |
| Gastric ulcer haemorrhage | 1 (0.3%) | 0 | 0 |
| Hepatobiliary disorders | 1 (0.3%) | 0 | 0 |
| Hepatic mass | 1 (0.3%) | 0 | 0 |

TABLE 12-continued

Number (%) of patients with treatment emergent SAE
presented by primary SOC and PT - Safety population

| Primary System Organ Class<br>Preferred Term n (%) | Lixisenatide<br>(N = 298) | Insulin<br>Glulisine<br>QD<br>(N = 301) | Insulin<br>Glulisine<br>TID<br>(N = 294) |
|---|---|---|---|
| Skin and subcutaneous tissue disorders | 1 (0.3%) | 0 | 1 (0.3%) |
| Diabetic bullosis | 1 (0.3%) | 0 | 0 |
| Skin ulcer haemorrhage | 0 | 0 | 1 (0.3%) |
| Renal and urinary disorders | 2 (0.7%) | 0 | 0 |
| Renal failure | 1 (0.3%) | 0 | 0 |
| Renal failure acute | 1 (0.3%) | 0 | 0 |
| Injury, poisoning and procedural complications | 0 | 4 (1.3%) | 1 (0.3%) |
| Accidental overdose | 0 | 2 (0.7%) | 1 (0.3%) |
| Ankle fracture | 0 | 1 (0.3%) | 0 |
| Incisional hernia | 0 | 1 (0.3%) | 0 |

TEAE: Treatment emergent adverse event, SOC: System organ class, PT: Preferred term
MedDRA 17.1
[a] basal cell cancer reported as "carcinoma on left side above hairline"
n (%) = number and percentage of patients with at least one treatment emergent SAE.
Note:
Table sorted by SOC internationally agreed order and decreasing frequency of PT in Lixisenatide main meal group.

3.3.3 Adverse Events Leading to Permanent IMP Discontinuation

TABLE 13

Number (%) of patients experiencing TEAE(s) leading to permanent treatment discontinuation
by primary SOC and PT during on-treatment period - Safety population

| Primary System Organ Class<br>Preferred Term n (%) | Lixisenatide<br>(N = 298) | Insulin<br>Glulisine<br>QD<br>(N = 301) | Insulin<br>Glulisine<br>TID<br>(N = 294) |
|---|---|---|---|
| Any class | 15 (5.0%) | 2 (0.7%) | 3 (1.0%) |
| Neoplasms benign, malignant and unspecified (incl cysts and polyps) | 2 (0.7%) | 0 | 0 |
| Invasive ductal breast carcinoma | 1 (0.3%) | 0 | 0 |
| Metastases to liver | 1 (0.3%) | 0 | 0 |
| Metastases to peritoneum | 1 (0.3%) | 0 | 0 |
| Pancreatic carcinoma metastatic | 1 (0.3%) | 0 | 0 |
| Blood and lymphatic system disorders | 1 (0.3%) | 0 | 0 |
| Lymphadenopathy | 1 (0.3%) | 0 | 0 |
| Immune system disorders | 0 | 0 | 1 (0.3%) |
| Seasonal allergy | 0 | 0 | 1 (0.3%) |
| Metabolism and nutrition disorders | 2 (0.7%) | 0 | 0 |
| Hypoglycaemia | 1 (0.3%) | 0 | 0 |
| Decreased appetite | 1 (0.3%) | 0 | 0 |
| Dehydration | 1 (0.3%) | 0 | 0 |
| Nervous system disorders | 1 (0.3%) | 1 (0.3%) | 0 |
| Headache | 1 (0.3%) | 0 | 0 |
| Tremor | 0 | 1 (0.3%) | 0 |
| Cardiac disorders | 0 | 0 | 1 (0.3%) |
| Cardiac failure chronic | 0 | 0 | 1 (0.3%) |
| Vascular disorders | 2 (0.7%) | 0 | 0 |
| Hot flush | 1 (0.3%) | 0 | 0 |
| Thrombosis | 1 (0.3%) | 0 | 0 |
| Respiratory, thoracic and mediastinal disorders | 2 (0.7%) | 0 | 0 |
| Cough | 1 (0.3%) | 0 | 0 |
| Nasal congestion | 1 (0.3%) | 0 | 0 |
| Gastrointestinal disorders | 11 (3.7%) | 0 | 0 |
| Nausea | 4 (1.3%) | 0 | 0 |
| Vomiting | 4 (1.3%) | 0 | 0 |
| Diarrhoea | 1 (0.3%) | 0 | 0 |
| Abdominal pain | 1 (0.3%) | 0 | 0 |
| Dyspepsia | 1 (0.3%) | 0 | 0 |
| Ascites | 2 (0.7%) | 0 | 0 |
| Epigastric discomfort | 1 (0.3%) | 0 | 0 |
| Gastric ulcer haemorrhage | 1 (0.3%) | 0 | 0 |
| Hepatobiliary disorders | 1 (0.3%) | 0 | 0 |
| Hepatic mass | 1 (0.3%) | 0 | 0 |
| Skin and subcutaneous tissue disorders | 1 (0.3%) | 0 | 1 (0.3%) |
| Diabetic bullosis | 1 (0.3%) | 0 | 0 |
| Skin ulcer haemorrhage | 0 | 0 | 1 (0.3%) |

TABLE 13-continued

Number (%) of patients experiencing TEAE(s) leading to permanent treatment discontinuation by primary SOC and PT during on-treatment period - Safety population

| Primary System Organ Class Preferred Term n (%) | Lixisenatide (N = 298) | Insulin Glulisine QD (N = 301) | Insulin Glulisine TID (N = 294) |
|---|---|---|---|
| Renal and urinary disorders | 1 (0.3%) | 0 | 0 |
| Renal failure | 1 (0.3%) | 0 | 0 |
| Investigations | 0 | 1 (0.3%) | 0 |
| Blood glucose decreased | 0 | 1 (0.3%) | 0 |

TEAE: Treatment emergent adverse event, SOC: System organ class, PT: Preferred term
MedDRA 17.1
n (%) = number and percentage of patients with at least one TEAE leading to permanent treatment discontinuation
Note:
Table sorted by SOC internationally agreed order and decreasing frequency of PT in Lixisenatide group.

3.3.4 Other Significant Adverse Events
Symptomatic Hypoglycemia

TABLE 14

Summary of symptomatic hypoglycemia meeting the protocol definition during the TEAE period - Safety population

| Type | Lixisenatide (N = 298) | Insulin Glulisine QD (N = 301) | Insulin Glulisine TID (N = 294) |
|---|---|---|---|
| Total patient years | 144.6 | 148.3 | 146.2 |
| Any symptomatic hypoglycemia | | | |
| Number of patients with events, n (%) | 98 (32.9%) | 117 (38.9%) | 132 (44.9%) |
| Number of patients with events per 100 patient years[1] | 67.8 | 78.9 | 90.3 |
| Number of events | 332 | 395 | 600 |
| Number of events per 100 patient years[2] | 229.6 | 266.4 | 410.4 |

Symptomatic hypoglycemia = symptomatic hypoglycemia as defined per protocol (accompanied by plasma glucose < 60 mg/dL [3.3 mmol/L] or associated with prompt recovery to countermeasures if no plasma glucose was available).
On-treatment period = the time from the first injection of the investigational medicinal product up to 3 days after the last injection of the investigational medicinal product.
[1]Calculated as (number of patients with events* 100 divided by total exposure + 3 days in patient years).
[2]Calculated as (number of events* 100 divided by total exposure + 3 days in patient years).

Allergic Reaction

TABLE 15

Number (%) of patients with events adjudicated as allergic reaction by ARAC during the TEAE period - Safety population

| Relationship to study treatment (by ARAC) | ARAC diagnosis category | MedDRA coded term (PT) for ARAC diagnosis | Lixisenatide (N = 298) | Insulin Glulisine QD (N = 301) | Insulin Glulisine TID (N = 294) |
|---|---|---|---|---|---|
| All | Any category | Any event | 3 (1.0%) | 0 | 1 (0.3%) |
| | URTICARIA (HIVES) | Urticaria | 1 (0.3%) | 0 | 0 |
| | OTHER ALLERGIC REACTION | Rhinitis allergic | 2 (0.7%) | 0 | 1 (0.3%) |
| Possibly Related to IMP | Any category | Any event | 0 | 0 | 0 |

ARAC = Allergic Reaction Assessment Committee.
IMP = investigational medicinal product.

Pancreatitis

TABLE 16

Number (%) of patients with any event adjudicated as pancreatitis by PSAC during the TEAE period - Safety population

| | Lixisenatide (N = 298) | Insulin Glulisine QD (N = 301) | Insulin Glulisine TID (N = 294) |
|---|---|---|---|
| Total number of patients with any event adjudicated as pancreatitis by PSAC | 1 (0.3%) | 0 | 0 |
| Acute pancreatitis | 1 (0.3%) | 0 | 0 |
| Acute on chronic pancreatitis | 0 | 0 | 0 |
| Chronic pancreatitis | 0 | 0 | 0 |
| Unknown pancreatitis | 0 | 0 | 0 |

PSAC = Pancreas Safety Assessment Committee.

Calcitonin

TABLE 17

Number (%) of patients with TEAE reported on the specific adverse event form for increased calcitonin (>=20 ng/L) - Safety population

| Preferred Term | Lixisenatide (N = 298) | Insulin Glulisine QD (N = 301) | Insulin Glulisine TID (N = 294) |
|---|---|---|---|
| Any | 2 (0.7%) | 0 | 1 (0.3%) |
| Blood calcitonin increased | 2 (0.7%) | 0 | 1 (0.3%) |

TEAE: Treatment emergent adverse event

EXAMPLE 2

Advancing Basal Insulin Glargine with Prandial Lixisenatide QD Vs Insulin Glulisine QD or TID in Obese T2DM: The GetGoal-Duo2 Evidence-Based Trial To provide evidence on how to advance basal insulin (BI), we explored treatment options in poorly controlled BI-treated (≥6 mol±1-3 OADs) obese adults with T2DM randomized to lixisenatide 20 μg QD (LIXI), insulin glulisine QD (GLU-1), or GLU TID (GLU-3), all added to insulin glargine (IG)±metformin, if $HbA_{1c}$ remained >7-9% after a 12-week IG optimization run-in period stopping other OADs. Co-primary endpoints at 26 weeks were (1) non-inferiority (95% CI upper bound <0.4%) in $HbA_{1c}$ reduction with LIXI vs GLU-1 and (2) for LIXI vs GLU-3, either non-inferiority in $HbA_{1c}$ reduction (2a) OR superiority (one-sided α≤0.025) in body weight change (2b). FPG, PPG, IG dose, composite outcomes, AEs, and hypoglycemia were assessed. Each arm randomized 298 pts (T2DM duration 12 yrs, BI duration 3 yrs, weight ~90 kg). All co-primary endpoints were met as LIXI was non-inferior to GLU-1 and GLU-3 for $HbA_{1c}$ reductions and statistically superior to both for body weight loss (Table). Documented hypoglycemia was numerically and significantly lower with LIXI than with GLU-1 and GLU-3, respectively. In conclusion, BI plus LIXI, if tolerated, may become a preferred option to advance BI, attaining meaningful glycemic targets with less hypoglycemia and with weight loss compared with prandial insulin as Basal Plus or Basal/Bolus for difficult to control, obese, insulin-treated T2DM.

TABLE

| Outcomes | Lixisenatide 20 μg QD + Insulin Glargine (n = 297) | Insulin Glulisine QD + Insulin Glargine (n = 298) | Insulin Glulisine TID + Insulin Glargine (n = 295) |
|---|---|---|---|
| FPG, mg/dL | | | |
| Screening (start run-in) mean ± SD | 165 ± 53 | 167 ± 52 | 171 ± 53 |
| BL (end run-in) mean ± SD | 119 ± 33 | 123 ± 36 | 120 ± 34 |
| Week 26 (LOCF) mean ± SD | 119 ± 35 | 120 ± 35 | 121 ± 36 |
| LS mean ± SE change from BL | −4 ± 3 | −4 ± 3 | −1 ± 3 |
| LS mean [95% CI] treatment difference | — | 0 [−6, 5] | −3 [−9, 3] |
| 2-h PPG post test meal, mg/dL* | | | |
| BL (end run-in) mean ± SD | 254 ± 65 | 249 ± 63 | 262 ± 63 |
| Week 26 (LOCF) mean ± SD | 184 ± 70 | 220 ± 60 | 229 ± 69 |
| LS mean ± SE change from BL | −66 ± 11 | −28 ± 11 | −25 ± 11 |
| LS mean [95% CI] treatment difference | — | −37 [−59, −15] | −40 [−61, −19] |
| $HbA_{1c}$, % | | | |
| Screening (start run-in) mean ± SD | 8.5 ± 0.7 | 8.5 ± 0.7 | 8.5 ± 0.8 |
| BL (end run-in) mean ± SD | 7.8 ± 0.6 | 7.7 ± 0.6 | 7.8 ± 0.6 |
| Week 26 (LOCF) mean ± SD | 7.2 ± 0.8 | 7.2 ± 0.8 | 7.0 ± 0.7 |
| LS mean ± SE change from BL | −0.6 ± 0.1 | −0.6 ± 0.1 | −0.8 ± 0.1 |
| LS mean [95% CI] treatment difference | — | −0.1† [−0.2, 0.1] | 0.2† [0.1, 0.3] |
| Insulin Glargine dose, U/day | | | |
| Screening (start run-in) mean ± SD | 41 ± 22 | 40 ± 22 | 39 ± 2 |
| BL (end run-in) mean ± SD | 67 ± 32 | 65 ± 32 | 65 ± 27 |
| Week 26 (LOCF) mean ± SD | 67 ± 36 | 64 ± 36 | 61 ± 29 |
| LS mean + SE change from BL | 0.7 ± 1.0 | −0.1 ± 1.0 | −3.1 ± 1.0 |
| LS mean [95% CI] treatment difference | — | 0.8 [−1.4, 2.9] | 3.9 [1.7, 6.0] |

TABLE-continued

| Outcomes | Lixisenatide 20 μg QD + Insulin Glargine (n = 297) | Insulin Glulisine QD + Insulin Glargine (n = 298) | Insulin Glulisine TID + Insulin Glargine (n = 295) |
|---|---|---|---|
| Insulin Glulisine dose, U/day | | | |
| Week 26 (LOCF) mean | — | 10 | 20 |
| Body Weight, kg | | | |
| BL mean ± SD | 90.1 ± 17.4 | 88.4 ± 15.9 | 90.0 ± 17.2 |
| Week 26 (LOCF) mean ± SD | 89.4 ± 18.1 | 89.3 ± 16.3 | 91.3 ± 17.3 |
| LS mean ± SE change from BL | −0.6 ± 0.3 | 1.0 ± 0.3 | 1.4 ± 0.3 |
| LS mean [95% CI] treatment difference | — | −1.7 [−2.3, −1.1] | −2.0 [−2.6, −1.4] |
| (p-value vs Lixisenatide) | — | ($p < 0.0001$) | ($p < 0.0001$)[†] |
| Documented Symptomatic Hypoglycemia at Week 26 | | | |
| % pts (p-value vs Lixisenatide) | 31.5 | 37.5 ($p = 0.144$) | 44.6 ($p = 0.001$) |
| No. of events | 325 | 384 | 595 |
| No. of events/pt years | 2.2 | 2.6 | 4.1 |
| Estimated rate ratio Lixisenatide:Glulisine [95% CI] | — | 0.8 [0.5, 1.1] | 0.5 [0.3, 0.7] |
| (p-value vs Lixisenatide) | — | ($p = 0.123$) | ($p < 0.0001$) |
| Severe Hypoglycemia, no. of pts with events | 0 | 2 | 0 |
| Gastrointestinal AEs, n (%)[‡] | | | |
| Nausea | 75 (25) | 5 (2) | 3 (1) |
| Diarrhea | 20 (7) | 10 (3) | 4 (1) |
| Vomiting | 26 (9) | 5 (2) | 6 (2) |

*Subset of the mITT population treated with lixisenatide or insulin glulisine before breakfast;
[†]co-primary endpoints;
[‡]safety population.
AEs, adverse events; BL, baseline; CI, confidence interval; FPG, fasting plasma glucose; HbA$_{1c}$, glycated hemoglobin; LOCF, last observation carried forward; LS, least squares; mITT, modified intent-to-treat; PPG, postprandial glucose; QD, once daily; SD, standard deviation; SE, standard error; TID, thrice daily.
n numbers are for the mITT population (all pts who received ≥1 dose of study medication, with both a baseline assessment and ≥1 post-baseline assessment).

---

The invention claimed is:

1. A method for improving glycemic control in a patient with type 2 diabetes mellitus comprising:
   administering to the patient in need thereof a therapeutically effective amount of a pharmaceutical combination comprising lixisenatide and insulin glargine;
   wherein the patient has a body mass index (BMI)≥30 kg/m$^2$ or has experienced a hypoglycemic event;
   wherein the patient's type 2 diabetes mellitus is not adequately controlled after treatment with basal insulin; and
   wherein the patient requires additional glycemic control without the increase in hypoglycemia and weight gain of prandial insulin.

2. The method of claim 1, wherein the patient's type 2 diabetes mellitus is not adequately controlled after treatment with basal insulin and metformin.

3. The method of claim 1, wherein the patient's type 2 diabetes mellitus is not adequately controlled after treatment with basal insulin and one to three oral anti-diabetic drugs (OADs).

4. The method of claim 3, wherein the one to three OADs are selected from the group consisting of metformin, sulfonylureas, dipeptidyl-peptidase-4 (DPP-4) inhibitors, glinides, or combinations thereof.

* * * * *